US011937904B2

(12) United States Patent
Ochs et al.

(10) Patent No.: US 11,937,904 B2
(45) Date of Patent: Mar. 26, 2024

(54) DETECTING THE END OF CARDIO MACHINE ACTIVITIES ON A WEARABLE DEVICE

(71) Applicant: Apple Inc., Cupertino, CA (US)

(72) Inventors: James P. Ochs, San Francisco, CA (US); Mariah W. Whitmore, Cupertino, CA (US); Mark P. Sena, Larkspur, CA (US); Julia K. Nichols, Alameda, CA (US); Erin Paeng, Portland, OR (US); Vinay R. Majjigi, Mountain View, CA (US); Karthik Jayaraman Raghuram, Mountain View, CA (US); Hung A. Pham, Oakland, CA (US)

(73) Assignee: Apple Inc., Cupertino, CA (US)

( * ) Notice: Subject to any disclaimer, the term of this patent is extended or adjusted under 35 U.S.C. 154(b) by 353 days.

(21) Appl. No.: 17/016,020

(22) Filed: Sep. 9, 2020

(65) Prior Publication Data

US 2021/0068689 A1 Mar. 11, 2021

Related U.S. Application Data

(60) Provisional application No. 62/897,722, filed on Sep. 9, 2019.

(51) Int. Cl.
*A61B 5/24* (2021.01)
*A61B 5/00* (2006.01)
(Continued)

(52) U.S. Cl.
CPC ...... *A61B 5/02438* (2013.01); *A61B 5/02416* (2013.01); *A61B 5/1118* (2013.01); *A61B 5/6813* (2013.01); *A61B 2562/0223* (2013.01)

(58) Field of Classification Search
CPC ............ A61B 5/02438; A61B 5/02416; A61B 5/1118; A61B 5/6813; A61B 5/0223
(Continued)

(56) References Cited

U.S. PATENT DOCUMENTS

| 4,566,461 A | 1/1986 | Lubell et al. |
| 4,740,009 A | 4/1988 | Hoelzl |

(Continued)

FOREIGN PATENT DOCUMENTS

| AU | 2008100295 A4 | 5/2008 |
| CN | 102481479 A | 5/2012 |

(Continued)

OTHER PUBLICATIONS

U.S. Appl. No. 17/015,912, filed Sep. 9, 2020, Humblet et al.
(Continued)

*Primary Examiner* — Carl H Layno
*Assistant Examiner* — Michael J Lau
(74) *Attorney, Agent, or Firm* — Fish & Richardson P.C.

(57) ABSTRACT

Disclosed embodiments include wearable devices and techniques for detecting cardio machine activities, estimating user direction of travel, and monitoring performance during cardio machine activities. By accurately and promptly detecting cardio machine activities and automatically distinguishing between activities performed on different types of cardio machines, the disclosure enables wearable devices to accurately calculate user performance information when users forget to start and/or stop recording activities on a wide variety of cardio machines. In various embodiments, cardio machine activity detection techniques may use magnetic field data from a magnetic field sensor to improve the accuracy of orientation data and device heading measurements used to detect the end of a cardio machine activity.

19 Claims, 22 Drawing Sheets

(51) Int. Cl.
  *A61B 5/024* (2006.01)
  *A61B 5/11* (2006.01)
(58) Field of Classification Search
  USPC .......................................................... 600/508
  See application file for complete search history.

(56) References Cited

U.S. PATENT DOCUMENTS

| | | | |
|---|---|---|---|
| 5,158,093 A | 10/1992 | Shvartz et al. | |
| 5,663,897 A | 9/1997 | Geiser | |
| 5,664,499 A | 9/1997 | Kingsmill | |
| 6,013,008 A | 1/2000 | Fukushima | |
| 6,059,724 A | 5/2000 | Campbell et al. | |
| 6,582,380 B2 | 6/2003 | Kazlausky et al. | |
| 6,687,535 B2 | 2/2004 | Hautala et al. | |
| 6,837,827 B1 | 1/2005 | Lee et al. | |
| 6,862,525 B1 | 3/2005 | Beason et al. | |
| 6,868,338 B1 | 3/2005 | Elliott | |
| 6,876,947 B1 | 4/2005 | Darley et al. | |
| 7,254,516 B2 | 8/2007 | Case et al. | |
| 7,311,675 B2 | 12/2007 | Peifer et al. | |
| 7,377,180 B2 | 5/2008 | Cunningham | |
| 7,387,029 B2 | 6/2008 | Cunningham | |
| 7,467,060 B2 | 12/2008 | Kulach et al. | |
| 7,534,206 B1 | 5/2009 | Lovitt et al. | |
| 7,647,196 B2 | 1/2010 | Kahn et al. | |
| 7,690,556 B1 | 4/2010 | Kahn et al. | |
| 7,771,320 B2 | 8/2010 | Riley et al. | |
| 7,805,149 B2 | 9/2010 | Werner et al. | |
| 7,841,967 B1 | 11/2010 | Kahn et al. | |
| 8,290,480 B2 | 10/2012 | Abramson et al. | |
| 8,483,775 B2 | 7/2013 | Buck et al. | |
| 8,531,180 B2 | 9/2013 | Piemonte et al. | |
| 8,589,174 B2 | 11/2013 | Nelson et al. | |
| 8,638,320 B2 | 1/2014 | Harley et al. | |
| 8,653,956 B2 | 2/2014 | Berkobin et al. | |
| 8,784,271 B2 | 7/2014 | Brumback et al. | |
| 8,890,854 B2 | 11/2014 | Tenuta et al. | |
| 8,892,391 B2 | 11/2014 | Tu et al. | |
| 8,894,576 B2 | 11/2014 | Alwan et al. | |
| 8,911,329 B2 | 12/2014 | Lin et al. | |
| 8,928,635 B2 | 1/2015 | Harley et al. | |
| 9,195,305 B2 | 11/2015 | Markovic et al. | |
| 9,264,862 B2 | 2/2016 | Tu et al. | |
| 9,413,871 B2 | 8/2016 | Nixon et al. | |
| 9,448,250 B2 | 9/2016 | Pham et al. | |
| 9,526,430 B2 | 12/2016 | Srinivas et al. | |
| 9,704,412 B2 * | 7/2017 | Wells | G16H 20/40 |
| 9,737,761 B1 * | 8/2017 | Sivaraj | G16H 20/30 |
| 9,788,794 B2 | 10/2017 | Leboeuf et al. | |
| 9,817,948 B2 | 11/2017 | Swank et al. | |
| 9,918,646 B2 | 3/2018 | Alvarado et al. | |
| 9,998,864 B2 | 6/2018 | Kumar et al. | |
| 10,098,549 B2 | 10/2018 | Tan et al. | |
| 10,154,789 B2 | 12/2018 | Raghuram et al. | |
| 10,188,347 B2 | 1/2019 | Self et al. | |
| 10,206,627 B2 | 2/2019 | Leboeuf et al. | |
| 10,219,708 B2 | 3/2019 | Altini | |
| 10,244,948 B2 | 4/2019 | Pham et al. | |
| 10,290,260 B2 | 5/2019 | Wu et al. | |
| 10,292,606 B2 | 5/2019 | Wisbey et al. | |
| 10,512,406 B2 | 12/2019 | Martinez et al. | |
| 10,524,670 B2 | 1/2020 | Raghuram et al. | |
| 10,620,232 B2 | 4/2020 | Tu et al. | |
| 10,687,707 B2 | 6/2020 | Tan et al. | |
| 10,687,752 B2 | 6/2020 | Pham et al. | |
| 10,694,994 B2 | 6/2020 | Alvarado et al. | |
| 10,699,594 B2 | 6/2020 | Mermel et al. | |
| 10,617,912 B2 | 7/2020 | Narasimha Rao et al. | |
| 10,709,933 B2 | 7/2020 | Tan et al. | |
| 11,051,720 B2 | 7/2021 | Perry et al. | |
| 11,103,749 B2 | 8/2021 | Mermel et al. | |
| 11,278,765 B2 | 3/2022 | Mohrman et al. | |
| 11,517,789 B2 | 12/2022 | Xie et al. | |
| 2001/0022828 A1 | 9/2001 | Pyles | |
| 2002/0019585 A1 | 2/2002 | Dickinson | |
| 2003/0032460 A1 | 2/2003 | Cannon et al. | |
| 2003/0138763 A1 | 7/2003 | Roncalez et al. | |
| 2004/0064061 A1 | 4/2004 | Nissila | |
| 2005/0065443 A1 * | 3/2005 | Ternes | A61B 5/0205 600/509 |
| 2005/0107723 A1 | 5/2005 | Wehman et al. | |
| 2005/0124906 A1 | 6/2005 | Childre et al. | |
| 2005/0212701 A1 | 9/2005 | Nimmo | |
| 2006/0046898 A1 * | 3/2006 | Harvey | A63B 71/0697 482/8 |
| 2006/0064277 A1 | 3/2006 | Jung et al. | |
| 2006/0136173 A1 | 6/2006 | Case et al. | |
| 2006/0190217 A1 | 8/2006 | Lee et al. | |
| 2006/0217231 A1 | 9/2006 | Parks et al. | |
| 2007/0100666 A1 | 5/2007 | Stivoric et al. | |
| 2007/0150229 A1 | 6/2007 | Fujiwara | |
| 2007/0219059 A1 | 9/2007 | Schwartz et al. | |
| 2007/0275825 A1 | 11/2007 | O'Brien | |
| 2007/0276271 A1 | 11/2007 | Chan | |
| 2008/0096726 A1 | 4/2008 | Riley et al. | |
| 2008/0214360 A1 | 9/2008 | Stirling et al. | |
| 2009/0009320 A1 | 1/2009 | O'Connor et al. | |
| 2009/0024332 A1 | 1/2009 | Karlov et al. | |
| 2009/0043531 A1 | 2/2009 | Kahn et al. | |
| 2009/0063099 A1 | 3/2009 | Counts et al. | |
| 2009/0143199 A1 | 6/2009 | Nishibayashi | |
| 2009/0240461 A1 | 9/2009 | Makino et al. | |
| 2009/0319221 A1 | 12/2009 | Kahn et al. | |
| 2010/0030350 A1 | 2/2010 | House et al. | |
| 2010/0030482 A1 | 2/2010 | Li | |
| 2010/0130890 A1 | 5/2010 | Matsumura et al. | |
| 2010/0184564 A1 | 7/2010 | Molyneux et al. | |
| 2010/0204952 A1 | 8/2010 | Irlam et al. | |
| 2010/0210953 A1 | 8/2010 | Sholder et al. | |
| 2010/0210975 A1 | 8/2010 | Anthony et al. | |
| 2010/0217099 A1 | 8/2010 | Leboeuf et al. | |
| 2010/0274102 A1 | 10/2010 | Teixeira | |
| 2010/0298656 A1 | 11/2010 | McCombie et al. | |
| 2011/0040193 A1 | 2/2011 | Seppanen et al. | |
| 2011/0054359 A1 | 3/2011 | Sazonov et al. | |
| 2011/0082008 A1 | 4/2011 | Cheung et al. | |
| 2011/0131012 A1 | 6/2011 | Czaja et al. | |
| 2011/0152695 A1 | 6/2011 | Granqvist et al. | |
| 2011/0195707 A1 | 8/2011 | Faerber et al. | |
| 2011/0238485 A1 | 9/2011 | Haumont et al. | |
| 2011/0301436 A1 | 12/2011 | Teixeira | |
| 2012/0006112 A1 | 1/2012 | Lee et al. | |
| 2012/0083715 A1 | 4/2012 | Yuen et al. | |
| 2012/0172677 A1 | 7/2012 | Logan et al. | |
| 2012/0238832 A1 | 9/2012 | Jang et al. | |
| 2012/0296455 A1 | 11/2012 | Ohnemus et al. | |
| 2012/0322621 A1 | 12/2012 | Bingham et al. | |
| 2013/0006522 A1 | 1/2013 | Vellaikal et al. | |
| 2013/0023739 A1 | 1/2013 | Russell | |
| 2013/0041590 A1 | 2/2013 | Burich et al. | |
| 2013/0053990 A1 | 2/2013 | Ackland | |
| 2013/0073255 A1 | 3/2013 | Yuen et al. | |
| 2013/0085861 A1 | 4/2013 | Dunlap | |
| 2013/0096943 A1 | 4/2013 | Carey et al. | |
| 2013/0135097 A1 | 5/2013 | Doezema | |
| 2013/0158686 A1 | 6/2013 | Zhang et al. | |
| 2013/0178335 A1 | 7/2013 | Lin et al. | |
| 2013/0197377 A1 | 8/2013 | Kishi et al. | |
| 2013/0218053 A1 | 8/2013 | Kaiser et al. | |
| 2013/0267794 A1 | 10/2013 | Fernstrom et al. | |
| 2013/0326137 A1 | 12/2013 | Bilange et al. | |
| 2013/0340287 A1 | 12/2013 | Stewart | |
| 2014/0071082 A1 | 3/2014 | Singh et al. | |
| 2014/0073486 A1 | 3/2014 | Ahmed et al. | |
| 2014/0087708 A1 | 3/2014 | Kalita et al. | |
| 2014/0088444 A1 | 3/2014 | Saalasti et al. | |
| 2014/0107932 A1 | 4/2014 | Luna | |
| 2014/0109390 A1 | 4/2014 | Manning | |
| 2014/0121471 A1 | 5/2014 | Walker | |
| 2014/0167973 A1 | 6/2014 | Letchner et al. | |
| 2014/0172238 A1 | 6/2014 | Craine | |
| 2014/0172361 A1 | 6/2014 | Chiang et al. | |
| 2014/0197946 A1 | 7/2014 | Park et al. | |

(56) References Cited

U.S. PATENT DOCUMENTS

| | | |
|---|---|---|
| 2014/0200906 A1 | 7/2014 | Bentley et al. |
| 2014/0207264 A1 | 7/2014 | Quy |
| 2014/0213920 A1 | 7/2014 | Lee et al. |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266160 A1 | 9/2014 | Coza |
| 2014/0266789 A1 | 9/2014 | Matus |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0279123 A1 | 9/2014 | Harkey et al. |
| 2014/0316305 A1 | 10/2014 | Venkatraman et al. |
| 2014/0348367 A1 | 11/2014 | Vavrus et al. |
| 2015/0066526 A1* | 3/2015 | Cheng ................ G16H 20/30 |
| | | 705/2 |
| 2015/0072712 A1 | 3/2015 | Huang et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0105096 A1 | 4/2015 | Chowdhury et al. |
| 2015/0119728 A1 | 4/2015 | Blackadar et al. |
| 2015/0147734 A1 | 5/2015 | Flores et al. |
| 2015/0148632 A1 | 5/2015 | Benaron |
| 2015/0173631 A1 | 6/2015 | Richards et al. |
| 2015/0182149 A1 | 7/2015 | Rapoport et al. |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0294440 A1 | 10/2015 | Roberts |
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0357948 A1 | 12/2015 | Goldstein |
| 2015/0374240 A1 | 12/2015 | Lee |
| 2016/0021238 A1 | 1/2016 | Abramson et al. |
| 2016/0038083 A1 | 2/2016 | Ding et al. |
| 2016/0054449 A1 | 2/2016 | Pekonen et al. |
| 2016/0057372 A1 | 2/2016 | Iwane et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1* | 3/2016 | Raghuram ............. A61B 5/222 |
| | | 600/483 |
| 2016/0058370 A1* | 3/2016 | Raghuram ........... A61B 5/0002 |
| | | 600/483 |
| 2016/0058371 A1* | 3/2016 | Singh Alvarado ..... A61B 5/725 |
| | | 600/483 |
| 2016/0058372 A1* | 3/2016 | Raghuram ............. A61B 5/681 |
| | | 600/595 |
| 2016/0059079 A1 | 3/2016 | Watterson |
| 2016/0066859 A1* | 3/2016 | Crawford ............... A61B 5/681 |
| | | 600/595 |
| 2016/0069679 A1 | 3/2016 | Jackson et al. |
| 2016/0084869 A1 | 3/2016 | Yuen et al. |
| 2016/0143579 A1 | 5/2016 | Martikka |
| 2016/0147319 A1 | 5/2016 | Agarwal et al. |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0223578 A1* | 8/2016 | Klosinski, Jr. ......... G06V 40/23 |
| 2016/0242646 A1 | 8/2016 | Obma |
| 2016/0256058 A1 | 9/2016 | Pham et al. |
| 2016/0263435 A1 | 9/2016 | Venkatraman et al. |
| 2016/0269572 A1 | 9/2016 | Erkkila et al. |
| 2016/0287177 A1 | 10/2016 | Huppert et al. |
| 2016/0301581 A1* | 10/2016 | Carter .................. H04L 43/024 |
| 2016/0314633 A1 | 10/2016 | Bonanni et al. |
| 2016/0361020 A1 | 12/2016 | Leboeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roovers et al. |
| 2017/0061817 A1 | 3/2017 | Mettler |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0181644 A1 | 6/2017 | Meer et al. |
| 2017/0188893 A1 | 7/2017 | Venkatraman et al. |
| 2017/0202486 A1 | 7/2017 | Martikka et al. |
| 2017/0211936 A1 | 7/2017 | Howell et al. |
| 2017/0242499 A1 | 8/2017 | Shah et al. |
| 2017/0242500 A1 | 8/2017 | Shah et al. |
| 2017/0251972 A1 | 9/2017 | Jayaraman et al. |
| 2017/0259116 A1 | 9/2017 | Mestas |
| 2017/0269734 A1 | 9/2017 | Graff |
| 2017/0269785 A1 | 9/2017 | Abdollahian et al. |
| 2017/0273619 A1 | 9/2017 | Alvarado et al. |
| 2017/0347885 A1 | 12/2017 | Tan et al. |
| 2017/0367658 A1 | 12/2017 | Leboeuf et al. |
| 2017/0368413 A1* | 12/2017 | Shavit ................ A63B 24/0075 |
| 2018/0028863 A1 | 2/2018 | Matsuda |
| 2018/0043210 A1 | 2/2018 | Niehaus et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |
| 2018/0056129 A1* | 3/2018 | Narasimha Rao ... A61B 5/7221 |
| 2018/0279914 A1 | 10/2018 | Patek et al. |
| 2018/0303381 A1* | 10/2018 | Todd .................... A61B 5/7267 |
| 2018/0344217 A1 | 12/2018 | Perry et al. |
| 2019/0038938 A1 | 2/2019 | Nagasaka et al. |
| 2019/0076063 A1 | 3/2019 | Kent et al. |
| 2019/0090087 A1 | 3/2019 | Taylor et al. |
| 2019/0184230 A1 | 6/2019 | Lee et al. |
| 2019/0360813 A1 | 11/2019 | Zhao et al. |
| 2020/0232796 A1 | 7/2020 | Lee et al. |
| 2021/0068712 A1 | 3/2021 | Humblet et al. |
| 2021/0068713 A1 | 3/2021 | Dervisoglu et al. |
| 2021/0093917 A1 | 4/2021 | Dervisoglu et al. |
| 2021/0093918 A1 | 4/2021 | Dervisoglu et al. |
| 2022/0241641 A1 | 8/2022 | Mermel et al. |

FOREIGN PATENT DOCUMENTS

| | | |
|---|---|---|
| CN | 104218976 A | 12/2014 |
| CN | 105031905 A | 11/2015 |
| CN | 105068656 A | 11/2015 |
| GB | 2465824 A | 6/2010 |
| IN | 259/KOL/2015 | 12/2015 |
| JP | 2004089317 | 3/2004 |
| JP | 2010-051333 A | 3/2010 |
| JP | 2013-039316 A | 2/2013 |
| JP | 2014-042757 A | 3/2014 |
| JP | 2016-150018 A | 8/2016 |
| JP | 2018-000543 A | 1/2018 |
| JP | 2018-015187 A | 2/2018 |
| JP | 2019028796 | 2/2019 |
| JP | 2020148558 | 9/2020 |
| RO | 122807 B1 | 2/2010 |
| WO | 03/61779 A1 | 7/2003 |
| WO | 2010/090867 A2 | 8/2010 |
| WO | 2011/105914 A1 | 9/2011 |
| WO | 2015/126182 A1 | 8/2015 |
| WO | 2015/200900 A1 | 12/2015 |
| WO | 2016/044831 A1 | 3/2016 |
| WO | 2016/073620 A1 | 5/2016 |
| WO | WO 2016142246 | 9/2016 |
| WO | WO 2018117914 | 6/2018 |

OTHER PUBLICATIONS

U.S. Appl. No. 17/015,965, filed Sep. 9, 2020, Dervisoglu et al.
Alexander, "Energetics and Optimization of Human Walking and Running," Am J Human Biology, Mar. 20, 2002, 14:641-648.
Lasecki, "Real-Time Crowd Labeling for Deployable Activity Recognition," University of Rochester Computer Science, Feb. 23, 2013, 10 pages.

(56) References Cited

OTHER PUBLICATIONS

Latt et al., "Walking speed, cadence and step length are selected to optimize the stability of head and pelvis accelerations," Experimental Brain Research, Aug. 24, 2007, 184: 201-209.

Morgan et al., "Effect of step length optimization on the aerobic demand of running," Journal of Applied Physiology, 1994, 245-251.

PCT International Preliminary Report on Patentability in International Appln. No. PCT/US2017/049693, dated Mar. 5, 2019, 8 pages.

PCT International Preliminary Report on Patentability in International Appln. No. PCT/US2018/047290, dated Mar. 17, 2020, 9 pages.

Pfitzinger.com "Optimal Marathon Training Sessions, Distance Coach. com, Intelligent Training for Distance Runners," archived May 15, 2012, <https://web.archive.org/web/20120515081237/http://www.pfitzinger.com/marathontraining.shtml>, printed Jan. 20, 2017, 3 pages.

Romijn et al., "Regulation of endogenous fat and carbohydrate metabolism in relation to exercise intensity and duration," Am. J. Physiol., 1993, 6:1-13.

Triendurance.com "Running with a Higher Cadence, Triendurance," Oct. 23, 2021, retrieved from <https://web.archive.org/web/20080228162904/http://www.trienduranee.com/Related.asp?PageID=14&NavID=7>, 2 pages.

Mcardle, W.D. et al., "Exercise Physiology: Nutrition, Energy and Human Performance," Seventh t:amon, Lippincott Williams & Wilkins; 2010. Chapters 5-11 and 21.

Zhao, "New Developments of the Typical MEMS and Wearable Sensor Technologies," Micronanoelectronic Technology, Jan. 2015, 52(1):1-13 (with English abstract).

Zhou et al., "Development of the Technical Monitoring System for Swimming Competition," China Sport Science and Technology, Aug. 2008, 44(4):84-86 (with English abstract).

Mattfeld et al., "A New Dataset for Evaluating Pedometer Performance, " IEEE International Conference on Bioinformatics and Biomedicine (BIBM), Nov. 2017, pp. 865-869.

Unuma et al., JP2007093433, published on Apr. 12, 2007, 27 pages (machine translated English version).

Shen et al., "MiLift: Efficient Smartwatch-Based Workout Tracking Using Automatic Segmentation," Jul. 2018, 17(7):1609-1622.

"Your Fitness FAQ, Why is it important to warm up and cool down in a workout?", 2012, Web, Retrieved from: http://www.yourfitnessfaq.com/whyisitimportanttowarmupandcooldowninaworkout.html.

Bo et al., "Texive: Detecting Drivers Using Personal Smart Phones by Leveraging Inertial Sensors, " Department of ComputerScience, Illinois Institute of Technology, Chicago IL, Dec. 7, 2014, pp. 1-12.

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Bruce, RA et al., "Exercising testing in adult normal subjects and cardiac patients," Pediatrics, vol. 32, No. Suppl., pp. 742-756 (Oct. 1963).

Bruce, RA et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Chu, "In-Vehicle Driver Detection Using Mobile Phone Sensors", Submitted for Graduation with departmental Distinction in Electrical and Computer Engineering, Apr. 20, 2011, pp. 1-21.

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M et al., "Physical Activity and the Prevention of Coronary Heart Disease," Bull. N.Y. Acad. Med., vol. 44, No. 8, pp. 950-967 (Aug. 1968).

Frankenfield et al., "Comparison of Predictive Equations for Resting Metabolic Rate in Healthy Nonobese and Obese adulls: A systematic review. Journal of the American Dietetic Association", May 2005, vol. 105, No. 5, p. 775-789.

Gao et al., "Evaluation of accelerometer based multi-sensor versus single-sensor activity recognition systems", Medical engineering & physics 36.6 (2014): 779-785.

Glass et al., "ACSM's Metabolic Calculations Handbook," Lippincott Williams & Wilkins, 124 pages (2007).

Hasson et al., "Accuracy of four resting metabolic rate production equations: Effects of sex, body mass index, age, and race/ethnicity", Journal of Science and Medicine in Sport, 2011, vol. 14, p. 344-351.

Human Kinetics, Aerobic Workout Components, 2011, Web, Retrieved from: http://www.humankinetics.com/excerpts/excerpts/aerobicworkoutcomponentsexcerpt.

International Search Report and Written Opinion received for POT Patent Application No. PCT/US2018/047290, dated Nov. 8, 2018, 14 pages.

Isaacs et al., "Modeling energy expenditure and oxygen consumption in human exposure models: accounting for fatigue and EPOC", 2008, Journal of Exposure Science and Environmental Epidemiology, 18: 289-298.

Jackson et al., "Prediction of functional aerobic capacity without exercise testing, Medicine and Science in Sports and Exercise", 22(6), 863-870, 1990.

Keytel et al., "Prediction of energy expenditure from heart rate monitoring during submaximal exercise", Journal of Sports Sciences, 23(3), 2005: 289-297.

KINprof, 2011, Predictive VO2max tests, Web Video, Retrieved from: https://www.youtube.com/walch?v=_9e3HcYIsm8.

Kunze et al. "Where am i: Recognizing on-body positions of wearable sensors." Location-and context-awareness. Springer Berlin Heidelberg, 2005. 264-275.

Kyle, Chester R., "Reduction of Wind Resistance and Power Output of Racing Cyclists and Runners Travelling in Groups", Ergonomics, vol. 22, No. 4, 1979, pp. 387-397.

Lavie et al., "Impact of cardiorespiratory fitness on the obesity paradox in patients with heartfailure," Mayo Clinic Proceedings, vol. 88, No. 3, pp. 251-258 (Mar. 2013).

Le, et al., "Sensor-based Training Optimization of a Cyclist Group", Seventh International Conference on Hybrid Intelligent Systems, IEEE 2007, pp. 265-270.

Lucas et al., "Mechanisms of orthostatic intolerance following very prolonged exercise", 2008, J. Appl. Physiol., 105: pp. 213-225.

Margaria, R et al., "Energy cost of running," Journal of Applied Physiology, vol. 18, No. 2, pp. 367-370 (Mar. 1, 1963).

McArdle, W.D et al., "Exercise Physiology: Nutrition, Energy and Human Performance," Seventh t:amon, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for.

Myers et al., "Exercise Capacity and Mortality Among Men Referred for Exercise Testing," The New England Journa of Medicine, vol. 346, No. 11, pp. 793-801 {Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

(56) References Cited

OTHER PUBLICATIONS

Novatel, "IMU Error and Their Effects", Novatel Application Notes APN-064 Rev A p. 1-6, Feb. 21, 2014.
PCT International Application No. PCT/US2017/049693, International Search Report and Written Opinion dated Aug. 12, 2017.
Rapoport, Benjamin I., "Metabolic Factors Limiting Performance in Marathon Runners," PloS Computational Biology, vol. 6, Issue 10, 13 pages (Oct. 2010).
Rowlands et al. "Assessing Sedentary Behavior with the GENEActiv: Introducing the Sedentary Sphere", Medicine and science in sports and exercise, 46.6 (2014), pp. 1235-1247.
Sabatini, "Kalman-filter-based orientation determination using inertial/magnetic sensors: observability analysis and performance evaluation", Sep. 27, 2011, Sensors 2011, 11, 9182-9206.
Song et al., "Training Activity Recognition Systems Online Using Real-Time Crowdsourcing", University of Rochester Computer Science, UbiCom' 12, Sep. 5-8, 2012 (2 pages).
Tanaka, H. et al., "Age-predicted maximal heart rate revisited," Journal of the American College of Cardiology, vol. 37, Issue 1, pp. 153-156 (Jan. 2001).
Vella et al., Exercise After-Burn: Research Update, 2005, Web, Retrieved from: http://www.unm.edu/~lkravilz/Article%20folder/epocarticle.html.
Wang et al., "Time constant of heart rate recovery after low level exercise as a useful measure of cardiovascular fitness," Cont. Proc. IEEE Eng. Meda Biol. Soc., vol. 1, pp. 1799-1802: (2006).
Yamaji, et al.(Relationship Between Heart Rate and Relative Oxygen Intake in Male Subjects Aged 10 to 27 Years, 1978, J. Human Ergol., 7:29-39) (Year: 1978).

\* cited by examiner

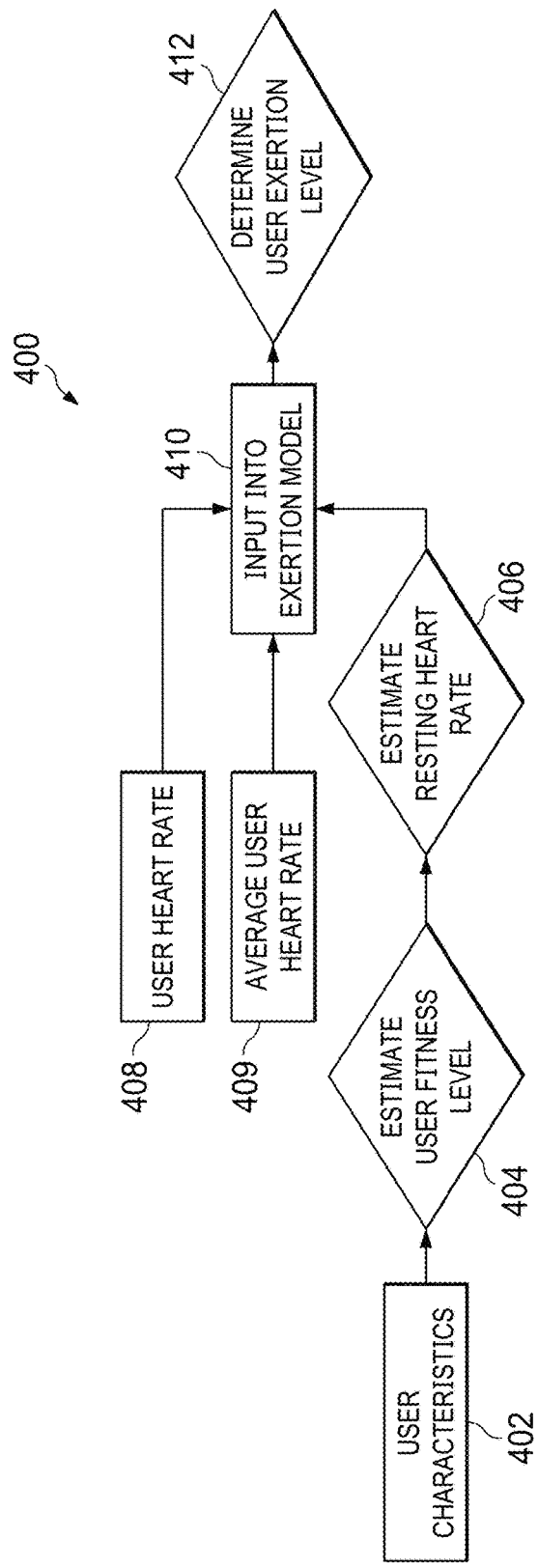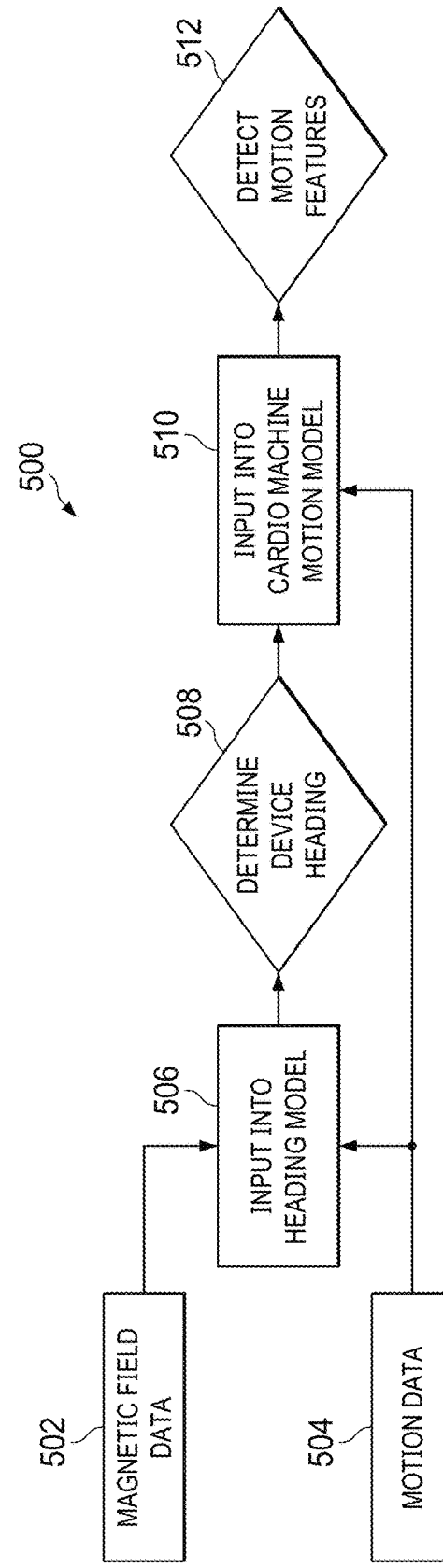

DETECTING THE END OF CARDIO MACHINE ACTIVITIES ON A WEARABLE DEVICE

CROSS REFERENCE TO RELATED APPLICATIONS

This application claims the benefit of U.S. Provisional Application Ser. No. 62/897,722 filed Sep. 9, 2019, the entire contents of which is hereby incorporated by reference.

FIELD

The present disclosure relates generally to detecting cardio machine activities using a wearable device.

BACKGROUND

A wearable device may be worn on the hand, wrist, or arm of a person when exercising on a cardio machine (e.g., rowing machine, stair stepper, treadmill, elliptical machine, indoor bicycle, and the like). It may be desirable to track cardio machine activities by a user to promote exercise and for other health related reasons. Detecting the start and end points of a cardio machine activity is an essential component of accurately tracking cardio machine activities.

SUMMARY

In one aspect disclosed herein are computer implemented methods for improving performance of a wearable device while recording a cardio-machine activity, the methods including starting the cardio machine activity on the wearable device. Embodiments may also include measuring, by a motion sensing module of the wearable device, motion data of a user. Embodiments may also include measuring, by a heart rate sensing module of the wearable device, heart rate data of the user, the heart rate sensing module including a photoplethysmogram (PPG) sensor configured to be worn adjacent to the user's skin. Embodiments may also include detecting, by the processor circuit, an end of the cardio-machine activity by determining rotational data from the motion data, the rotational data describing a position of the wearable device in a three dimensional space relative to a frame of reference. Embodiments may also include estimating a device heading based the rotational data. Embodiments may also include tracking the heading of the wearable device at multiple time points during the cardio machine activity to estimate a relative heading. Embodiments may also include detecting a variable heading by determining the relative heading exceeds a heading threshold. Embodiments may also include detecting the end of the cardio machine activity in response to detecting the variable heading. Embodiments may also include confirming the end of the cardio-machine activity based on at least one of the heart rate data and the motion data. Embodiments may also include in response to detecting the end of the cardio-machine activity, ending, by the processor circuit, the cardio machine activity.

Embodiments may also include determining, by the processor circuit, a current heart rate of the user at a point in time during the cardio machine activity based on the heart rate data. Embodiments may also include determining, by the processor circuit, an average user heart rate for the heart rate data measured during the cardio machine activity. Embodiments may also include determining, by the processor circuit, a relative heart rate by calculating a difference between the current heart rate and the average user heart rate. Embodiments may also include comparing, by the processor circuit, the relative heart rate to a relative heart rate threshold. Embodiments may also include confirming, by the processor circuit, the end of the cardio machine activity based on determining the relative heart rate falls below the relative heart rate threshold.

Embodiments may also include calculating, by the processor circuit, a level of exertion for the user based on the heart rate of the user. Embodiments may also include comparing, by the processor circuit, the level of exertion to a level of exertion threshold for the cardio-machine activity. Embodiments may also include confirming, by the processor circuit, the end of the cardio machine activity based on determining the user level of exertion falls below the level of exertion threshold.

In some embodiments, the cardio-machine activity is at least one of a rowing activity, a stair stepper activity, a treadmill/elliptical activity, and an indoor cycling activity. In some embodiments, the level of exertion threshold is different for the stair stepper activity, treadmill/elliptical activity, and indoor cycling activity. Embodiments may also include receiving, by the processor circuit, magnetic field data from a magnetic field sensor of the wearable device. Embodiments may also include improving, by the processor circuit, an accuracy of the device heading using the magnetic field data.

Embodiments may also include determining, by the processor circuit, the device heading based on a first plurality of pieces of rotational data determined based on the motion data and a second plurality of pieces of rotational data determined based on the magnetic field data. Embodiments may also include characterizing, by the processor circuit, a motion of the user during the cardio-machine activity by comparing the motion data to one or more motion features included in a motion model for the cardio-machine activity.

Embodiments may also include detecting, by the processor circuit, a non-performance of the one or more motion features included in the motion model for the cardio-machine activity. Embodiments may also include in response to detecting the non-performance the one or more motion features, confirming, by the processor circuit, the end of the cardio-machine activity. In some embodiments, the motion model for the cardio-machine activity is at least one of a motion model for a rowing activity, a motion model for a stair stepper activity, a motion model for a treadmill/elliptical activity, and a motion model for an indoor cycling activity.

In some embodiments, one or more motion features included in the motion model for the rowing activity include rowing strokes observable at intervals during the rowing activity. In some embodiments, the one or more motion features included in the motion model for the stair stepper activity and the motion model for the treadmill/elliptical activity include motion data indicating no change in the wrist pose of the user.

In some embodiments, the one or more motion features included in the motion model for the indoor cycling activity include no observable steps, a low pose of the user, and a subtle arm swing observable at intervals during the indoor cycling activity. Embodiments may also include detecting, by the processor circuit, a performance of the one or more motion features included in the motion model for the cardio-machine activity. Embodiments may also include in response to detecting the performance one or more motion features, confirming, by the processor circuit, the end of the cardio-machine activity.

In some embodiments, the motion model for the cardio-machine activity is at least one of a motion model for a rowing activity, a motion model for a stair stepper activity, a motion model for a treadmill/elliptical activity, and a motion model for an indoor cycling activity. In some embodiments, the one or more motion features for the motion model for the rowing activity include a stepping motion during the rowing activity.

In some embodiments, the one or more motion features for the motion model for the stair stepper activity include a rowing motion during the stair stepper activity. In some embodiments, the one or more motion features for the motion model for the treadmill/elliptical activity and the motion model for the indoor cycling activity include a side stepping motion during the treadmill/elliptical activity or the indoor cycling activity.

In one aspect disclosed herein are systems for improving performance of a wearable device while recording a cardio machine activity, the systems including a motion sensing module configured to collect motion data of a user. Embodiments may also include a heart rate sensing module configured to measure heart rate data of the user. In some embodiments, the heart rate sensing module may include a photoplethysmogram (PPG) sensor and the PPG sensor is configured to be worn adjacent to the user's skin. Embodiments may also include a processor circuit in communication with the motion sensing module and the heart rate sensing module, the processor circuit configured to execute instructions causing the processor circuit to begin the cardio machine activity. Embodiments may also include the processor circuit configured to determine rotational data from the motion data, the rotational data describing a position of the wearable device in a three dimensional space relative to a frame of reference. Embodiments may also include the processor circuit configured to estimate a device heading based on the rotational data. Embodiments may also include the processor circuit configured to track the device heading at multiple time points during the cardio machine activity to estimate a relative heading. Embodiments may also include the processor circuit configured to detect a variable heading by determining the relative heading exceeds a heading threshold for the cardio machine activity and detect an end of the cardio machine activity based on the variable heading. Embodiments may also include the processor circuit configured to confirm the end of the cardio machine activity based on at least one of the heart rate data and the motion data. Embodiments may also include the processor circuit configured to end the cardio machine activity in response to the confirming.

In some embodiments, the processor circuit is further configured to, determine a current heart rate of the user at a point in time during the cardio machine activity. Embodiments may also include the processor circuit configured to determine an average user heart rate for the heart rate data measured during the cardio machine activity. Embodiments may also include the processor circuit configured to determine a relative heart rate by calculating a difference between the current heart rate and the average user heart rate. Embodiments may also include the processor circuit configured to compare the relative heart rate to a relative heart rate threshold. Embodiments may also include the processor circuit configured to confirm the end of the cardio machine activity when the relative heart rate falls below the relative heart rate threshold.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 4 is a flow chart illustrating a method for determining a user level of exertion during a cardio machine activity, according to embodiments of the disclosure.

FIG. 5 is a flow chart illustrating a method for detecting motion features for cardio machine activities, according to embodiments of the disclosure

DESCRIPTION

Figure 1:
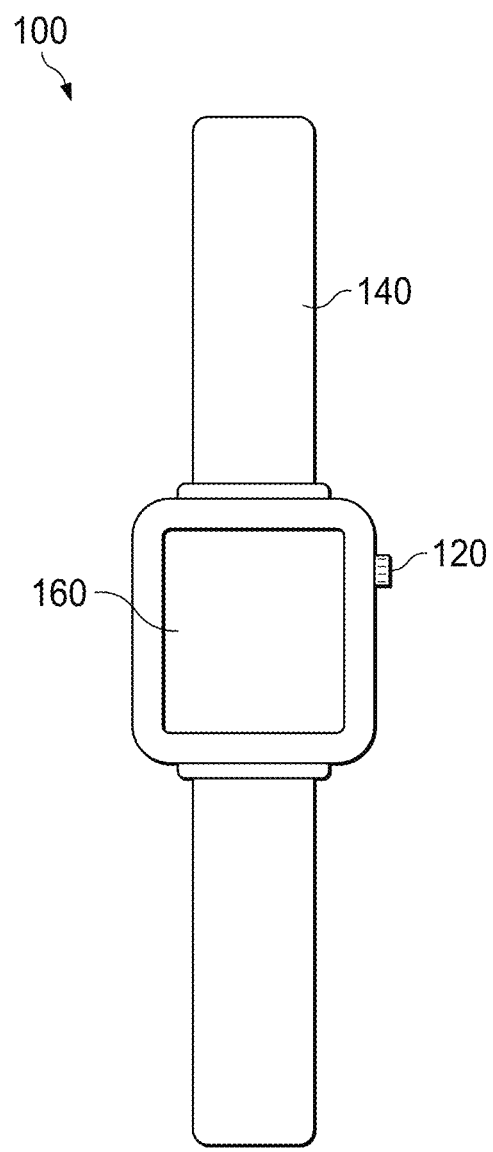
FIG. 1 is a diagram of an exemplary wearable device, according to embodiments of the disclosure.

As used herein, the term "orientation data" refers to the position or angle of a wearable device in 3d space relative to a reference frame. Orientation data may include a rotational angle about an axis of rotation (e.g., roll, pitch, yaw)

that is expressed in degrees. Orientation data may be calculated using motion data and/or magnetic field data.

As used herein, the term "motion data" refers to data generated by one or more motion sensors (e.g., a gyroscope, accelerometer, and the like).

As used herein, the term "relative orientation" refers to a change in device orientation that may be observed in orientation data calculated at different points in time. In other words relative orientation describes how the orientation of the wearable device changes over time.

As used herein, the terms "device heading", "heading", "device headings", and "headings" refer to orientation of a wearable device relative to a horizontal plane. Device headings may be calculated by computing the yaw component of orientation data.

As used herein, the terms "relative device heading", "relative heading", "relative device headings", and "relative headings" refer to changes in device headings that may be observed in device headings calculated at different points in time. In other words, relative device headings describe how the device heading of the wearable device changes over time.

The present disclosure describes systems and methods of detecting cardio machine activities using a wearable device. Users engaged in cardio machine workouts may quickly transition from machine to machine during the same exercise period. Therefore, to accurately track a user's performance during a full exercise period it is important to quickly identify the end of cardio machine activities and the transitions between activities performed on different cardio machines. In various embodiments, the wearable device may track user performance during an exercise period using one or more activity specific models (e.g., a treadmill model for treadmill activities, a stair stepper model for stair stepper activities, an outdoor running model for outdoor running activities, a rowing model for rowing machine activities, and the like). It may be important to determine the type of activity the user is performing and/or identify the type of machine used to perform the activity to more accurately track user performance across a wide range of exercise activities.

Wearable devices may be used by users all day to track a variety of different activities. For users that are active for many hours of the day, it may be difficult to fully track each activity without recharging the wearable device and/or consuming a vast amount of network data and compute resources. Certain components of the device's battery, such as the main processor, Global Positioning System (GPS) receiver, and cellular module, all can draw a particularly high amount of power and consume a vast amount of network data and compute resources (e.g., memory, processing capacity, network communications, and the like). To minimize the amount of power, network data, and compute resources consumed by the wearable device, the systems and methods disclosed herein can detect when the user ends a cardio machine activity, is transitioning between cardio machine activities, is stationary, begins performing a non-cardio machine activity, etc., and, in response, transitions the wearable device from a tracking state to a low power state. One or more components of the wearable device may be selectively powered down when the device is in a tracking state to increase battery life and reduce the amount of data and compute resources consumed. By minimizing the amount of time the wearable device is in a tracking state, the activity detection systems and methods disclosed herein improve the functioning of wearable device by making them run longer on a single charge and more efficiently by consuming less data and compute resources to deliver the same functionality.

FIG. 1 shows an example of a wearable device 100 that may be worn by a user, in accordance with an embodiment of the present disclosure. In some embodiments, the wearable device 100 may be configured to be worn around the user's wrist using a strap (e.g., a watch strap).

As described in more detail below, the wearable device 100 may be configured to detect the user's cardio machine activity, calculate performance information of the user during the cardio machine activity, detect the type of cardio machine activity performed by the user, detect transitions between two or more different cardio machines during a single exercise period, and provide additional functionality related to cardio machines to the user. In particular, the wearable device 100 may use motion data obtained from motion sensors, heart rate data obtained from a heart rate sensing module, and/or magnetic field data obtained from a magnetic field sensor to detect when the user stops a cardio machine activity, transitions between two or more cardio machines, performs a movement specific to a particular cardio machine, travels in the same direction, changes direction of travel, temporarily stops a cardio machine activity, performs a non-cardio machine activity and/or performs other cardio machine related activities. The wearable device may use a variety of motion data and orientation data to estimate the device heading which may be used to determine a user's direction of travel. Motion data and orientation data may be used by the wearable device to classify the type of cardio machine activity performed by the user and/or the type of cardio machine the user is using during exercise. Heart rate and user characteristics (e.g., age, maximum oxygen consumption, level of fitness, previous performance information, etc.) may be used by the wearable device to determine a user exertion level and/or a change in user exertion.

Figure 2:
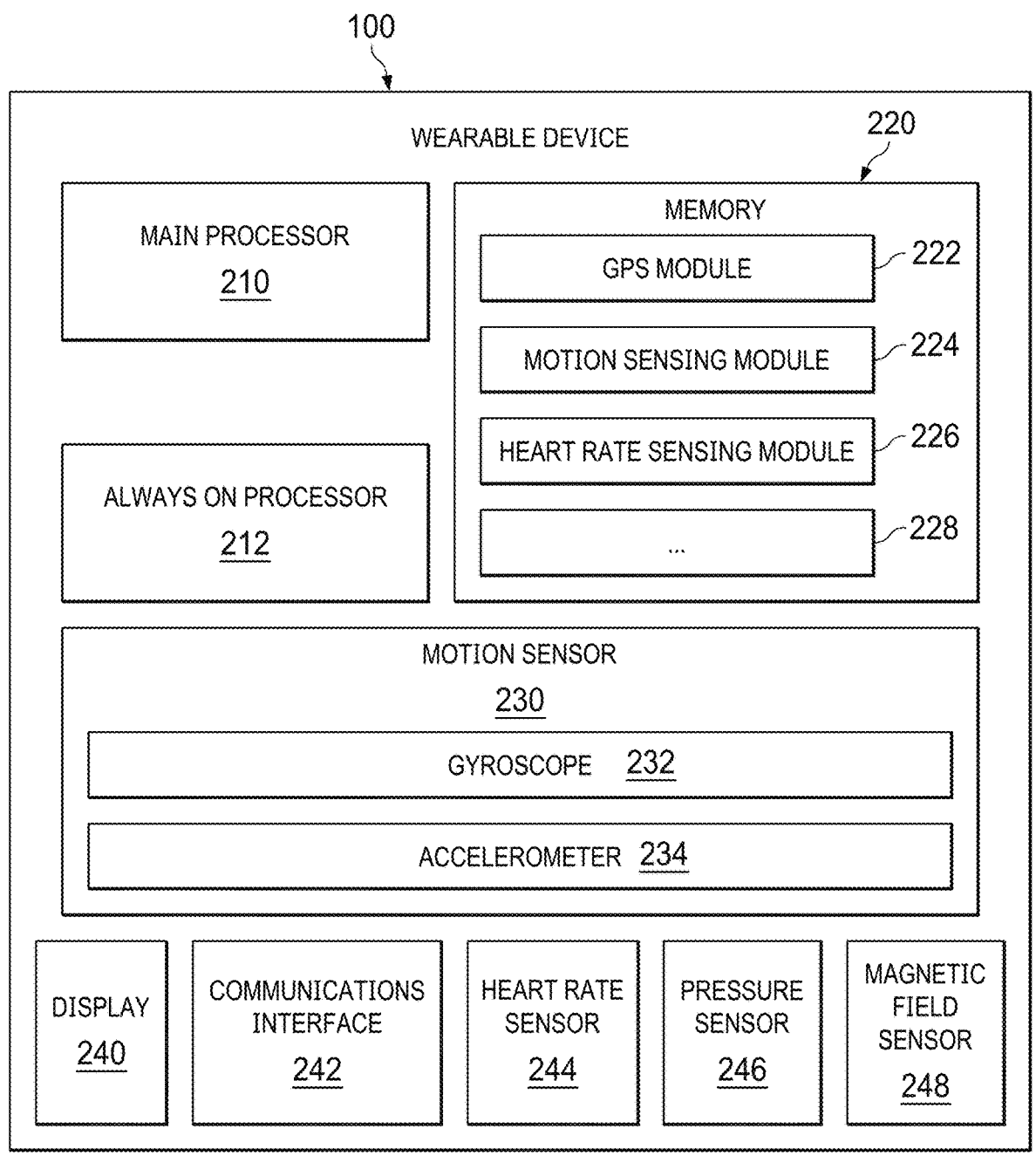
FIG. 2 is a block diagram showing exemplary components that may be found within a wearable device, according to embodiments of the disclosure.

FIG. 2 depicts a block diagram of exemplary components that may be found within the wearable device 100 according to some embodiments of the present disclosure. In some embodiments, the wearable device 100 can include a main processor 210 (or "application processor" or "AP"), an always on processor 212 (or "AOP" or "motion co-processor"), a memory 220, one or more motion sensors 230, a display 240, an interface 242, a heart rate sensor 244, and a pressure sensor 246, and a magnetic field sensor 248. The wearable device 100 may include additional modules, fewer modules, or any other suitable combination of modules that perform any suitable operation or combination of operations.

In some embodiments, main processor 210 can include one or more cores and can accommodate one or more threads to run various applications and modules. Software can run on main processor 210 capable of executing computer instructions or computer code. The main processor 210 can also be implemented in hardware using an application specific integrated circuit (ASIC), programmable logic array (PLA), field programmable gate array (FPGA), or any other integrated circuit.

In some embodiments, wearable device 100 can also include an always on processor 212 which may draw less power than the main processor 210. Whereas the main processor 210 may be configured for general purpose computations and communications, the always on processor 212 may be configured to perform a relatively limited set of tasks, such as receiving and processing data from motion sensor 230, heart rate sensor 244, pressure sensor 246, and other modules within the wearable device 100. In many embodiments, the main processor 210 may be powered down at certain times to conserve battery charge, while the always on processor 212 remains powered on. Always on processor 212 may control when the main processor 210 is powered on or off.

Memory 220 can be a non-transitory computer readable medium, flash memory, a magnetic disk drive, an optical drive, a programmable read-only memory (PROM), a read-only memory (ROM), or any other memory or combination of memories. Memory 220 can include one or more modules 222-228.

The main processor 210 and/or always on processor 212 can be configured to run one or more modules 222-228 stored in memory 220 that are configured to cause main processor 210 or always on processor 212 to perform various steps that are discussed throughout the present disclosure.

In some embodiments, the wearable device 100 can include one or more motion sensors 230. For example, motion sensors 230 can include a gyroscope 232 and an accelerometer 234. In some embodiments, accelerometer 234 may be a three-axis accelerometer that measures linear acceleration in up to three-dimensions (for example, x-axis, y-axis, and z-axis). In some embodiments, gyroscope 232 may be a three-axis gyroscope that measures rotational data, such as rotational movement and/or angular velocity, in up to three-dimensions (for example, yaw, pitch, and roll). In some embodiments, accelerometer 234 may be a microelectromechanical system (MEMS) accelerometer, and gyroscope 232 may be an MEMS gyroscope. Main processor 210 or always on processor 212 of wearable device 100 may receive motion information from one or more motion sensors 230 to track acceleration, rotation, position, or orientation information of wearable device 100 in six degrees of freedom through three-dimensional space.

In some embodiments, the wearable device 100 may include other types of sensors in addition to accelerometer 234 and gyroscope 232. For example, the wearable device 100 may include a pressure sensor 246 (e.g., an altimeter, barometer, and the like), a magnetic field sensor 248 (e.g., a magnetometer, compass, and the like) and/or a location sensor (e.g., a Global Positioning System (GPS) sensor).

The wearable device 100 may also include a display 240. The display 240 may be a screen, such as a crystalline (e.g., sapphire) or glass touchscreen, configured to provide output to the user as well as receive input from the user via touch. For example, the display 240 may be configured to display a current heart rate or daily average energy expenditure. The display 240 may receive input from the user to select, for example, which information should be displayed, or whether the user is beginning a physical activity (e.g., starting a session) or ending a physical activity (e.g., ending a session), such as a cardio machine session, a swimming session, a running session, or a cycling session. In some embodiments, wearable device 100 may present output to the user in other ways, such as by producing sound with a speaker, and wearable device 100 may receive input from the user in other ways, such as by receiving voice commands via a microphone.

In various embodiments, wearable device 100 may communicate with external devices via an interface 242, including a configuration to present output to a user or receive input from a user. The interface 242 may be a wireless interface. The wireless interface may be a standard Bluetooth® (IEEE 802.15) interface, such as Bluetooth® v4.0, also known as "Bluetooth low energy." In various embodiments, the interface may operate according to a cellphone network protocol such as Long Term Evolution (LTE™) or a Wi-Fi (IEEE 802.11) protocol. In various embodiments, the interface 242 may include wired interfaces, such as a headphone jack or bus connector (e.g., Lightning®, Thunderbolt™, USB, etc.).

Wearable device 100 can measure an individual's current heart rate from a heart rate sensor 244. The heart rate sensor 244 may also be configured to determine a confidence level indicating a relative likelihood of an accuracy of a given heart rate measurement. In various embodiments, a traditional heart rate monitor may be used and may communicate with wearable device 100 through a near field communication method (e.g., Bluetooth).

In various embodiments, the wearable device 100 can include a photoplethysmogram (PPG) sensor. PPG is a technique for measuring a person's heart rate by optically measuring changes in the person's blood flow at a specific location. PPG can be implemented in many different types of devices in various forms and shapes. For example, a PPG sensor can be implemented in a wearable device 100 in the form of a wrist strap, which a user can wear around the wrist. A PPG sensor may also be implemented on the underside of a wearable device 100. The PPG sensor can optically measure the blood flow at the wrist. Based on the blood flow information, the wearable device 100 can derive the person's heart rate.

The wearable device 100 may be configured to communicate with a companion device, such as a smartphone. In various embodiments, wearable device 100 may be configured to communicate with other external devices, such as a notebook or desktop computer, tablet, headphones, Bluetooth headset, etc.

The modules described above are examples, and embodiments of wearable device 100 may include other modules not shown. For example, some embodiments of wearable device 100 may include a rechargeable battery (e.g., a lithium-ion battery), a microphone array, one or more cameras, two or more speakers, a watchband, water-resistant casing or coating, etc. In some embodiments, all modules within wearable device 100 can be electrically and/or mechanically coupled together. In some embodiments, main processor 210 and or always on processor 212 can coordinate the communication among each module.

In various embodiments, the wearable device 100 may use sensed and collected motion information to predict a user's activity. Examples of activities may include, but are not limited to cardio machine activities, walking, running, cycling, swimming, skiing, etc. Wearable device 100 may also be able to predict or otherwise detect when a user is stationary (e.g., sleeping, sitting, standing still, driving or otherwise controlling a vehicle, etc.). Wearable device 100 may use a variety of motion data and/or orientation data to predict a user's activity.

Wearable device 100 may use a variety of heuristics, algorithms, or other techniques to predict the user's activity and/or detect activity start and end points. In various embodiments, one or more machine learning techniques and/or predictive models trained on a large volume of data to predict the user's activity and/or detect activity end points.

Figure 3:
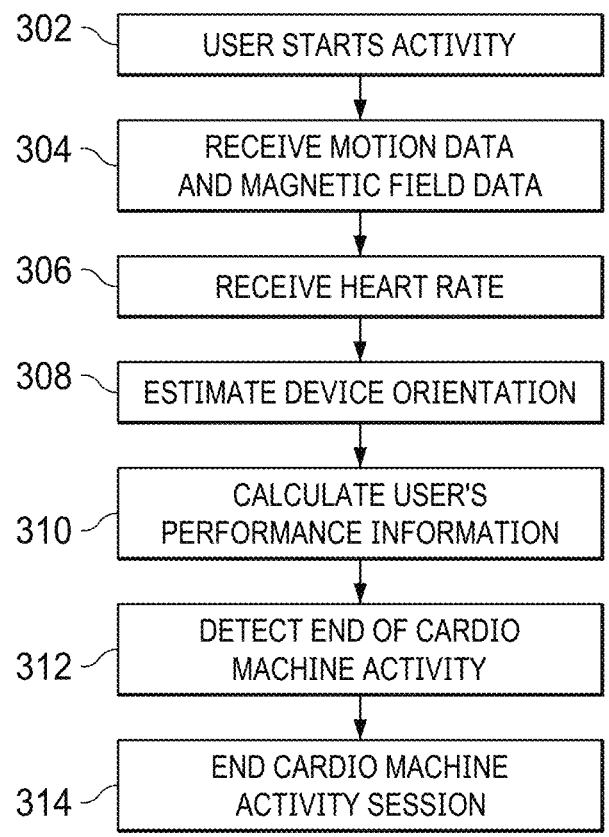
FIG. 3 is a flow chart illustrating a method for detecting the end of a cardio machine activity, according to embodiments of the disclosure.

FIG. 3 shows an exemplary method for tracking the performance of a user during a cardio machine activity. At step 302, a user starts a cardio machine activity. At step 304 motion data of the user is received, for example, from motion sensor of the wearable device shown in FIG. 2. The motion data may include accelerometer or gyroscope data according to some embodiments. At step 304, magnetic field data may also be received, for example, form a magnetic field sensor. In various embodiments, magnetic field data may indicate the position of the wearable device relative to a magnetic field (e.g., absolute north, a local magnetic field, and the like). At step 306, heart rate data of the user is received, for example, from the heart rate sensor of the wearable device shown in FIG. 2.

At step 308 orientation of the wearable device is estimated, for example, from the magnetic field data and motion data received from the magnetic field sensor and motion sensors of the wearable device shown in FIG. 2 The device orientation may be determined based on rotational data. For example, the rotational data may include one or more angles describing a position of the wearable device relative to an axis of rotation (e.g., yaw, pitch, and roll). In various embodiments rotational data may be generated using 6 or 9 axis sensor fusion. Rotational data generated from the 6 or 9 axis sensor fusion approach may be determined based on motion data measured by the gyroscope and accelerometer. The rotational data may be used to determine a position/angle of the wearable device in a three dimensional (3D) space relative to an axis of rotation (e.g., yaw, pitch, and roll). Rotational data determined from motion data captured by the gyroscope and accelerometer may include 6 rotational datapoints—3 from the motion data captured by the gyroscope and 3 form motion data captured by the accelerometer. The 6 rotational datapoints may then be combined to determine the orientation of the wearable device. For example, the angular position generated based on the angular acceleration and the angular position generated based on the angular velocity for each axis of rotation may be averaged to obtain an angular position of the wearable device in 3D space. The device orientation may then be determined based on the angular position relative each rotational axis included in the rotational data. The device orientation may describe the position of the wearable device relative to a frame of reference (e.g., a fixed component on the wearable device or gravity). In the 6 axis sensor fusion approach, 6 pieces of rotational data may be obtained at every time point in which the position of the wearable device is tracked (i.e., every second, in real time (i.e., fractions of a second), or any other time period). By tracking and comparing the changes in device orientation over time, a relative heading of the wearable device describing changes in the device orientation may be determined.

Rotational data determined using 9 axis sensor fusion may improve the accuracy of the rotational data estimated using the 6 axis sensor fusion approach. For example, the 9 axis sensor fusion approach may supplement rotational data determined from 6 axes of motion data with additional data points based on magnetic field data. In various embodiments, magnetic field data captured by the magnetic field sensor may be used to generate rotational data including a position/angle of the wearable device in 3D space relative to an axis of rotation (e.g., yaw, pitch, and roll), thereby generating 3 additional rotational data points. The 3 magnetic field based rotational datapoints may be combined with 6 datapoints generated from the motion data to more accurately determine the orientation of the wearable device. For example, the angular position based on the magnetic field sensor may be averaged with the angular position derived from angular velocity and the angular position derived from angular acceleration for each axis of rotation to obtain a more accurate angular position included in rotational data. The device orientation may then be calculated based on the angular positions at each axis of rotation. In the 9 axis sensor fusion approach, 9 pieces of rotational data may be determined at each point in time the position of the wearable device is tracked (i.e., every second, in real time (i.e., fractions of a second), or any other time period).

In various embodiments, the additional rotational datapoints based on magnetic field data can improve device orientation accuracy by normalizing for integration drift and other errors that are commonly included in rotational data generated based on motion data. For example, the angular position or the angular velocity of the wearable device may be obtained based on the angular acceleration component of motion data by integrating the angular acceleration over time. Similarly, the angular position of the wearable device can be obtained based on the angular velocity by integrating the angular velocity over time. Therefore, generating rotational data based on motion data (i.e., angular acceleration and angular velocity) may require double integration of angular acceleration values and single integration of angular velocity values. Due to integration drift, rotational data based on angular acceleration and or angular velocity may be accurate for only relatively short time intervals (e.g., 30 seconds). The device orientation may be continuously tracked throughout a user's entire workout session (i.e., several minutes and or hours). Therefore, integration drift may diminish the accuracy of device orientation, device headings, relative heading, and other device position tracking estimates made throughout the duration of a full workout activity. By including datapoints based on magnetic field data in rotational data used to generate the device position tracking estimates, the device position tracking estimates may be more accurate and consistent throughout the full workout activity. The performance of the motion sensors included in the wearable device may also not be uniform across all device instances. Motion sensor calibration may be disturbed by significant shock events causing some motion sensors to have better calibration than others and some motion sensors to exhibit more drift in motion data.

Rotational data generated based on magnetic field data may compensate for some of these common errors in rotational data derived from motion data. Magnetic field data describes the position of the wearable device relative to a steady state magnetic field near the device. The steady state magnetic field may be, for example, the earth's geomagnetic field, an ambient magnetic field generated by a cardio machine or other aspects of the environment local to the wearable device, and the like. Determining rotational data based on magnetic field data does not require an integration operation. Thus, including datapoints derived from magnetic field data in rotational data an reduce the impact of integration drift. Accordingly, noise in rotational data based on motion data attributable to integration drift and inconsistent performance of motion sensors may be normalized by including rotational datapoints based on magnetic field data. Similarly, noise in rotational data based on magnetic field data caused by, for example, a transient magnetic field generated by a mobile device passing in close proximity to the wearable device, may be normalized by rotational data derived from motion data. Therefore, using motion data and magnetic field data to generate orientation data, heading estimates, and other wearable device position tracking estimates, improves the precision, accuracy, and reliability of the device position tracking estimates generated by the wearable device.

The wearable device may calculate various performance information of the user during the cardio machine activity, at step 310. In various embodiments, performance information may include a user exertion level, stroke rate (e.g., rowing stroke rate, pedaling stroke rate, and the like), work rate, energy expenditure rate, heart rate, average heart rate, total machine time, calories burned, and the like. At step 310, performance information calculated by the wearable device may calculated from motion data, rotational data, device orientations, and/or heart rate data. Performance information may be output to a user, for example, rendered on a wearable device display (e.g., a crystalline or glass touchscreen) in real time during the cardio machine activity.

At step 312, a wearable device may detect the end of a cardio machine activity based on one or more primary indicators extracted from motion data, rotational data, device orientations, and/or heart rate data. In various embodiments, the wearable device may confirm the end of a cardio machine activity based one or more secondary indicators included in motion data, rotational data, device orientations, and/or heart rate data. FIGS. 6-20 below describe how a wearable device determines an ending point for different types of cardio machine activities in more detail. At step 314, once a wearable device detects the end of a cardio machine activity, it may end a cardio machine activity. In various embodiments, the wearable device may send a confirmation request to a user to confirm the end of the cardio machine activity. The confirmation request may be sent as a push notification to user and may be rendered by the wearable device on a display. The confirmation request may be in the form of a graphical user interface (GUI) that includes an input (e.g., button, selection, slider, free form text box, and the like) that allows the user to submit a response to the confirmation request (e.g., "Have you completed your cardio machine workout?").

After detecting the end of a cardio machine activity and/or receiving confirmation from the user that the cardio machine activity is over, the wearable device may stop calculating performance information and/or may aggregate performance information calculated during the cardio machine activity into cardio machine session dataset. The data included in the cardio machine session dataset may be rendered by the wearable device on a display as a GUI that includes performance information for the most recently recorded cardio machine session, performance information for previously recorded cardio machine sessions, and or performance tends over time.

FIGS. 4-5 illustrate exemplary processes that can be used to determine indicators of the end of a cardio machine activity. In various embodiments, the wearable device may determine the end of a cardio machine activity performed by a user based on one or more primary and/or secondary indicators. Primary and/or secondary indicators may be included in motion data, heart rate data, and device headings obtained during a cardio machine activity. Primary and/or secondary indicators may be specific to a particular type of cardio machine and may be stored in a cardio machine profile for a particular machine type. The cardio machine profile may include a level of exertion particular to a cardio machine and a motion model for each type of cardio machine activity. The motion model may include one or more motion features included in device heading data and/or one or more motion features found in motion data. The level of exertion and or motion features included in the cardio machine profile may be obtained by surveying a plurality of datasets including motion data and heart rate data collected during an activity including movements performed on a known type of cardio machine.

For example, the rowing cardio machine motion profile may include a high level of exertion, a constrained direction motion feature included in device headings, and a rowing stroke motion included in motion data as indicators of a rowing activity. The rowing stroke motion may be always observable during the rowing machine activity and may occur at regular intervals, wherein each stroke motion interval includes a pull phase characterized by a user pulling on a rowing apparatus and simultaneously extending their legs and torso and a compression phase characterized by a user relaxing on the rowing apparatus and simultaneously bending their legs and torso. Details of the profiles for the stair stepper, treadmill/elliptical machine, and the indoor cycling machine are described below in FIGS. 9-20. FIG. 4 describes an exemplary method for determining a level of exertion for a user that may be compared to a level of exertion threshold included in a cardio machine profile. FIG. 5 describes an exemplary method for detecting device heading and motion data based motion features included in a motion model for a cardio machine activity.

FIG. 4 illustrates an exemplary method for calculating a user level of exertion that can be used to detect the type of cardio machine activity performed by the user. At step 402, the wearable device receives user characteristics from a user profile available on the wearable device and/or a remote computer server connected to the wearable device. User characteristics may include age, maximum oxygen consumption, level of fitness, previous performance information, historical heart rate data, current heart rate data, heart rate data during a particular activity, heart rate data of other users having similar user characteristics, and the like. At step 404, the wearable device may estimate a user fitness level based on one or more of the user characteristics. The user fitness level may include expected heart rate information for the user while performing a variety of activities including different types of cardio machine activities (e.g., rowing on a rowing machine, running on a treadmill, stepping on a stair stepper, and the like).

The resting heart rate of the user during a specific activity may be estimated at step 406. The resting hear rate of the user may be determined based on a user specific heart rate prediction model generated by surveying a plurality of datasets including heart rate data measured during an activity performed by the user and or a group of having one or more characteristics (e.g., age, gender, weight, fitness level, and the like) in common with the user. The plurality of datasets may be analyzed using a variety of heuristics, algorithms, or other techniques to generate the user specific heart rate prediction model. The resting heart rate of the user may also be generated using one or more machine learning models trained on the plurality of datasets including heart rate data. In various embodiments, the plurality of datasets including heart rate data may include heart rate data measured for the user, similar users, dissimilar users, and/or unclassified users during known cardio machine activities, known non-cardio machine activities, cardio machine activities performed on a known type of cardio machine, and/or during unclassified activities. At step 408, the current measured user heart rate is obtained from a heart rate sensor of the wearable device. At step 409, the wearable may estimate an average of heart rate measurements observed during the workout.

At step 410, the current measured user heart rate, the estimated resting rate for the user, and a history of heart rates observed during the activity (e.g., the measured average user heart rate during the workout), may be input into an exertion model. In various embodiments, the exertion model may be specific to the user and/or a type of cardio machine activity. At step 412, the exertion model determines a user level of exertion based on the resting heart rate, the current heart rate measured for the user, and a history of heart rates observed during the activity. The user level of exertion output by the exertion model may seek to predict the user's level of exertion during the cardio machine activity. The exertion model may include a plurality of features for predicting the user's level of exertion. The plurality of features included in the exertion model may be obtained by surveying a plurality of datasets including heart rate data collected during an activity having a known level of exertion and or performed on a known type of cardio machine. The activities included in the plurality of datasets may be performed by the user and or a plurality of users having one or more characteristics in common with the user. Over time, the exertion model may be tuned to be more accurate and or specific to the user and/or cardio machine activity by modifying the plurality of features and or adding new features to the exertion model. The modified and or new features may be obtained by surveying a plurality of datasets including heart rate data collected during activities having a known level of exertion, a predicted level of exertion, and or a known cardio machine activity type. For example, one or more features of the exertion model may be adjusted (i.e., re-weighted) and or one or more new features added to correct for in-accurate level of exertion predictions. The features of the exertion model may also be adjusted and or revised in response to changes in the user's fitness level.

FIG. 5 illustrates an exemplary method of detecting motion features performed by a user during a cardio machine activity. At step 502, magnetic field data is received from a magnetic field sensor. At step 504, motion data is obtained from a motion sensor. At step 506, magnetic field data and motion data are input into a heading model. At step 508, the heading model estimates a device heading based on rotational data, for example, the rotational data generated using the 6 axis and or 9 axis sensor fusion described above.

To determine a user heading, the wearable device may project the three dimensional (3D) rotational data discussed below in connection with FIGS. 23A-25E into a two dimensional (2D) vector. The 2D vector may then be filtered to reduce noise. For example, the three dimensional rotational data collected using the 6 axis and or 9 axis approach is a 3D vector that moves in time and can be represented as i(t)=(x(t), y(t), z(t)). Then, in some embodiments, i(t) can be projected onto the x-y plane using the gravity vector, and the resulting 2D vector can be represented as j(t)=(x(t), y(t)). The x-component and y-component of j(t) may each individually filtered by a low-pass filter. The heading calculated for the user (i.e., user heading) corresponds to the angle between j(t) (i.e., the 2D rotational motion vector). To detect changes in the user's direction, the relative heading may be plotted to show the user's heading at multiple time points during the cardio machine activity. The change in the user's heading may then be calculated at adjacent times to show how j(t) is progressing in time. For example, suppose at t=0, (x=1, y=0), and then at t=1, (x=0, y=1), then the angle change (i.e., the change in heading) would be 90 degrees.

Figure 7:
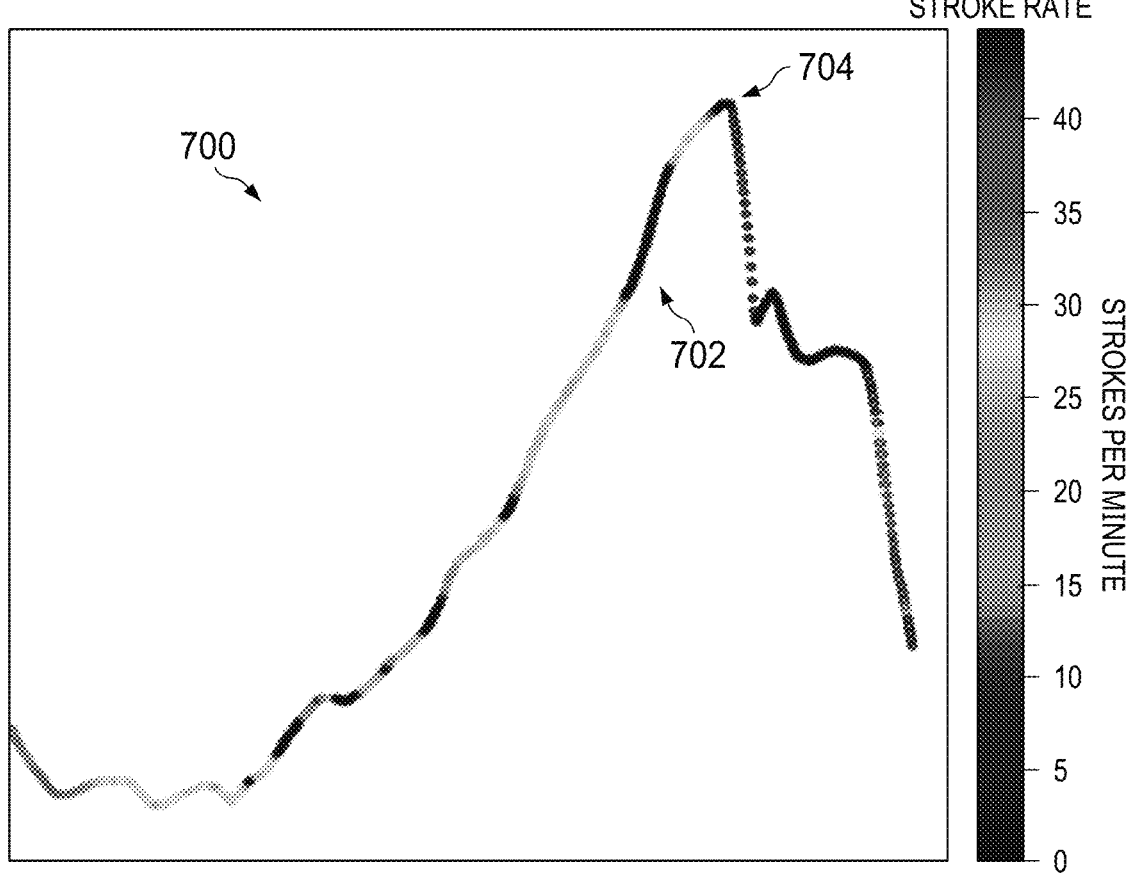
FIGS. 7-8 are graphs showing exemplary heading and stroke rate data used to detect the end of a rowing machine activity, according to embodiments of the disclosure.
Figure 10:
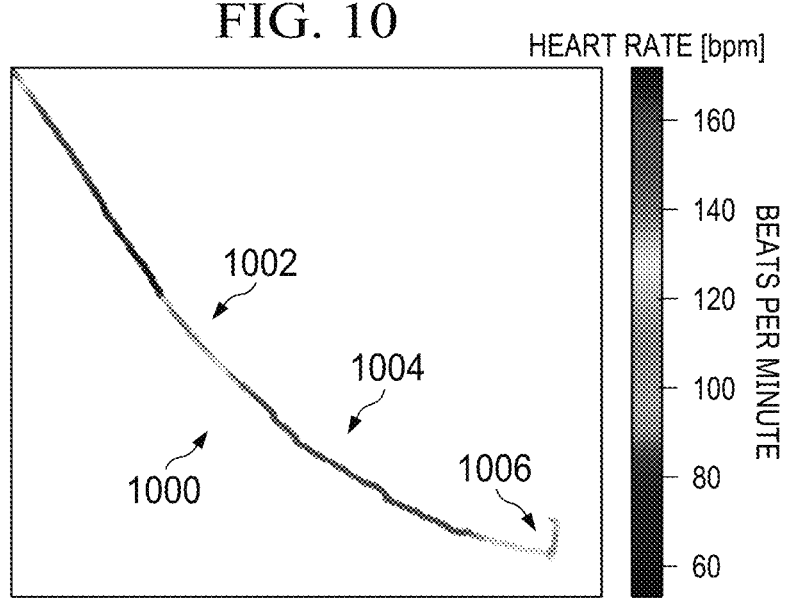
FIGS. 10-12 are graphs showing exemplary heading, heart rate, and step cadence data used to detect the end of a stair stepper activity, according to embodiments of the disclosure.
Figure 18:
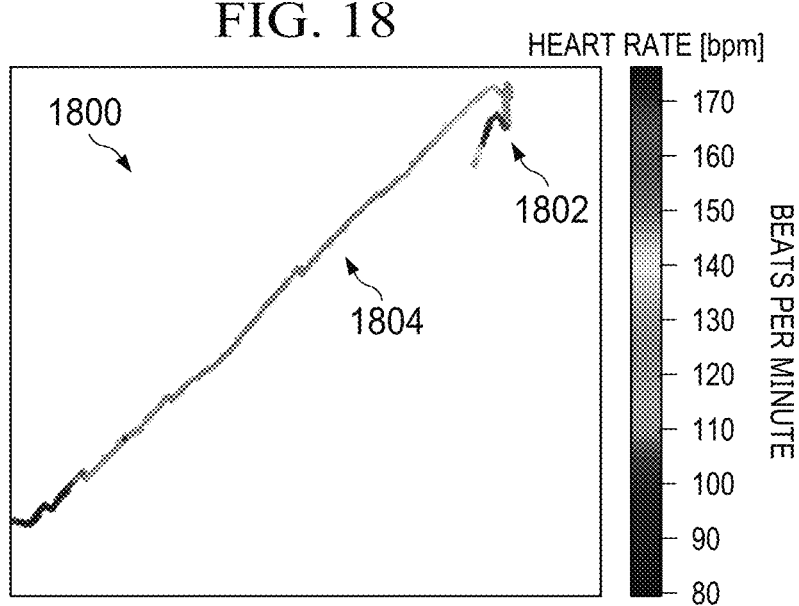
FIGS. 18-20 are graphs showing exemplary heading, heart rate and step count data used to detect the end of an indoor cycling activity, according to embodiments of the disclosure.

FIGS. 7, 10, and 18 below show a plot of the heading line derived from the 2D rotational motion vector generated during the activity. As shown in FIG. 7, the direction of the heading line 702 remains constant during the activity as indicated by little change (i.e., less than 90 degrees) in the slope of the heading line 702 during the activity. The large change (i.e., greater than 90 degrees) in the slope of the heading line 702 observed at the variable heading point indicates a significant change in user heading and suggests the activity has ended. To determine if change in relative heading is sufficient to detect and or confirm the end of an activity, the change in relative heading may be compared to a relative heading threshold (e.g., 90 degrees to 140 degrees). If the change in relative heading exceeds the relative heading threshold, the wearable device may determine the activity is over. If the change in relative heading does not exceed the relative heading threshold, the wearable device may determine the activity is still ongoing. The magnitude of the relative heading threshold may be determined by surveying a plurality of datasets including rotational data, device headings, and or relative heading measurements obtained during activities having known beginning and ending points.

In various embodiments, the device heading may also be determined by algorithmically combining accelerometer measurements with gyroscope measurements to provide a smoothed estimate of the relative orientation of the wearable device in an inertial frame. In various embodiments, rotational data may include the angle/position of the wearable device in 3D space relative to a reference frame (e.g., a fixed body reference frame, and inertial reference frame, and the like.). For example, rotational data may include rotational angles (i.e., angular positions) in 3D space (e.g., roll, pitch, and yaw) that describe the position of the wearable device as well as angular acceleration and angular velocity measurements describing the rate of change between two or more angular positions. Motion data collected from one or more motions sensors (e.g., an accelerometer and gyroscope) may be used to generate rotational data including 3 rotational angles derived from accelerometer data and 3 rotational angles derived from gyroscope data. A device orientation data may be calculated based on the rotational data using 6 axis sensor fusion approach described above. In various embodiments, device heading may be calculated from the yaw component (e.g., rotational angle relative to the x axis or horizontal plane) of the rotational data.

At step 508, the heading model may estimate a relative heading of the wearable device by determining the difference in device heading at multiple points during the cardio machine activity. The heading model may also estimate relative heading of the wearable device by calculating the difference between the yaw component of the rotational data of the wearable device at multiple points during the activity. For example, the heading model may calculate relative heading by computing the angle of rotation of a body-fixed reference (e.g., the crown or another component fixed to the surface of the wearable device) relative to wearable device's local horizontal plane at two time points. The difference between angle of rotation relative to the wearable's local horizontal plane at the two time points may calculated to determine the relative heading of the wearable device. In some embodiments, the relative heading may be determined continuously throughout the activity to accurately track the changes in the position of the wearable device.

Magnetic field data may be used to improve the accuracy of device headings by providing additional rotational datapoints of the wearable device in 3D space that may be combined with the rotational data determined based on motion data. For example, an angle of rotation of a fixed body reference in the horizontal plane local to the wearable device may be calculated using rotational data (e.g., rotational angles in 3D space) generated from magnetic field data. The horizontal angle of rotation generated from magnetic field data may then be algorithmically combined with the horizontal angle of rotation generated from motion data (e.g., gyroscope and accelerometer data) to improve accuracy of device headings. By incorporating rotational data determined based on magnetic field data into device heading calculations, the magnetic field data may be used to improve the accuracy of the relative heading estimate generated by the heading model. In various embodiments, magnetic field data may also be used to compute an absolute device heading relative to true north. The absolute device heading may be used to determine and or augment the device heading.

The heading model may be specific to the wearable device, the user, and/or a type of cardio machine activity. For example, the heading model may include one or more features used to determine the device heading for a particular user and or type of cardio machine activity. The features included in the heading model may be determined by surveying a plurality of datasets including rotational data collected during activities having multiple known device headings. The device heading output by the heading model may be used to predict the direction of the travel of the user during the cardio machine activity. Over time, the heading model may be tuned to be more accurately determine the device heading. In various embodiments the heading model may be tuned by adjusting one or more of the heading model features and or adding new features. Features may be adjusted and or added based on a plurality of datasets including rotational data collected during activities having multiple known device headings and device heading predictions generated by the heading model. For example, the heading model may be tuned by adjusting (e.g., changing the weights) one or more model features to correct for in-accurate heading values determined by the heading model and/or changes in the calibration of one or more sensors of the wearable device. In various embodiments, the rotational data included in the plurality of datasets may be measured by the wearable device, similar wearable devices, dissimilar wearable devices, and/or unclassified wearable devices during known cardio machine activities, known non-cardio machine activities, and/or during unclassified activities. The rotational data included in the plurality of datasets may be used to determine device headings. Alternatively, the plurality of datasets may include known correct heading values, known incorrect heading values, and/or unlabeled heading values generated that were previously calculated from the activities included in the plurality of datasets.

At step 510, motion data and the device heading are input into a cardio machine motion model. In various embodiments, the motion model may detect a particular cardio machine activity type by comparing the motion data and/or device headings obtained during a cardio machine activity to one or more motion features and a device heading threshold included in the cardio machine profile for each cardio machine. The motion model for each cardio machine activity type may include one or more motion features and or a device heading threshold that are specific to a cardio machine activity. The motion features and device heading threshold for a particular cardio machine activity may be determined by surveying a plurality of datasets including motion data, rotational data, and or device headings collected during known cardio machine activities. The activities included in the plurality of datasets may be performed on one or more particular cardio machines by the user and or a group of users having one or more characteristics in common with the user. The one or more motion features included in motion data and/or the device headings are then detected using the cardio machine activity motion model at step 512.

The motion features for each cardio machine activity type may correspond to particular patterns, heuristics, and/or signals included in motion data. For example, motion features for rowing machine activities may include a direction constrained device heading and/or rowing strokes occurring at regular intervals during the rowing machine activity. FIGS. 9-20 below describe the motion features for other cardio machine activities in more detail. In various embodiments, the cardio machine motion model is a global motion model generalizable to activities performed on many different types of cardio machines. Global motion models may detect a variety of cardio machine motion features (e.g., rowing motion features, elliptical motion features, treadmill motion features, cycling motion features, and the like). In various embodiments, the cardio machine motion model may be specific to a particular cardio machine. The particular cardio machine motion model to use during a cardio machine activity may be informed by a user selecting a type of cardio machine workout or confirming the type of cardio machine workout in response to a confirmation request sent to a user via a graphic user interface (GUI) displayed on a display surface of the wearable device. The wearable device may also automatically determine the cardio machine motion model to use based on motion data.

The cardio machine motion model may continuously compare the motion data and or device heading to the motion features and or the device heading threshold included in the motion model for a particular cardio machine activity to detect the performance of the one or more motion features and or changes in device heading that indicate the user is using the particular cardio machine. In various embodiments, one or more machine learning techniques and/or predictive models trained on a plurality of datasets including motion data, rotational data, and or device headings collected during known cardio machine activities may be used to determine the motion features and or device heading threshold to include in the motion models for a wide variety of cardio machines. The motion data included in the plurality of datasets may include motion data collected for a user, similar users, dissimilar users, and/or unclassified users during known cardio machine activities of a particular type, known cardio machine activities, known non-cardio machine activities, and or unclassified cardio-machine activities. The device headings included in the plurality of datasets may be generated by the wearable device, similar wearable devices, dissimilar wearable devices, and unclassified wearable devices during known cardio machine activities of a particular type, known cardio machine activities, known non-cardio machine activities, and unclassified cardio-machine activities. Over time, the motion models for each type of cardio machine activity may evolve to include more features, device heading thresholds, patterns, heuristics, and/or signals indicating the user is using a particular cardio machine.

Figure 6:
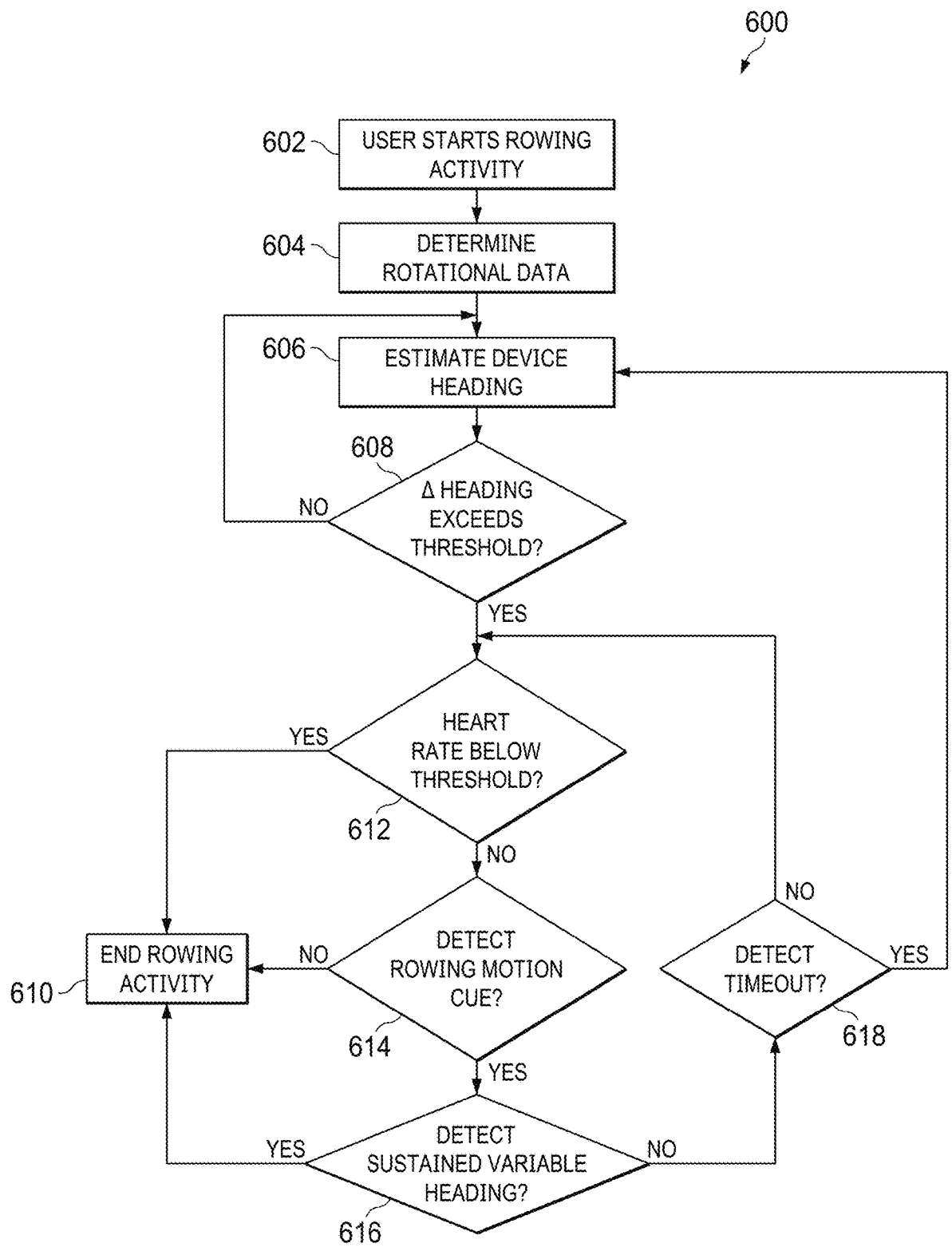
FIG. 6 is a flow chart illustrating a method for detecting an end of a rowing machine activity, according to embodiments of the disclosure.
Figure 8:
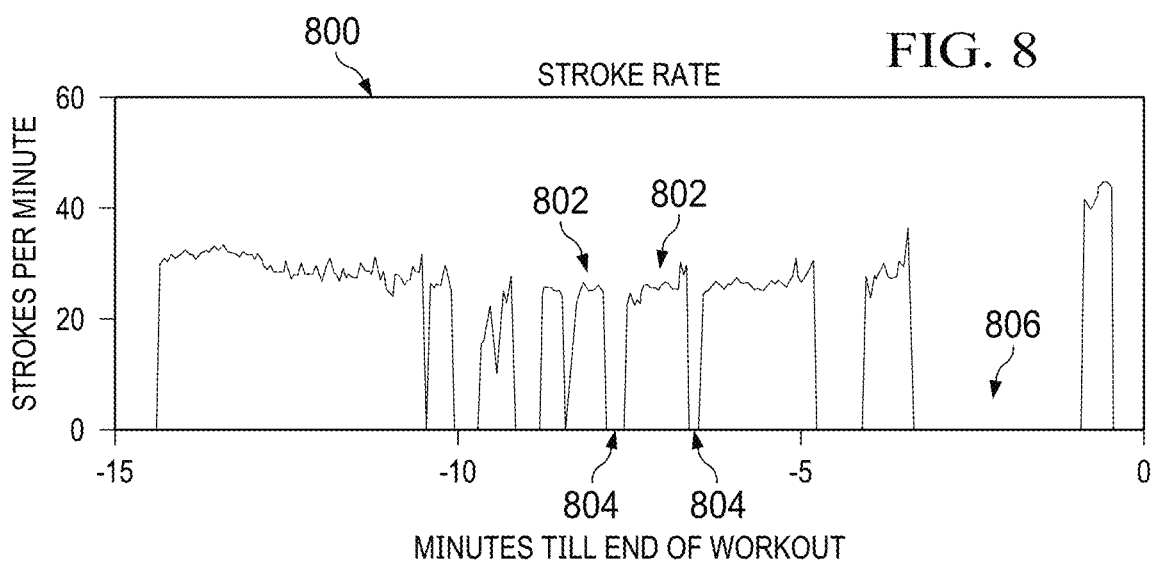

FIGS. 6-8 illustrate an exemplary process and exemplary features that may be used to detect the end of a rowing machine activity. FIG. 6 illustrates an exemplary process 600 for detecting the end of a rowing machine activity and FIGS. 7-8 illustrate two graphs displaying exemplary device heading and motion data collected during a rowing machine activity. Aspects of the data shown in FIGS. 7-8 are used to determine the end of a rowing machine activity using the process 600 illustrated in FIG. 6. In various embodiments, the device heading and motion data shown in FIGS. 7-8 may be analyzed by the wearable device to detect one or more motion features included in a rowing machine motion model. Motion features included in the rowing machine motion model may include rowing strokes observable during the rowing machine activity, intervals of rowing time and resting time, and device headings having a constrained direction of travel. Intervals of rowing time and resting time may show up in motion data as alternating periods of rowing and resting, with the user performing a rowing motion during the rowing periods and a user remaining stationary during the resting periods. Rowing strokes performed during the rowing machine activity may cause the device heading to indicate a constrained direction of travel, wherein the device heading consistently repeats the same pattern during the rowing activity and exceeds a device heading threshold on a periodic basis during the rowing activity.

As shown in FIG. 6, a user starts a rowing activity at step 602. Heart rate data measured by a heart rate sensor, motion data measured by one or more motion sensors, and magnetic field data measured by a magnetic field sensor may be recorded by the wearable device during the rowing activity. In various embodiments, the heart rate sensor can be a PPG sensor and the wearable device may receive and/or process heart rate data from the PPG sensor according to techniques described in U.S. patent application Ser. No. 15/692,736, filed on Aug. 31, 2017, and entitled "SYSTEMS AND METHODS FOR DETERMINING AN INTENSITY LEVEL OF AN EXERCISE USING PHOTOPLETHYSMOGRAM (PPG)," which patent application is incorporated herein in its entirety. The wearable device may compare the heart rate data received from the heart rate sensor to a resting heart rate threshold (e.g., 30-70 beats per minute (bpm)) to determine that the user is active. The resting heart rate threshold may depend on one or more characteristics of the user, for example, age, fitness level, level of fatigue, and the like. The user heart rate, average heart rate, and/or level of exertion for users performing rowing machine activities may be difficult to measure because clenching the rowing apparatus by the user can disturb the ability of the heart rate sensor to sense to blood flow of the user. If the user is performing intervals during the rowing machine activity, the user's heart rate may correspond to the intervals so that the user's heart rate/level of exertion is higher during the rowing periods and the user's heart rate/level of exertion is lower during the resting periods.

At step 604, motion data and/or magnetic field data may be used to determine rotational data. The rotational data may then be used to calculate the position (i.e., device orientation) of the wearable device. At step 606, device heading may be estimated from rotational data describing the angle/position of the wearable device in 3D space relative to a reference frame. To determine changes in user direction, the wearable device may track changes in rotational data and/or device heading during the activity to determine the relative device heading. For example, periodically during the rowing machine activity, the wearable device may estimate a relative device heading by calculating a heading difference (e.g., the difference between a current device heading and a device heading determined at a previous time point). Changes in the relative heading that exceed a predetermined heading threshold (e.g., 90 degrees) may be interpreted by the wearable device as changes in user direction.

In various embodiments, changes in device heading the exceed a predetermined heading threshold (e.g., changes of 90 degrees or more in the horizontal angle of rotation) may indicate a user has left a cardio machine. The greater the change in device heading (i.e., the higher the relative heading), the higher the confidence level that may be associated with a determination to end a cardio machine activity. If, at step 608, the relative heading exceeds the heading threshold, a primary indicator for the end of a rowing machine activity may be detected. In response, the wearable device may search for a secondary indicator of the end of a rowing activity end to confirm the user has ended the rowing machine activity. If, at step 608, the relative heading does not exceed a variable heading threshold, the wearable device may maintain the rowing machine activity and continue to estimate device heading. In various embodiments, motion features included in the rowing machine motion model may be detected in rotational data and or device headings estimated during the rowing machine activity. For example, a constrained direction of travel indicated by device headings that consistently follow the same pattern (i.e., periodically generate the same relative heading) and/or have very low relative heading values over an extended period of time may be included as a motion feature for rowing machine motion model.

In response to determining the relative heading exceeds a relative heading threshold, the wearable device may attempt to confirm the end of the rowing machine activity by searching for secondary indicator of the end of a rowing activity at steps 612-616. The secondary indicator of the end of a rowing activity may be included in heart rate data, motion data, rotational data, device orientations, and or device headings. For example, at step 612, the wearable device may determine if a user's current heart rate is below one or more heart rate thresholds (e.g., a resting heart rate threshold or a relative heart rate threshold, and the like). The wearable device may also use heart rate data to determine a level of exertion for the user and compare a current level of exertion to an exertion threshold. If the current heart rate/level of exertion is below a heart rate threshold/level of exertion threshold, the wearable device may end the rowing machine activity at step 610. If the current heart rate/level of exertion is not below a heart rate threshold/level of exertion threshold, the wearable device may search for a secondary indicator to confirm the end of a rowing machine activity in motion data and/or device headings.

In various embodiments, the wearable device may detect the end of a cardio machine activity using a relative heart rate. Relative heart rate may describe the difference between the current user heart rate and the average user heart rate during the activity session. To determine the user's relative heart rate, the wearable device calculates an average heart rate of the user during a cardio machine activity. The user device then determines the difference between the user's current heart rate and the average user heart rate to determine the relative heart rate. To confirm the end of a cardio machine activity, the wearable device may compare a relative heart rate to a relative heart rate threshold. If the relative heart rate threshold fails the relative heart rate threshold, the wearable device may end the rowing machine activity at step 610. In various embodiments, the wearable device may end the cardio machine activity upon determining the relative heart rate is below the relative heart rate threshold, below the resting heart rate threshold, and/or below the level of exertion fails the exertion threshold. The relative heart rate threshold may be specific to a particular type of cardio machine activity and/or generalizable across one or more distinct cardio machine activity types. The value for the relative heart rate threshold, the resting heart rate threshold, and or the exertion threshold may be determined by surveying a plurality of datasets including heart rate data collected during rowing activities before and after a known end of a rowing activity. The rowing activity included in the plurality of datasets may be performed by a particular user and or a group of users having one or more characteristics in common with the user.

At step 614, the wearable device may search motion data, rotational data, and/or device headings obtained during the rowing activity to detect one or more motion features included in a rowing motion model (e.g., rowing motion features). If the wearable device detects one or more rowing motion features, device headings may be further analyzed to detect a secondary indicator confirming the end of a rowing machine activity. If the wearable device does not detect one or more rowing motion features, the absence of rowing motion features in motion data, rotational data, and/or device headings generated by the user may be a secondary indicator confirming the end of a rowing activity, and a wearable device may end the rowing activity, at step 610.

At step 616, the wearable device may detect a sustained variable heading by detecting a series of direction changes within the device headings estimated during a defined period of time (e.g., 1 minute, 5 minutes, etc.). The device heading of a wearable device remains constant during a rowing machine activity because the user must be on the machine facing the same direction at all times during the rowing activity. Therefore, a period of sustained variable heading in which the device headings are not constant for a defined period of time or repeating during periodic intervals indicates a user is not performing a rowing machine activity and may be considered a secondary indicator of the end of a rowing activity. In response to detecting the secondary indicator in the device headings, the wearable device may end the rowing activity, at step 610. If device heading changes once during the rowing activity but does not continue to change, the user may be stationary after getting up from a rowing machine and/or may be stationary while still on the rowing machine. Therefore, if no sustained variable heading is detected, the wearable device may detect a device timeout, at step 618. If a device timeout is detected, the wearable device waits for the user to resume the rowing machine activity and calculates an estimate for device heading, at step 606 when activity is resumed. If a device timeout is not detected, the wearable device repeats steps 612-616 to detect a secondary indicator and confirm the end of the rowing activity.

FIGS. 7-8 illustrate exemplary device heading and stroke rate data 700 collected by the wearable device during a rowing activity. As shown in FIG. 7 the direction of the device heading shown by the heading line 702 remained constant throughout the rowing activity. The heading line 702 is analogous to the path a user would take through a room with straight lines with consistent slope indicating very little heading change and zig zagging lines or abrupt changes in the slope or direction of the heading line 702 indicating a variable heading. As shown in FIG. 7, the end of the rowing activity was indicated by the abrupt change in the direction of the heading line 702 at the variable heading point 704. The heading line 702 had a constant direction that was up and to the right until the variable heading point 704. At, the variable heading point 704, the heading line 702 changed direction and began moving down and to the right. The down and to the right direction of the heading line 702 was maintained for an extend period of time (e.g., at least 1 to 5 minutes) after the variable heading point 704 indicating a sustained change in heading. This sustained change in device heading may be a primary indicator of the end of a cardio machine activity.

As shown in FIG. 8, the stroke rate indicating the number of rowing strokes per minute the user performed during the rowing activity fluctuated at regular intervals between rowing periods having around 35 strokes per minute shown at the rowing points 802 and resting periods having 0 strokes per minute shown at the resting points 804. The sustained period of no-rowing strokes within the non-rowing region 806 corresponds with the end of the rowing machine activity and the absence of the rowing stroke motion feature may be a secondary indicator detected by the wearable device to confirm the end of the rowing machine activity. Stroke rate data shown in FIG. 8 is incorporated into the heading line 702 so that the color of the heading line 702 may reflect the stroke rate at that point in time during the rowing machine activity. As shown in FIG. 7, the heading line 702 may be shaded yellow and red when the stroke rate is elevated (e.g., above 25 strokes per minute) and the heading line 702 may be shaded green and blue when the stroke rate is reduced (e.g., below 25 strokes per minute).

Figure 9:
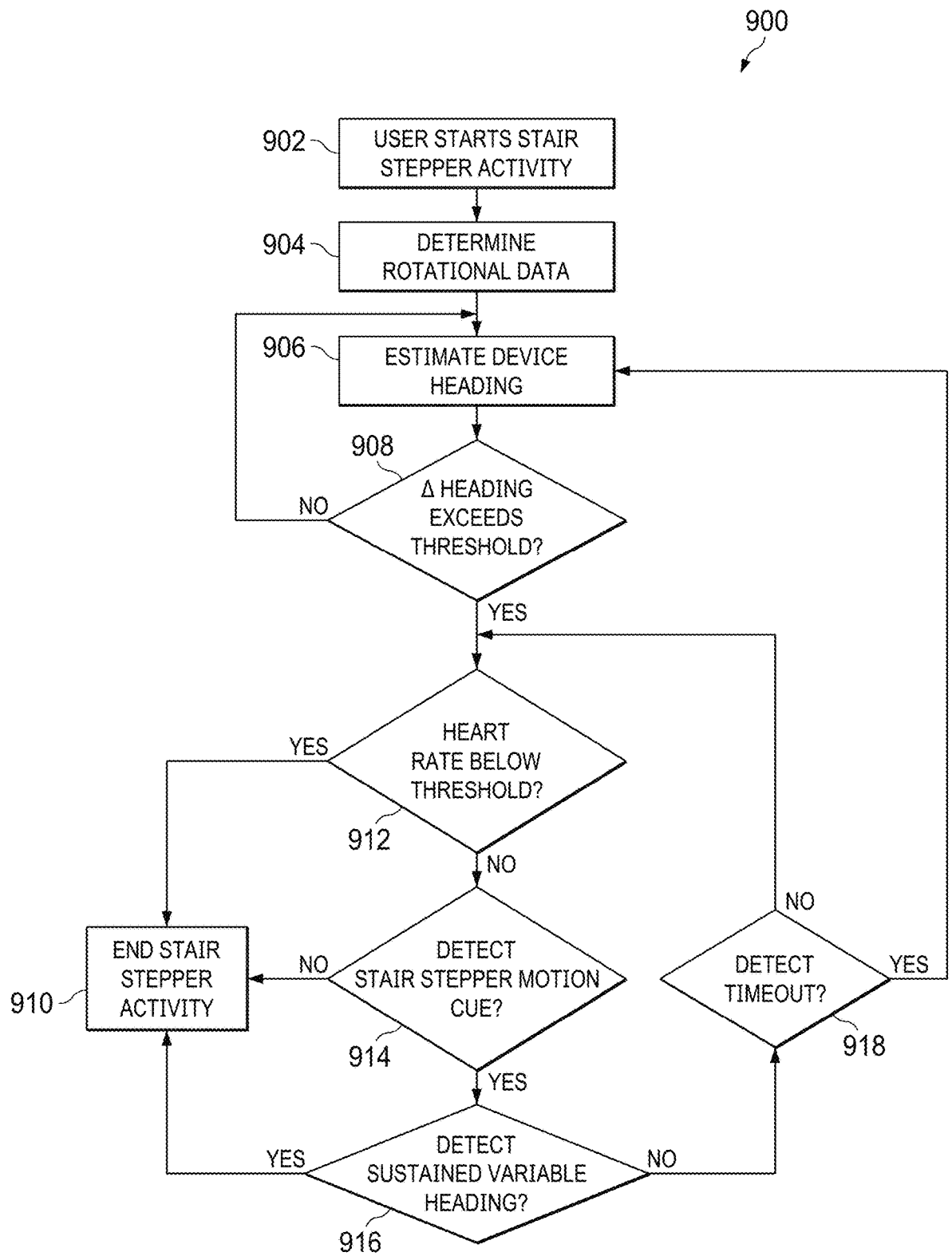
FIG. 9 is a flow chart illustrating a method for detecting an end of a stair stepper activity, according to embodiments of the disclosure.
Figure 11:
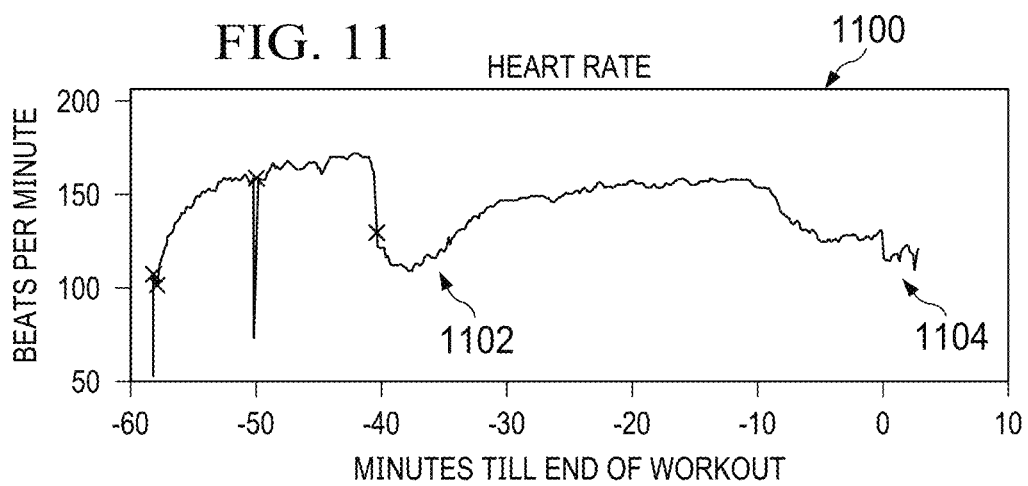
Figure 12:
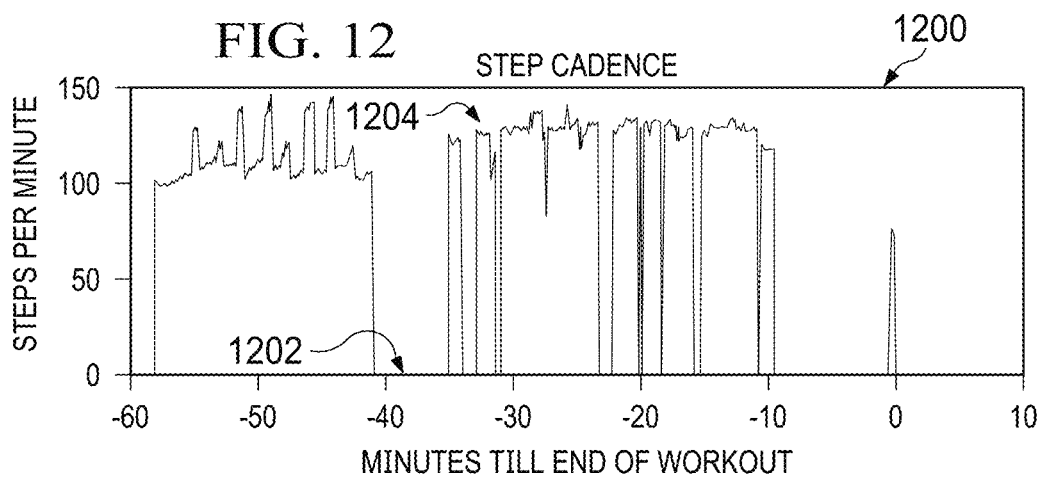

FIGS. 9-12 illustrate an exemplary process and exemplary features that may be used to detect the end of a stair stepper activity. FIG. 9 illustrates an exemplary process 900 for detecting the end of a stair stepper activity and FIGS. 10-12 illustrate three graphs displaying exemplary device headings, heart rate, and step cadence data collected during a stair stepper activity. Aspects of the data shown in FIGS. 10-12 are used by the process 900 illustrated in FIG. 9 to determine the end of a stair stepper activity. In various embodiments, device heading and motion data shown in FIGS. 10 and 12 may be analyzed by the wearable device to detect one or more motion features included in a motion model for a stair stepper machine. Motion features included in the motion model for a stair stepper machine may include steps and device headings that have subtle differences due to grip changes and/or periodic perpendicular heading changes caused by side stepping.

The stepping motion may be unobservable at certain points during the stair stepper activity when the user is holding onto the handrails of the machine and thereby keeping the wearable device stationary and the user's arm/wrist pose constant. When the user releases the handrails of the stair stepper machine, the wearable device may begin detecting the stepping motion by observing changes in the user's arm/wrist pose that are consistent with steps. Therefore, subtle changes in user hand position caused by the user grasping and/or releasing a handrail may correspond with the beginning and/or end of period of observable stepping motion. Grip changes while the user is holding the handrails and/or gripping or releasing the handrails may show up in device headings as subtle heading changes (e.g., small relative heading values) that may not exceed the heading threshold for stair stepper motion. During stair stepper activities, users may perform side steps and/or cross oversteps to climb stairs on a stair stepper machine. To perform side steps, users may turn perpendicularly from facing the front of the machine to facing the handrails at the side of the machine and climb stairs from this side facing position with the user's feet parallel to wider section of the stairs. Side stepping may show up in device headings as a perpendicular change of direction that may occurs periodically during a stair stepper activity.

In various embodiments, the motion profile for a stair stepper machine may include a plurality of motion features, a level of exertion threshold, and a heading threshold. The plurality of motion features, the level of exertion threshold, and the heading threshold for the stair stepper machine motion profile may be determined by surveying a plurality of datasets including motion data, heart rate data, rotational data, and or device headings collected during known stair stepper activities. For example, a stair stepper activity may have a high level of exertion threshold (e.g., above 10.0 metabolic equivalents (METs)) due to the aerobic intensity of the stair stepper activities included in the plurality of datasets. Stair stepper activities included in the plurality of datasets may be performed by a particular user and or a group of users having one or more characteristics in common with the particular user. Once one or more motion features and or a device heading that exceeds the heading threshold is detected as a primary indicator of the end of stair stepper activity, the wearable device may analyze the heart rate data to confirm the user has ended the stair stepper activity. For example, the wearable device may analyze the heart rate data shown in FIG. 11 to detect a secondary indicator of the end of a stair stepper activity by measuring a heart rate of the user that produces a level of exertion falling below the level of exertion threshold (e.g., below 10.0 METs) included in the motion profile for the stair stepper machine.

To detect the end of a stair stepper activity using the exemplary process 900 shown in FIG. 9, a user starts a stair stepper activity at step 902. Heart rate data measured by a heart rate sensor, motion data measured by one or more motion sensors, and magnetic field data measured by a magnetic field sensor may be recorded by the wearable device during the stair stepper activity. In various embodiments, the heart rate sensor can be a PPG sensor and the wearable device may receive and/or process heart rate data from the PPG sensor according to techniques described in U.S. patent application Ser. No. 15/692,736, filed on Aug. 31, 2017, and entitled "SYSTEMS AND METHODS FOR DETERMINING AN INTENSITY LEVEL OF AN EXERCISE USING PHOTOPLETHYSMOGRAM (PPG)," which patent application is incorporated herein in its entirety. The wearable device may compare the heart rate data received from the heart rate sensor to a resting heart rate threshold (e.g., 30-70 beats per minute (bpm)) to determine that the user is active. The resting heart rate threshold may depend on characteristics of the user including age, fitness level, level of fatigue, and the like and may be determined by surveying a plurality of datasets including heart rate data collected during activity sessions having a wide range of exertion levels. The activity sessions may be performed by the user and or a group of users having one or more characteristics in common with the user.

At step 904, rotational data may be determined from motion data and/or magnetic field data as described above. The rotational data may then be used to calculate the position (i.e., device orientation) of the wearable device. At step 906, device heading may be estimated from rotational data describing the angle/position of the wearable device in 3D space relative to a reference frame. To determine changes in user direction, the wearable device may track changes in rotational data and/or device heading during the activity session to determine a relative device heading. For example, continuously and or periodically during the stair stepper activity, the wearable device may estimate a relative device heading by calculating a heading difference (e.g., the difference between a current device heading and a device heading determined at a previous time point).

If, at step 908, the heading difference exceeds a predetermined heading threshold for the stair stepper activity, a primary indicator for the end of a stair stepper activity may be detected. While performing a stair stepper activity, the user is confined to the stair stepper machine and therefore generally travels in the same direction. Accordingly, the heading threshold for the stair stepper activity may correspond to large change (e.g., 140 degrees or more) in heading. In response to detecting a relative heading that exceeds the heading threshold, the wearable device may search for a secondary indicator of the end of a stair stepper activity to confirm the user has ended the stair stepper activity. If, at step 908, the heading difference does not exceed the heading threshold for the stair stepper activity, the wearable device may maintain the stair stepper activity and continue to estimate device heading. In various embodiments, the stair stepper motion model may include one or more motion features that may be detected in device headings. For example, perpendicular changes (i.e., shifts in device headings of approximately 90 degrees) in device heading may occur when a user turns perpendicularly to a side stepping position. Additionally, subtle changes (i.e., less than 20 degrees) in device heading may occur when a user adjusts her grip on the handrails and/or grips or releases a handrail. In some embodiments, a user may turn to a side stepping position by changing from a front facing position facing the front of the stair stepper machine to a side facing position facing the handrails at the side of the stair stepper.

At steps 912-916, the wearable device may attempt to confirm the end of the stair stepper activity by searching for a secondary indicator of the end of a stair stepper activity in heart rate data, motion data, and device headings. At step 912, the wearable device may determine that a user's current heart rate is below a heart rate threshold for a stair stepper activity (e.g., a resting heart rate threshold, relative heart rate threshold hold, an average heart rate threshold, and the like). The wearable device may also use heart rate data to determine a level of exertion for the user and compare a current level of exertion to a predetermined exertion threshold for the stair stepper activity. If the current heart rate/level of exertion is below a heart rate threshold/level of exertion threshold for the stair stepper activity, the wearable device ends the stair stepper activity at step 910. If the current heart rate/level of exertion is not below a heart rate threshold/level of exertion threshold for the stair stepper activity, the wearable device may search for a secondary indicator to confirm the end of a stair stepper activity in motion and/or orientation data.

In various embodiments, the wearable device may detect the end of a cardio machine activity using a relative heart rate. Relative heart rate may describe the difference between the current user heart rate and the average user heart rate during the activity session. To determine the user's relative heart rate, the wearable device calculates an average heart rate of the user during a cardio machine activity. The user device then computes the difference between the user's current heart rate and the average user heart rate to determine the relative heart rate. To confirm the end of a cardio machine activity, the wearable device may compare a relative heart rate to a relative heart rate threshold. If the relative heart rate does not exceed the relative heart rate threshold, the wearable device may end the stair stepper activity at step 910. The relative heart rate threshold may be determined by surveying a plurality of datasets including heart rate data and or relative heart rates collected during stair stepper activities. The activities may be performed by a particular user and or a group of users having one or more characteristics in common with the particular user. The relative heart rate threshold may be specific to a particular type of cardio machine activity and/or generalizable across one or more distinct cardio machine activity types. In summary, the wearable device may end the cardio machine activity upon determining the relative heart rate is below the relative heart rate threshold, determining the current heart rate is below the resting heart rate threshold, and/or determining the current level of exertion falls below the level of exertion threshold.

At step 914, the wearable device may detect one or more motion features included in a motion profile for a stair stepper (e.g., a stepping motion, side stepping, and/or grip changes) in motion data and/or device headings. If the wearable device detects one or more stair stepper motion features, device headings may be further analyzed to detect a secondary indicator confirming the end of a stair stepper activity. If the wearable device does not detect one or more stair stepper motion features, the absence of stair stepper motion features in motion data generated by the user may be a secondary indicator confirming the end of a stair stepper activity, and a wearable device may end the stair stepper activity, at step 910.

At step 916, the wearable device may detect a sustained variable heading by detecting a series of changes in the device headings estimated during a defined period of time (e.g., 1 minute, 5 minutes, etc.) The device headings remain constant during a stair stepper activity because the user remains on the stair stepper machine travels in the same direction during the stair stepper activity. Therefore, a period of sustained variable heading in which the device headings are not constant for a defined period of time may indicate that a user is not performing a stair stepping activity and may be considered a secondary indicator of the end of a stair stepper activity. In response to detecting the sustained variable heading as secondary indicator of the end of an activity, the wearable device may end the stair stepper activity, at step 910. If the device heading changes once but does not continue to change, the user may be stationary after getting off of a stair stepper machine and/or may be stationary while still on the stair stepper machine.

Therefore, no sustained variable heading is detected, and the wearable device may detect a device timeout, at step 918. If a device timeout is detected, the wearable device waits for the user to resume the stair stepper activity and may calculate an estimate for device heading, at step 906 when activity is resumed. If a device timeout is not detected, the wearable device may repeat steps 912-916 to detect a secondary indicator and confirm the end of the stair stepper activity.

FIGS. 10-12 illustrate exemplary device heading, heart rate, and step cadence data collected by the wearable device during a stair stepper activity. The heading line 1004 in FIG. 10 is analogous to the path a user would take through a room with straight lines having a consistent slope indicating very little heading change and zig zagging lines or abrupt changes in the slope or direction of the heading line 1004 indicating a variable heading. As shown in FIG. 10 the direction of the device heading shown by the heading line 1004 remains constant during the stair stepper activity. As shown in FIG. 10, the end of the stair stepper activity is indicated by an abrupt change in the direction and slope of the heading line 1004 at the variable heading point 1006. The heading line 1004 had a direction that was down and to the right and a negative slope until the variable heading point 1006. At the variable heading point 1006, the direction of the heading line changed to up and to the right and the slope became positive. The relative heading observed between points on the heading line 1004 before and after the variable heading point 1006 exceed the heading threshold (e.g., 140 degrees) for the stair stepper activity. Therefore, the wearable device may detect a primary indicator of the end of the stair stepper activity in device heading data shown in FIG. 10.

As shown in FIG. 11, heart rate of the user remained elevated well above resting (e.g., 120-170 beats per minute (bpm)) during the stair stepper activity. The low point 1102 for heart rate came just after a very intense period of exercise and remained well above resting (e.g., 70 bpm). Heart rate data shown in FIG. 11 may be incorporated into the device headings shown in FIG. 10 with the shade of the heading line 1004 indicating the user's heart rate at that point during the stair stepper activity. For example, the yellow and red shades may indicate the user's heart rate is elevated (i.e., above 120 bpm) at that time during the stair stepper activity and the green and yellow shades may indicate the users heart rate is reduced (below 120 bpm) at that time during the stair stepper activity. As shown in FIG. 10, the green region 1002 of the heading line 1004 corresponds with the low point 1102 for heart rate shown in FIG. 11. After the variable heading point 1006, the heart rate decreases as shown by the green shading and the post activity area 1104 of the heart rate data in FIG. 11. The heart rate in the post activity area 1104, however, is still above a resting heart rate. Therefore, the step cadence data shown in FIG. 12 may be used detect a secondary indicator of the end of a stair stepper activity.

As shown in FIG. 12, step cadence data illustrates a step cadence above 100 steps per minute during the majority of the stair stepper activity aside from a five minute period of 0 steps per minute that corresponds with the low point 1102 of the heart rate data shown in in FIG. 11. The device heading did not change during this period. Therefore, the wearable device detected the user was still on the stair stepper device and maintained the stair stepper activity. The user may have been holding the handrails thereby keeping her arm/wrist position and/or the wearable device steady during this period. The user may have been holding the handrails during the other short periods of 0 steps per minute during the stair stepper activity, therefore no variable heading was detected at these points during the stair stepper activity. After the variable heading point 1006 was detected, there is a larger region of 0 steps per minute was detected in the step cadence data. This period of in-activity after the heading change shown by the step cadence of 0 steps per minute may be detected a secondary indicator by the wearable device confirming the end of the stair stepper activity.

Figure 13:
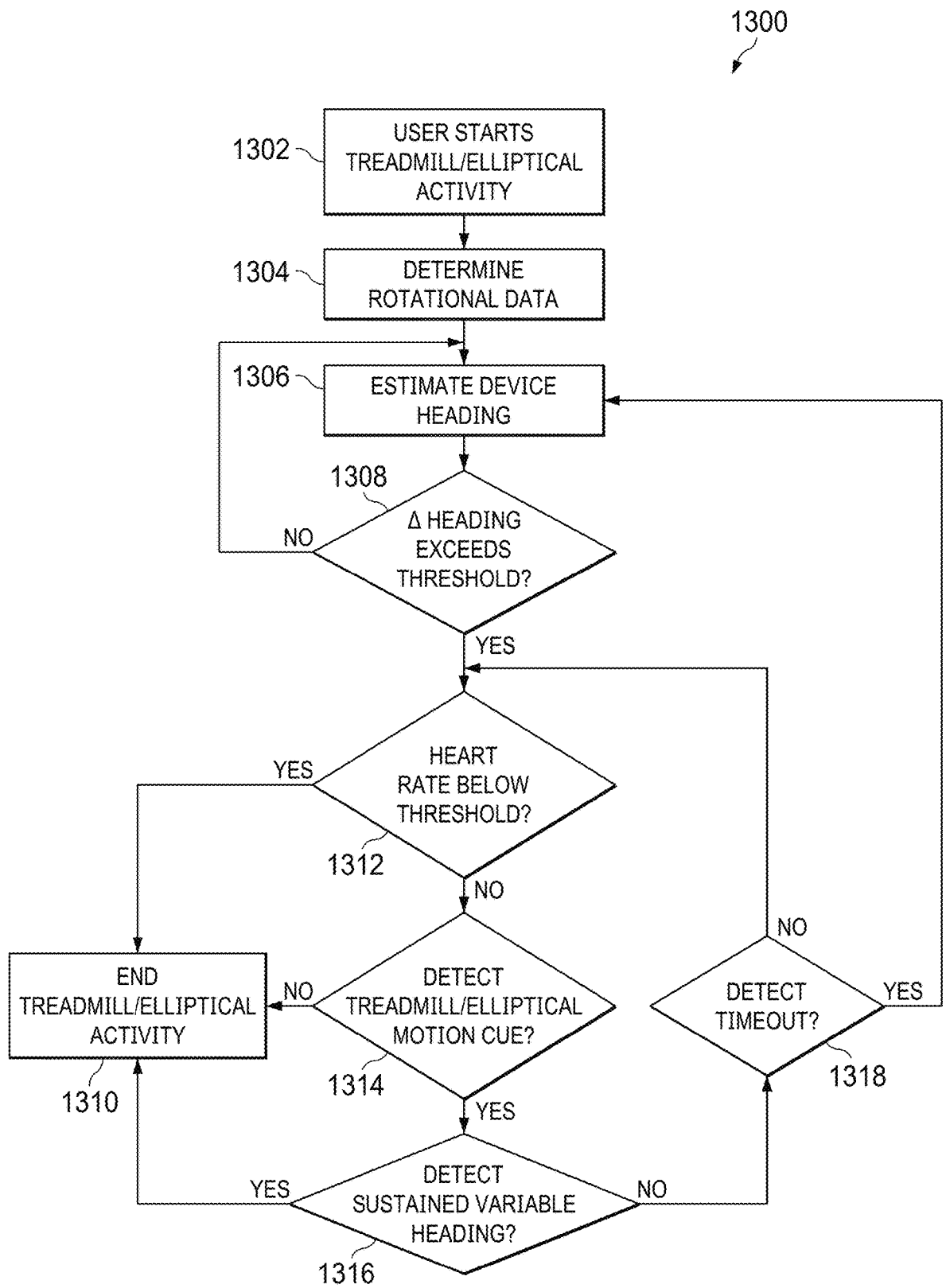
FIG. 13 is a flow chart illustrating a method for detecting an end of a treadmill/elliptical activity, according to embodiments of the disclosure.
Figure 14:
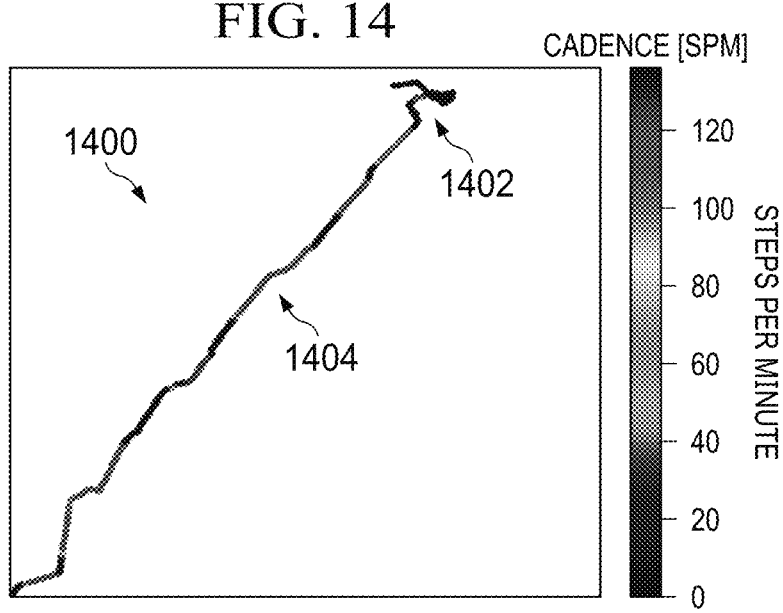
FIGS. 14-16 are graphs showing exemplary heading, heart rate, and step count data used to detect the end of a treadmill/elliptical activity, according to embodiments of the disclosure.
Figure 15:
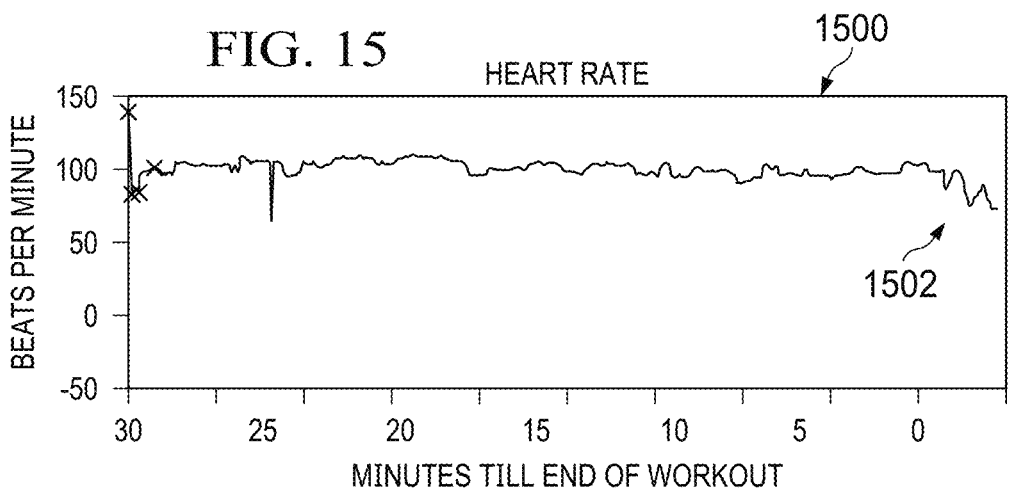
Figure 16:
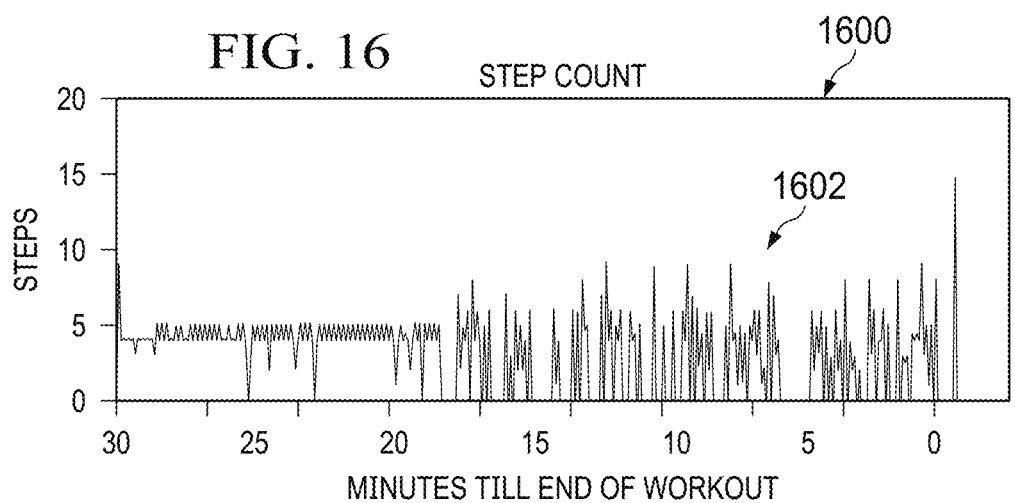

FIGS. 13-16 illustrate an exemplary process and exemplary features that may be used to detect the end of a treadmill/elliptical activity. FIG. 13 illustrates an exemplary process 1300 for detecting the end of a treadmill/elliptical activity and FIGS. 14-16 illustrate three graphs displaying exemplary device heading, heart rate, and step count data collected during a treadmill/elliptical activity. Aspects of the data shown in FIGS. 14-16 are used by the process 1300 illustrated in FIG. 13 to determine the end of a treadmill/elliptical activity. In various embodiments, the device headings and motion data shown in FIGS. 14 and 16 may be analyzed by the wearable device to detect one or more motion features included in a motion model for a treadmill/elliptical machine. For example, motion features included in a motion model for a treadmill/elliptical machine may include a stepping motion and device headings that have subtle differences due to grip changes.

The stepping motion may be unobservable at certain points during the treadmill/elliptical activity. For example, the stepping motion may not be detectable when the user is holding onto the handrails of the machine and thereby keeping the wearable device stationary and the user's arm/wrist pose constant. When the user releases the handrails of the treadmill/elliptical machine, the wearable device may begin detecting the stepping motion by observing changes in the user's arm/wrist pose that are consistent with steps. Therefore, subtle changes in user hand position caused by a user grasping and/or releasing a handrail may correspond with the beginning and/or end of a period having an observable stepping motion. Grip changes while the user is holding the handrails and/or gripping or releasing the handrails may show up in device headings as subtle heading changes that may not exceed a heading threshold for a treadmill/elliptical activity.

In various embodiments, a motion profile for a treadmill/elliptical activity may include a one or more motion features, a heading threshold, and a level of exertion threshold for a treadmill/elliptical activity. The level of exertion threshold for a treadmill/elliptical activity may be high to medium exertion (e.g., between 2.1 metabolic equivalents (METs) and 10.0 METs) due to the variable intensity of treadmill/elliptical activities. By analyzing the heart rate data shown in FIG. 15, the wearable device may detect a secondary indicator of the end of a treadmill/elliptical activity by measuring a heart rate of the user that produces a level of exertion below the level of exertion threshold (e.g., below 2.1 METs) included in the motion profile for the treadmill/elliptical activity. The one or more motion features, the heading threshold, and or the level of exertion threshold for the treadmill/elliptical activity may be determined by surveying a plurality of datasets including motion data, device headings, rotational data, heart rate data, and or exertion levels collected during known treadmill/elliptical activities. The treadmill/elliptical activities may be performed by a particular user and or a group of users having one or more characteristics in common with the particular user.

As shown in FIG. 13, a user starts a treadmill/elliptical activity at step 1302. Heart rate data measured by a heart rate sensor, motion data measured by one or more motion sensors, and magnetic field data measured by a magnetic field sensor may be recorded by the wearable device during the rowing activity. In various embodiments, the heart rate sensor can be a PPG sensor and the wearable device may receive and/or process heart rate data from the PPG sensor according to techniques described in U.S. patent application Ser. No. 15/692,736, filed on Aug. 31, 2017, and entitled "SYSTEMS AND METHODS FOR DETERMINING AN INTENSITY LEVEL OF AN EXERCISE USING PHOTOPLETHYSMOGRAM (PPG)," which patent application is incorporated herein in its entirety. The wearable device may compare the heart rate data received from the heart rate sensor to a resting heart rate threshold (e.g., 30-70 beats per minute (bpm)) to determine that the user is active. The resting heart rate threshold may depend on characteristics of the user including age, fitness level, level of fatigue, and the like.

At step 1304, motion data and/or magnetic field data may be used to calculate rotational data. At step 1306, device heading may be estimated from rotational data describing the angle/position of the wearable device in 3D space relative to a reference frame. To determine changes in user direction, the wearable device may track changes in device heading during the activity session to determine the relative device heading. For example, periodically (i.e., continuously or at other defined time intervals) during the treadmill/elliptical activity, the wearable device may estimate a relative device heading by calculating a heading difference (e.g., the difference between a current device heading and the device heading at a previous time point). If, at step 1308, the heading difference exceeds a heading threshold for the treadmill/elliptical activity, a primary indicator for the end of a treadmill/elliptical activity may be detected. In response to detecting the primary indicator, the wearable device may search for a secondary indicator of the end of the treadmill/elliptical activity to confirm the activity is over. If, at step 1308, the heading difference does not exceed the heading threshold for the treadmill/elliptical activity, the wearable device may maintain the treadmill/elliptical activity and continue to estimate device heading. In various embodiments, the treadmill/elliptical motion model may include one or more motion features that may be detected in device headings. For example, subtle changes in device heading that occur when a user adjusts her grip on the handrails and/or grips or releases a handrail. These grip changes may show up in device headings as small relative heading values (i.e., changes of 20 degrees or less) that do not exceed the heading threshold (e.g., 90 to 140 degrees) for the treadmill/elliptical activity.

At steps 1312-1316, the wearable device may attempt to confirm the end of the treadmill/elliptical activity by searching for a secondary indicator of the end of the activity in heart rate data, motion data, and device headings. At step 1312, the wearable device may determine a user's current heart rate is below one or more heart rate thresholds (e.g., a resting heart rate threshold, an average of heart rate threshold, a relative heart rate threshold, and the like). The wearable device may also use heart rate data to determine a level of exertion for the user and compare a current level of exertion to a level of exertion threshold. If the current heart rate/level of exertion is below a heart rate threshold/level of exertion threshold, the wearable device may end the treadmill/elliptical activity, at step 1310. If the current heart rate/level of exertion is not below a heart rate threshold/level of exertion threshold, the wearable device may search for a secondary indicator to confirm the end of a treadmill/elliptical activity in motion data and/or device headings. The level of exertion threshold for a treadmill/elliptical activity may be a high to medium exertion (e.g., 2.1 METs to 10.0 METs).

In various embodiments, the wearable device may detect the end of the treadmill/elliptical activity using a relative heart rate. Relative heart rate may describe the difference between the current user heart rate and the average user heart rate during the activity session. To determine the user's relative heart rate, the wearable device calculates an average heart rate of the user during the treadmill/elliptical activity. The wearable device then computes the difference between the user's current heart rate and the average user heart rate to determine the relative heart rate. To confirm the end of a treadmill/elliptical activity, the wearable device may compare the relative heart rate to a relative heart rate threshold for the treadmill/elliptical activity. If the current relative heart rate is below the relative heart rate threshold, the wearable device may end the treadmill/elliptical activity at step 1310. In various embodiments, the wearable device may end the cardio machine activity upon determining the relative heart rate is below the relative heart rate threshold for the treadmill/elliptical activity, determining the current heart rate is below the resting heart rate threshold, and/or determining the level of exertion is below the level of exertion threshold for the treadmill/elliptical activity. The relative heart rate threshold for a treadmill/elliptical activity may be determined by surveying a plurality of datasets including heart rate data and or relative heart rates collected during known treadmill/elliptical activities. The treadmill/elliptical activities included in the plurality of datasets may be performed by a particular user and or a group of users having one or more characteristics in common with the particular user.

At step 1314, the wearable device may detect one or more motion features (e.g., a stepping motion, grip changes, and the like) included in the motion model for a treadmill/elliptical activity in motion data and/or device headings. If the wearable device detects one or more treadmill/elliptical motion features, device headings may be further analyzed to detect a secondary indicator confirming the end of a treadmill/elliptical activity. If the wearable device does not detect one or more treadmill/elliptical motion features, the absence of treadmill/elliptical motion features in motion data may be a secondary indicator confirming the end of a treadmill/elliptical activity, and a wearable device may end the treadmill/elliptical activity, at step 1310.

At step 1316, the wearable device may detect a sustained variable heading by detecting a series of changes in the device headings estimated during a defined period of time (e.g., 1 minute, 5 minutes, etc.). The device heading remains constant during a treadmill/elliptical activity because the user performs the treadmill/elliptical activity while on the treadmill/elliptical machine and faces the same direction during the activity. Therefore, a period of sustained variable heading in which the device headings are not constant for a defined period of time indicates a user is not performing a treadmill/elliptical activity and may be considered a secondary indicator that the user has ended the treadmill/elliptical activity that causes the wearable device to end the treadmill/elliptical activity at step 1310. If the device heading changes significantly enough for the relative heading to exceed the heading threshold for the treadmill/elliptical activity (e.g., a relative heading above 90 degrees) but does not continue to change during a defined period of time, the user may be stationary after getting off of a treadmill/elliptical machine and/or may be stationary while still on the cardio machine. Therefore, no sustained variable heading is detected and the wearable device may detect a device timeout, at step 1318. If a device timeout is detected, the wearable device may wait for the user to resume the treadmill/elliptical activity and may continue to estimate device headings, at step 1306 when activity is resumed. If a device timeout is not detected, the wearable device may repeat steps 1312-1316 to detect a secondary indicator that confirms the end of the treadmill/elliptical activity.

FIGS. 14-16 illustrate exemplary device heading, heart rate, and step count data collected by the wearable device during a treadmill/elliptical activity. The heading line 1404 in FIG. 14 is analogous to the path a user would take through a room. Straight segments of the heading line 1404 having a consistent slope and direction indicate very little heading change (i.e., relative headings that are below the heading threshold for the treadmill/elliptical activity) and zig zagging lines or abrupt changes in the slope or direction of the heading line 1404 indicate a variable heading. As shown in FIG. 14, the device heading remained mostly constant during the treadmill/elliptical activity as shown by the constant positive slope and constant up and to the right direction of the heading line 1404. As shown in FIG. 14, the end of the treadmill/elliptical activity was indicated by an abrupt change in slope of the heading line 1404 at the variable heading point 1402 from positive to near zero. The direction of the heading line 1404 also changed at the variable heading point 1402 from up and to the right to flat and to the left. Therefore, the relative heading between a point before the variable heading point 1402 and a point after the variable heading point 1402 exceeds the heading threshold for the treadmill/elliptical activity. The wearable device may detect the change in device heading shown at the variable heading point 1402 as a primary indicator of the end of the treadmill/elliptical activity.

As shown in FIG. 15, heart rate of the user remained elevated well above resting (e.g., 100-110 bpm) during the treadmill/elliptical activity. After the variable point, the heart rate decreases as shown by the heart rate below 100 bpm in the post activity area 1502 at 0 minutes to the end of the treadmill/elliptical activity. However, the heart rate at 0 minutes is still above a resting heart rate (e.g., 30 to 70 bpm). Therefore, the end of the treadmill/elliptical activity may not be confirmed using the heart rate data shown in FIG. 15. To confirm the end of the treadmill/elliptical activity, the wearable device may analyze the step count data shown in FIG. 16. As shown in FIG. 16, the step count data includes intervals of elevated step count 1602 (e.g., above 10 steps) during the majority of the treadmill/elliptical activity. The step count consistently fluctuates between 0 and 10 during the treadmill/elliptical activity. The device heading did not change during this period therefore, the wearable device detected the user was still on the treadmill/elliptical device and maintained the treadmill/elliptical activity. The 0 step counts during the treadmill/elliptical activity may have be detected when the user was holding the handrails thereby keeping her wrist position and the device steady during this time during the treadmill/elliptical activity.

After the variable heading point 1402 was detected, there is a larger region of zero step count beginning at 0 minutes to the end of workout. However, some steps were detected even after the variable heading point. Therefore, additional analysis of the device heading may be needed to confirm the end of the treadmill/elliptical activity. As shown in FIG. 14, the variable heading is sustained. First, at the variable heading point 1402, the slope of the heading line 1404 changes from positive to near zero and the direction of the heading line sifts from up and to the right to flat and to the right. A short time after the variable heading point 1402, the slope of the heading line 1404 remains near zero but the direction of the heading line 1404 changes from flat and to the right to flat and to the left. This 180 degree change in heading immediately after a large (i.e., greater than 90 degree) change in heading at the variable heading point is detected by the wearable device as a sustained variable heading. The wearable device may determine the sustained variable heading is a secondary indicator confirming the end of the treadmill/elliptical activity.

Figure 17:
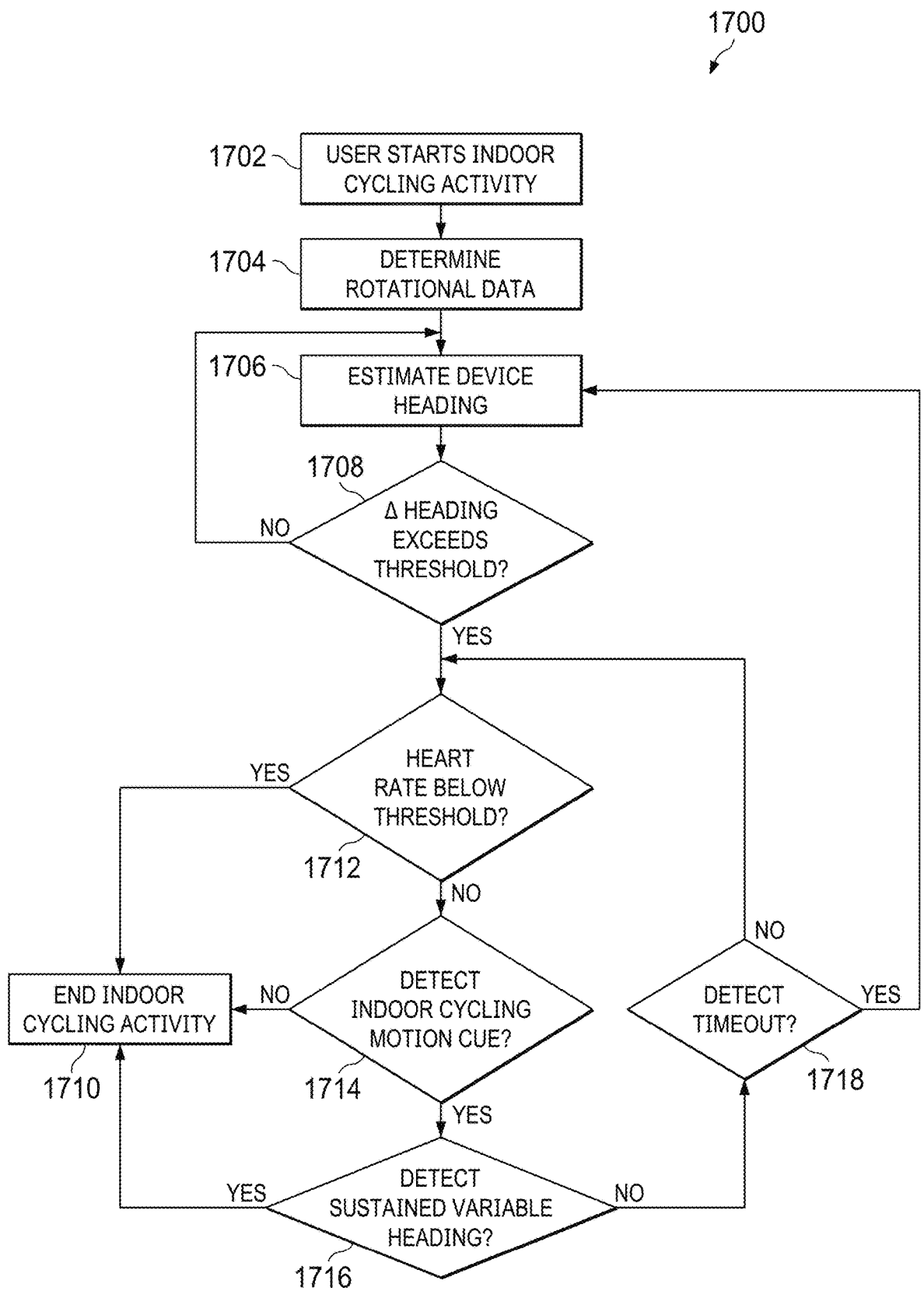
FIG. 17 is a flow chart illustrating a method for detecting an end of an indoor cycling activity, according to embodiments of the disclosure.
Figure 19:
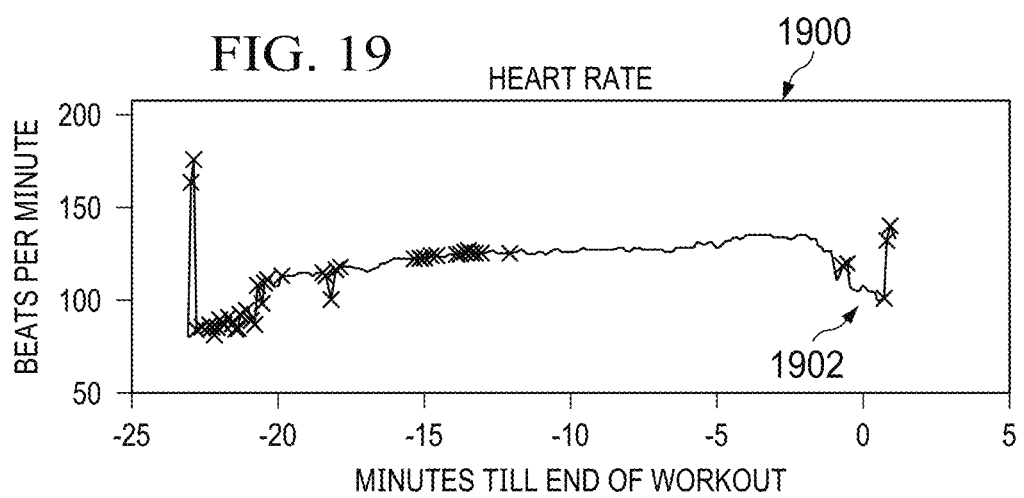
Figure 20:
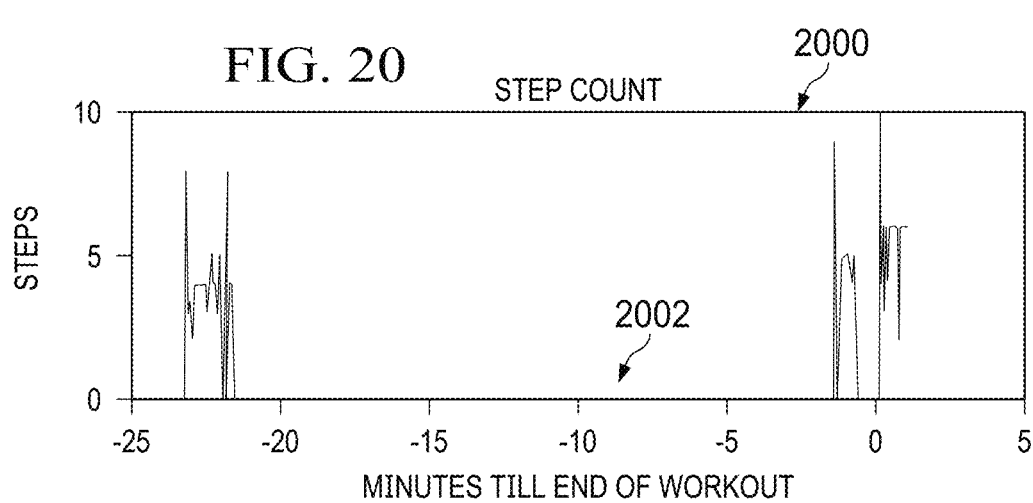

FIGS. 17-20 illustrate an exemplary process and motion features used to detect the end of an indoor cycling activity. FIG. 17 illustrates an exemplary process 1700 for detecting the end of an indoor cycling activity and FIGS. 18-20 illustrate three graphs displaying exemplary device heading, heart rate, and step count data collected during an indoor cycling activity. Aspects of the data shown in FIGS. 18-20 are used by the process 1700 shown in FIG. 17 to determine the end of an indoor cycling activity. In various embodiments, the device headings and motion data shown in FIGS. 18 and 20 may be analyzed by the wearable device to detect one or more motion features included in a motion model for an indoor cycling machine. Motion features included in a motion model for an indoor cycling machine may include pedal strokes, no steps, a low, alternating arm swing, and device headings that have subtle differences due to grip changes.

The low alternating arm swing may be a swinging motion observable in the arm/wrist of the user as the user's body rocks back and forth while pedaling. The low alternating arm swing may be very subtle when the user is pedaling in a seated position. The amount of arm swing observable in the low alternating arm swing motion may increase when the user begins pedaling in a standing position and/or increases pedaling cadence or becomes more tired. Grip changes while the user is holding the handlebars and/or gripping or releasing the handlebars may show up in device headings as small relative heading values (e.g., less than 20 degrees) that may not exceed a heading threshold (e.g., greater than 90 degrees).

In various embodiments, the motion profile for the indoor cycling machine may include one or more motion features, the heading threshold, and or a level of exertion threshold for an indoor cycling activity. The motion features, heading threshold, and or level of exertion threshold may be determined by surveying a plurality of datasets including motion data, rotational data, heart rate data, device headings, and or level of exertion estimates collected during known indoor cycling activities. The indoor cycling activities included in the plurality of datasets may be performed by a particular user and or a group of users having one or more characteristics in common with the particular user. The expected level of exertion for an indoor cycling activity may be high to very low exertion (e.g., 1.1 to 10.0 METs) due to the highly variable intensity of indoor cycling activities. By analyzing the heart rate data shown in FIG. 19, the wearable device may detect a secondary indicator of the end of an indoor cycling activity by measuring a heart rate of the user that produces a level of exertion below the level of exertion threshold (e.g., below 1.1 METs) for the indoor cycling activity.

As shown in FIG. 17, a user starts an indoor cycling activity at step 1702. During the cycling activity, the wearable device may record heart rate data from a heart rate sensor, motion data from one or more motion sensors, and magnetic field data from one or more magnetic field sensors. In various embodiments, the heart rate sensor can be a PPG sensor and the wearable device may receive and/or process heart rate data from the PPG sensor according to techniques described in U.S. patent application Ser. No. 15/692,736, filed on Aug. 31, 2017, and entitled "SYSTEMS AND METHODS FOR DETERMINING AN INTENSITY LEVEL OF AN EXERCISE USING PHOTOPLETHYSMOGRAM (PPG)," which patent application is incorporated herein in its entirety. The wearable device may compare the heart rate data received from the heart rate sensor to a resting heart rate threshold (e.g., 30-70 beats per minute (bpm)) to determine the user is active. The resting heart rate threshold may depend on characteristics of the user including age, fitness level, level of fatigue, and the like.

At step 1704, motion data and/or magnetic field data may be used to determine rotational data. The rotational data may then be used to calculate a device orientation describing the position of the wearable device with a reference frame. At step 1706, device heading may be estimated from the rotational data to determine the direction of travel of a user. The wearable device may estimate a device heading continuously during the indoor cycling activity to track the device heading throughout the indoor cycling activity. Periodically (e.g., continuously or at any other regular time interval) during the indoor cycling machine activity, the wearable device may estimate a change in device heading (i.e., a relative device heading) by calculating a heading difference (e.g., the difference between an current device heading and a device heading measured at a previous time point). If, at step 1708, the heading difference exceeds the heading threshold for the indoor cycling activity, a primary indicator of the end of an indoor cycling activity may be detected and the wearable device may search for a secondary indicator to confirm the end of the indoor cycling activity. If, at step 1708, the heading difference does not exceed the heading threshold for the indoor cycling activity, the wearable device may maintain the indoor cycling activity and continue to estimate device heading.

In various embodiments, one or more motion features included in the indoor cycling motion model may be detected in device headings recorded during an indoor cycling activity. The one or more motion features detectable from device headings for an indoor cycling activity may be, for example, grip changes during an indoor cycling activity. The grip changes may include a user adjusting the position of one or more hands on the handlebars and/or gripping or releasing the handlebars. These grip changes may show up in the heading data as small relative heading values (e.g., less than 20 degrees) that do not exceed the heading threshold (e.g., more than 90 degrees).

At steps 1712-1716, the wearable device may attempt to confirm the end of the indoor cycling activity by searching for a secondary indicator of the end of the indoor cycling activity end in heart rate data, motion data, and/or device headings. At step 1712, the wearable device may determine a user's current heart rate is below one or more heart rate thresholds (e.g., a resting heart rate threshold, average heart rate threshold, relative heart rate threshold, and the like). The wearable device may also use heart rate data to determine a level of exertion for the user and compare a current level of exertion to a level of exertion threshold. If the current heart rate/level of exertion is below a heart rate threshold/level of exertion threshold, the wearable device may end the indoor cycling activity at step 1710. If the current heart rate/level of exertion is not below a heart rate threshold/level of exertion threshold, the wearable device may search for a secondary indicator to confirm the end of an indoor cycling activity in motion data and/or device headings.

In various embodiments, the wearable device may detect the end of a cardio machine activity using a relative heart rate. Relative heart rate may describe the difference between the current user heart rate and the average user heart rate during the activity session. To determine the user's relative heart rate, the wearable device calculates an average heart rate of the user during an indoor cycling activity. The user device then computes the difference between the user's current heart rate and the average user heart rate to determine the relative heart rate. To confirm the end of the indoor cycling activity, the wearable device may compare a relative heart rate to a relative heart rate threshold. If the relative heart rate threshold fails the relative heart rate threshold, the wearable device may end the indoor cycling activity at step 1710. In various embodiments, the wearable device may end the cardio machine activity upon determining the relative heart rate is below the relative heart rate threshold, determining the current heart rate is below the resting heart rate threshold, and/or determining the current level of exertion is below the level of exertion threshold. The one or more heart rate thresholds, the relative heart rate threshold, and or the level of exertion threshold for the indoor cycling activity may be determined by surveying a plurality of datasets including heart rate data, relative heart rates, and or level of exertion calculations collected during known indoor cycling activities. The indoor cycling activities included in the plurality of datasets may be performed by a particular user and or a group of users having one or more characteristics in common with the particular user.

At step 1714, the wearable device may detect one or more motion features included in an indoor cycling motion model (e.g., pedaling motion, no steps, arm swing, and grip changes), in motion data and/or device headings. If the wearable device detects one or more indoor cycling motion features, device headings may be further analyzed to detect a secondary indicator confirming the end of an indoor cycling activity. If the wearable device does not detect one or more indoor cycling features, the absence of motion features in motion data generated by the user may be a secondary indicator confirming the end of an indoor cycling activity, and a wearable device may end the indoor cycling activity, at step 1710.

At step 1716, the wearable device may detect a sustained variable heading by detecting a series of changes device headings estimated during a defined period of time (e.g., 1 minute, 5 minutes, etc.) that exceed the heading threshold for the indoor cycling activity. The device headings remain constant during an indoor cycling activity because indoor cycling activities are performed on a stationary indoor cycling machine while facing a forward direction. Therefore, a period of sustained variable heading in which the device headings are not constant for a defined period of time indicates a user is not performing an indoor cycling activity and may be considered a secondary indicator of an activity end that causes the wearable device to end the indoor cycling activity, at step 1710. If the wearable device detects one change in device heading that exceeds the heading threshold but the relative heading does not continue to exceed the heading threshold, the user may be stationary after getting off an indoor cycling machine and/or may be stationary while still on the cardio machine. Therefore, if no sustained variable heading is detected after a first variable heading, the wearable device may detect a device timeout, at step 1718. If a device timeout is detected, the wearable device may wait for the user to resume cardio machine activity and may continue to calculate device headings at step 1706, when activity is resumed. If a device timeout is not detected, the wearable device may repeat steps 1712-1716 to detect a secondary indicator that confirms the end of the indoor cycling activity.

FIGS. 18-20 illustrate exemplary device heading, heart rate, and step count data collected by the wearable device during an indoor cycling activity. The heading line 1804 in FIG. 18 is analogous to the path a user would take through a room. Straight segments of the heading line 1804 having a consistent slope and direction indicate very little heading change (i.e., relative headings that are below the heading threshold for the treadmill/elliptical activity) and zig zagging lines or abrupt changes in the slope or direction of the heading line 1804 indicate a variable heading. As shown in FIG. 18, the direction of the device heading shown by the heading line 1804 remained constant at an up and to the right direction throughout the indoor cycling activity. As shown in FIG. 18, an abrupt change in slope of the heading line 1804 occurred at the variable heading point 1802 when the slope of the heading line 1804 changed from a positive slope to a negative slope. The direction of the heading line 1804 also changed at the variable heading point 1802 from an up and to the right direction to a down and to the left direction. The variable heading shown by the changes in slope and direction of the heading line 1804 may be detected by the wearable device as a primary indicator of the end of a cardio machine activity.

As shown in FIG. 19, the heart rate of the user remained elevated above resting (e.g., 80-120 bpm) during the indoor cycling activity. After the variable heading point, the heart rate decreases in the post activity area 1902 beginning at 0 minutes to the end of the workout before increasing to about the average heart rate during the indoor cycling activity. Because the heart rate remains above the resting threshold after the variable heading, the wearable device may not confirm the end of the indoor cycling activity from the heart rate data. To confirm the end of the activity, the wearable device may analyze the step count data shown in FIG. 20. As shown in FIG. 20, a prolonged period 2002 of zero steps was detected during the indoor cycling activity. The step count fluctuates between zero and 10 steps during the indoor cycling activity. At the end of the indoor cycling activity, more consistent step count is observed along with no prolonged periods having zero steps. Zero steps may be an indoor cycling motion feature included in an indoor cycling motion model, therefore, detecting steps after the variable heading may be used as a secondary indicator by the wearable device to confirm the end of the indoor cycling activity.

Figure 21:
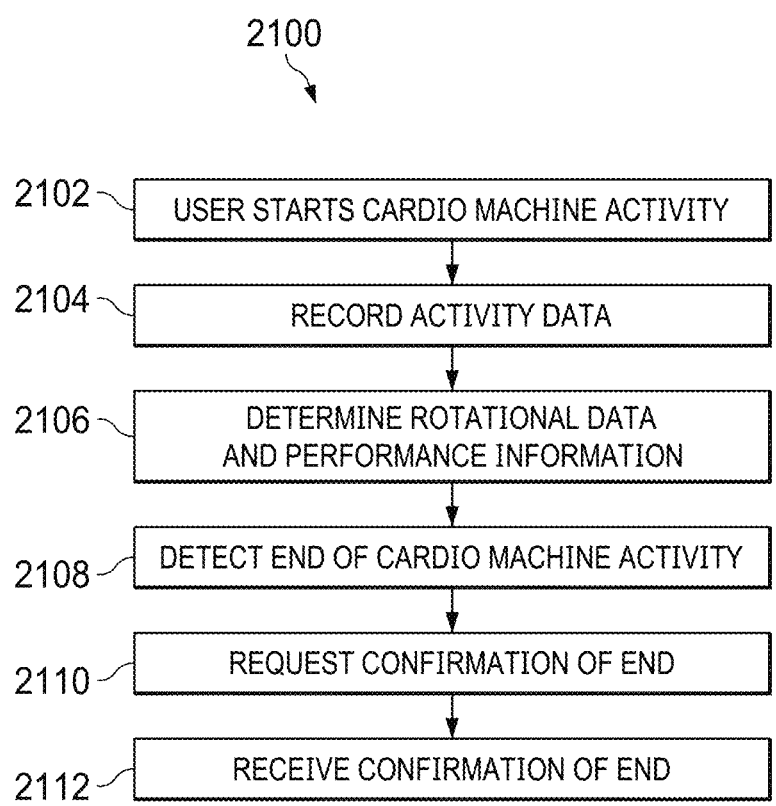
FIG. 21 is a flow chart illustrating a method of requesting confirmation of an end of a cardio machine activity from a user, according to embodiments of the disclosure.

FIG. 21 illustrates an exemplary process 2100 for notifying and confirming the end of a cardio machine activity. At step 2102, a user begins a cardio machine activity. In response to the start of a cardio machine activity, the wearable device may record activity data including heart rate data, motion data, and or magnetic field data during the activity session. Activity data may be used to determine rotational data and performance information (e.g., exertion level, mechanical work done, calories burned, workout time, and the like) at step 2106. Rotational data may be used to estimate device orientations and or device headings.

At step 2108, the wearable device may detect the end of a cardio machine activity based on device heading, heart rate data, and or motion data as described above. Once the wearable device determines a cardio machine activity has ended, it may send a notification to a user requesting confirmation of the end of the cardio machine activity, at step 2110. For example, the wearable device may generate a confirmation request that is rendered on the display of the wearable device. The confirmation request may be in the form of a graphical user interface (GUI) that includes an input (e.g., button, selection, slider, free form text box, and the like) that allows the user to submit a response to the confirmation request (e.g., "Have you completed your cardio machine workout?"). In various embodiments, the confirmation request may include the type of cardio machine activity (e.g., stair stepper activity, treadmill/elliptical activity, indoor cycling activity, rowing machine activity, and the like) identified by the wearable device. At step 2112, the wearable device may receive a confirmation from a user of the end of a cardio machine activity. For example, an input into the GUI in response to the confirmation request that indicates the cardio machine activity has ended. The confirmation received from a user may be used to label the determination that the cardio machine activity has ended made by the wearable device is accurate. In response to receiving the confirmation for the user, the activity data, performance information and rotational data determined from the activity data, the device headings and device orientations estimated from the rotational data, the exertion levels calculated from the heart rate data, and motion features detected in the motion data and device headings recorded during the cardio machine activity may be labeled as generated during a known cardio machine activity. The type of cardio machine activity indicated in the confirmation received from the user may also be associated with the activity data, performance information, rotational data, device headings, device orientations, exertion levels, and motion features recorded during the activity. These labeled datasets may be included in the plurality of datasets used to determine one or more features included in motion models for each activity type and improve the accuracy and efficiency of determinations of the end of activities made by the motion models as described above.

Figure 22:
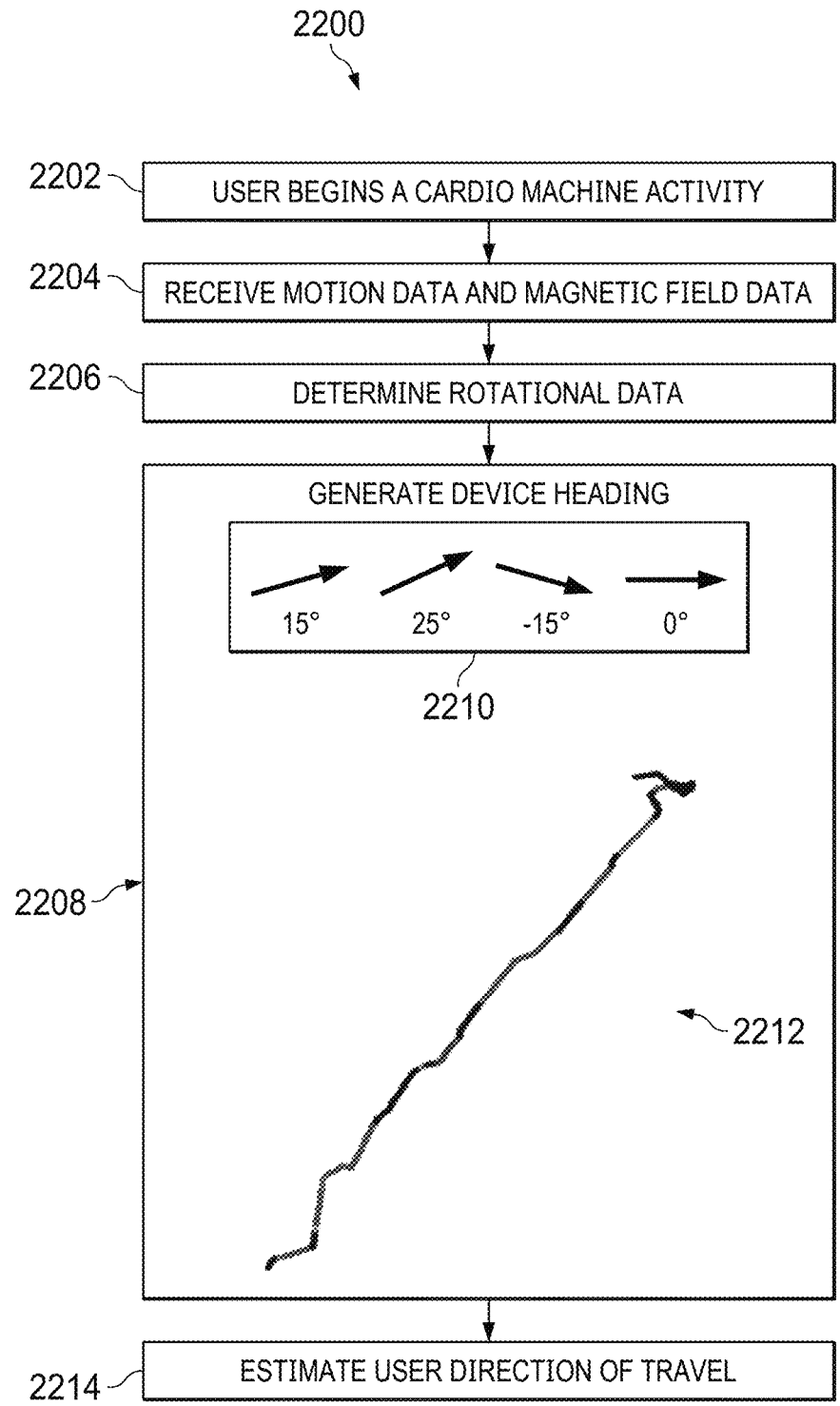
FIG. 22 is a block diagram illustrating how user direction of travel is estimated from device heading and orientation, according to embodiments of the disclosure.

FIG. 22 shows an exemplary process 2200 for estimating a user direction of travel using device heading. At step 2202, a user begins a cardio machine activity. At step 2204, motion data and magnetic field data are received from the one or more motion sensors and the magnetic field sensor of the wearable device. At step 2206, the wearable device determines rotational data from the motion data using 6 axis sensor fusion. The wearable device may also determine rotational data from motion data and magnetic field data using 9 axis sensor fusion at step 2206. At step 2208, device headings 2210 are estimated based on the rotational data. Relative headings describing the change in device headings over time during the activity session may also be calculated based on the device headings.

The wearable device may estimate device headings by averaging or otherwise combining the 6 axes or 9 axes of rotational data to generate the 3D rotational data discussed below in connection with FIGS. 23A-25. For example, the 2 rotational angles (e.g., one angle determined from angular acceleration and one angle determined from angular velocity) for each rotational axis (e.g., roll, pitch, and yaw) in the 6 axis sensor fusion approach may be combined to generate 3 rotational angles (e.g., one angle for each rotational axis) that describe the position of the wearable relative to an axis of rotation (e.g., yaw, pitch, and roll) within a frame of reference. For example, the frame of reference may be a fixed body frame of reference relative to a fixed portion of the wearable device or an inertial frame of reference relative to gravity. This 3D rotational data may be projected into a 2D vector. The 2D vector may then be filtered to reduce noise. For example, the three dimensional rotational data collected using the 6 axis and or 9 axis approach is a 3D vector that moves in time and can be represented as $i(t)=(x(t), y(t), z(t))$. Then, in some embodiments, $i(t)$ can be projected onto the x-y plane using the gravity vector, and the resulting 2D vector can be represented as $j(t)=(x(t), y(t))$. The x-component and y-component of $j(t)$ may each individually filtered by a low-pass filter. The heading calculated for the device (i.e., device heading) corresponds to the angle between $j(t)$ (i.e., the 2D rotational motion vector). To detect changes in the user's direction, the relative heading may be plotted to show the user's heading at multiple time points during the activity session. The change in the user's heading may then be calculated at adjacent times to show how $j(t)$ is progressing in time. For example, suppose at $t=0$, $(x=1, y=0)$, and then at $t=1$, $(x=0, y=1)$, then the angle change (i.e., the change in heading) would be 90 degrees.

Device headings may also be determined using the device heading model as described above. For example, device headings may be determined based on device orientations generated from rotational data. The device orientations may describe the angle/position of the wearable device at a particular point in time during the cardio machine activity. Device orientations may be generated by applying one or more trigonometric functions (e.g., sine (sin), cosine (cos), tangent (tan), cosecant (csc), secant (sec), and cotangent (cot)) to one or more rotational angles describing the position of the wearable relative to an axis of rotation (e.g., yaw, pitch, and roll) within a frame of reference. For example, the frame of reference may be a fixed body frame of reference relative to a fixed portion of the wearable device or an inertial frame of reference relative to gravity.

In various embodiments, device headings 2210 may also be calculated by algorithmically combining the yaw component (e.g., rotational angle relative to the x axis or horizontal plane of the fixed body and or inertial frame of reference) of the rotational data generated from gyroscope motion data, accelerometer motion data, and magnetic field data. By combining two rotational data values generated from motion data with a third rotational data value of generated from magnetic field data for each rotational axis, the accuracy of device headings may be improved. Relative device headings describing changes in device headings overtime may be computed by taking the difference between two or more device headings measured at different periods of time during the cardio machine activity.

In various embodiments, rotational data for each activity may be plotted in a 3D dimensional space bounded by three axes having a range of values between −1 and 1 to generate device orientations. By analyzing plots including a repeating sequence of motion performed during a particular type of cardio machine activity, one or more motion features may be extracted from the rotational data. In various embodiments, motion features based on device headings and/or relative device headings (e.g., relative heading values above the heading threshold that indicates the end of a particular type of cardio machine activity) may be observed in the rotational data by detecting one or more clusters, groups, sequences, patterns, and/or heuristics in the horizontal plane of the device orientation plots projecting the rotational data. For example, the number of clusters of device orientations included in the rotational data separated some lateral distance in the horizontal plane may correspond to the number of distinct device headings within the cardio machine activity. Therefore, rotational data that generates a device orientation plot having one cluster of device orientations may correspond to cardio machine activities having zero heading changes. In response to receiving a device orientation outside of the cluster, the wearable device may detect a heading change (e.g., a variable heading) as a primary indicator of the end of a cardio machine activity.

In various embodiments, the rotational data and device orientations may be generated according to techniques described in U.S. patent application Ser. No. 15/691,245, filed on Aug. 30, 2018, and entitled "SYSTEMS AND METHODS FOR DETERMINING SWIMMING METRICS," which patent application is incorporated herein in its entirety. FIGS. 23-23E below describe how the rotational data may be generated in more detail.

Device headings measured during an activity session may be sequenced and assembled into a directional diagram 2212 corresponding to how a device would move through a room if it was moving at a constant speed at each point in time. Heading line segments having the same slope and/or direction indicate consistent direction of travel at each point in time and a constant device heading. Segments of heading lines having different slopes and/or directions indicate a variable direction of travel and a variable heading. Device headings included in the directional diagram 2212 may be used to estimate a user's direction of travel during the cardio machine activity, at step 2214. Using the device headings, the wearable device may predict the user's intent to remain on a cardio machine and or the user's behavior (i.e., when the user gets off the cardio machine, when the user transitions from one cardio machine to a second cardio machine, and or when the user ends a cardio machine activity) based on the user's estimated direction of travel.

Orientation data may describe the position of a wearable device relative to a frame of reference. FIGS. 23A-D describe embodiments of orientation data generated relative to a body fixed frame of reference and FIGS. 22-23E describe embodiments of orientation data generated relative to a inertial frame of references.

Figure 23A:
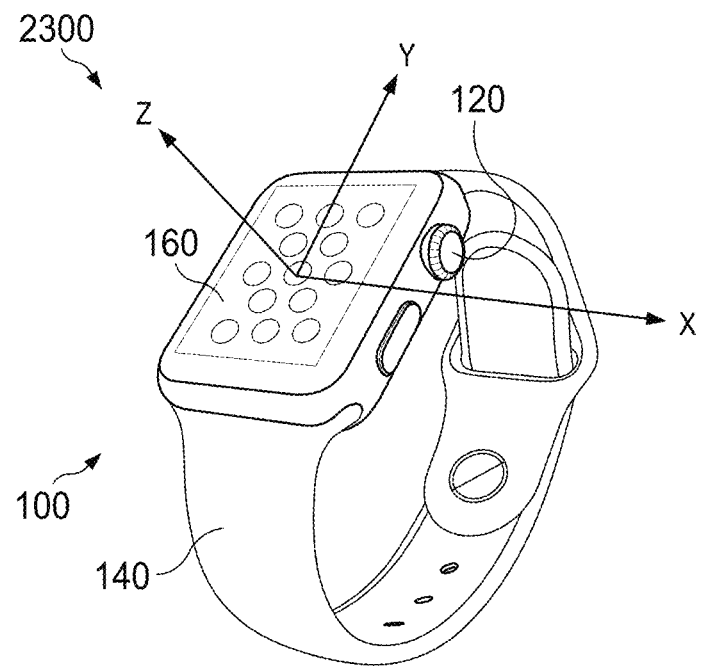
FIGS. 23 A-D illustrate methods for measuring the orientation of wearable devices relative to a fixed body frame of reference, according to embodiments of the disclosure.

FIG. 23A illustrates an example of a body-fixed frame of reference 2300 according to various embodiments of the present disclosure. In FIG. 23A, the rotational axes of body-fixed frame of reference 2300 are with respect to wearable device 100. For example, the z-axis is perpendicular to the display surface 160 of wearable device 100. The x-axis and the y-axis can be chosen relatively arbitrarily as long as the three axes are perpendicular to each other. In FIG. 23A, the x-axis is parallel with the direction pointed by a crown 120 of wearable device 100, and the y-axis is parallel with the direction of the band 140 of wearable device 100 (assuming the direction pointed by the crown 120 of wearable device 100 is perpendicular to the direction of the band 140 of wearable device 100).

Figure 23B:
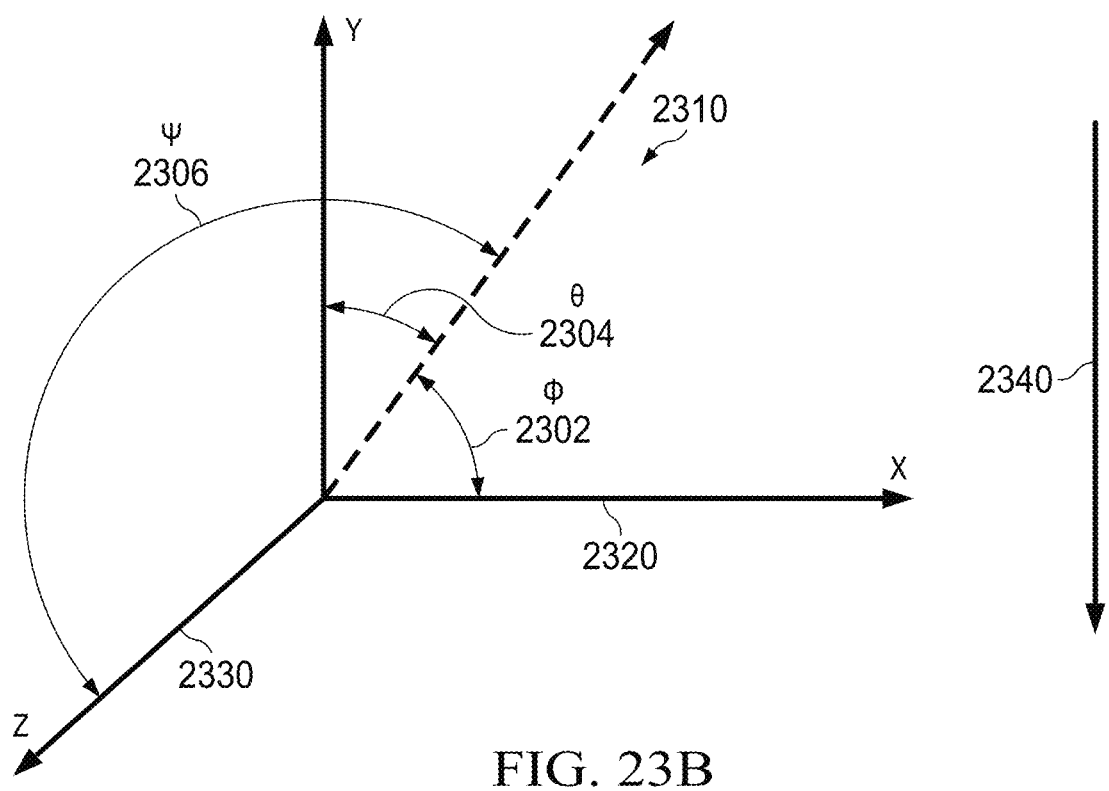
Figure 23C:
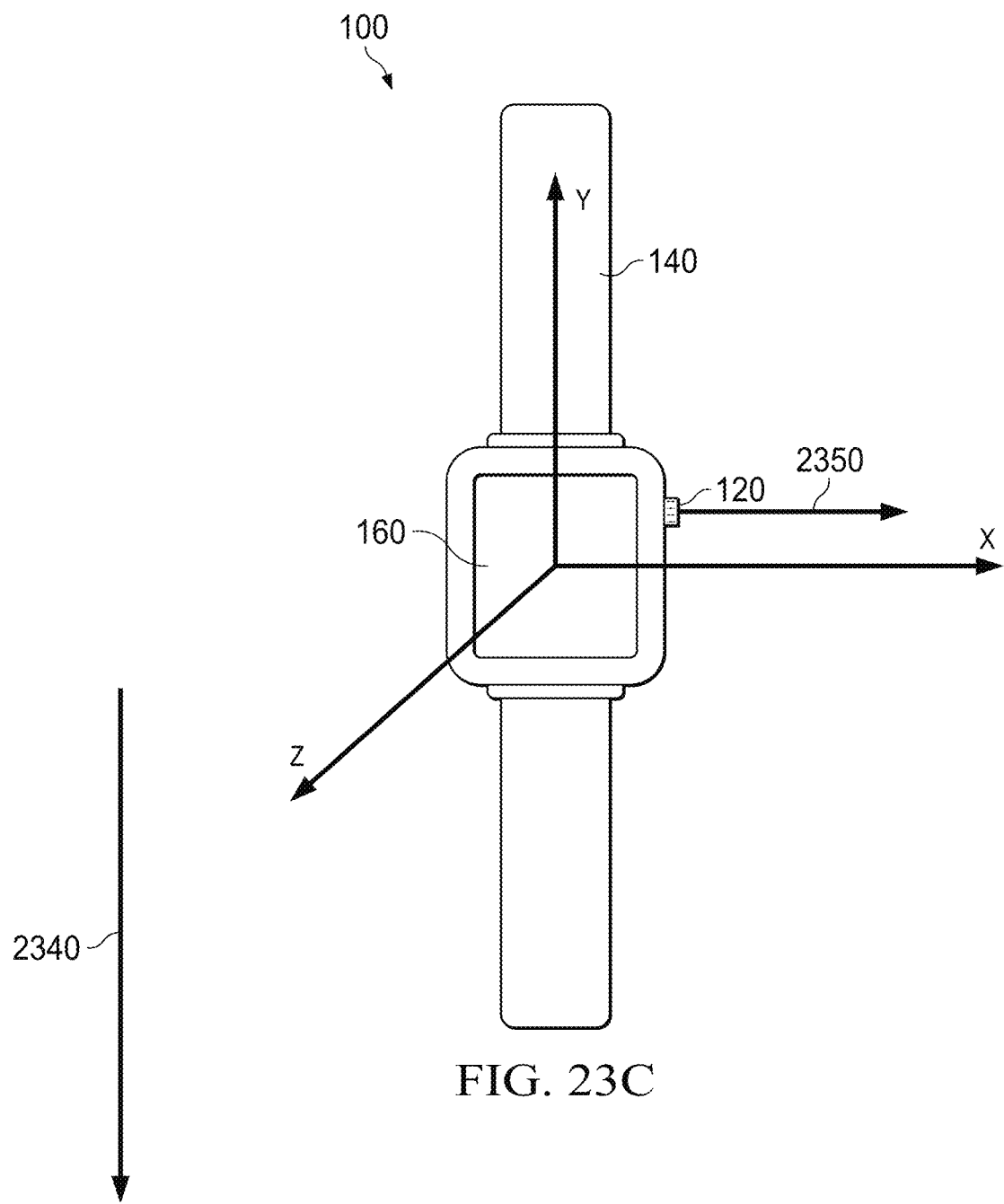
Figure 23D:
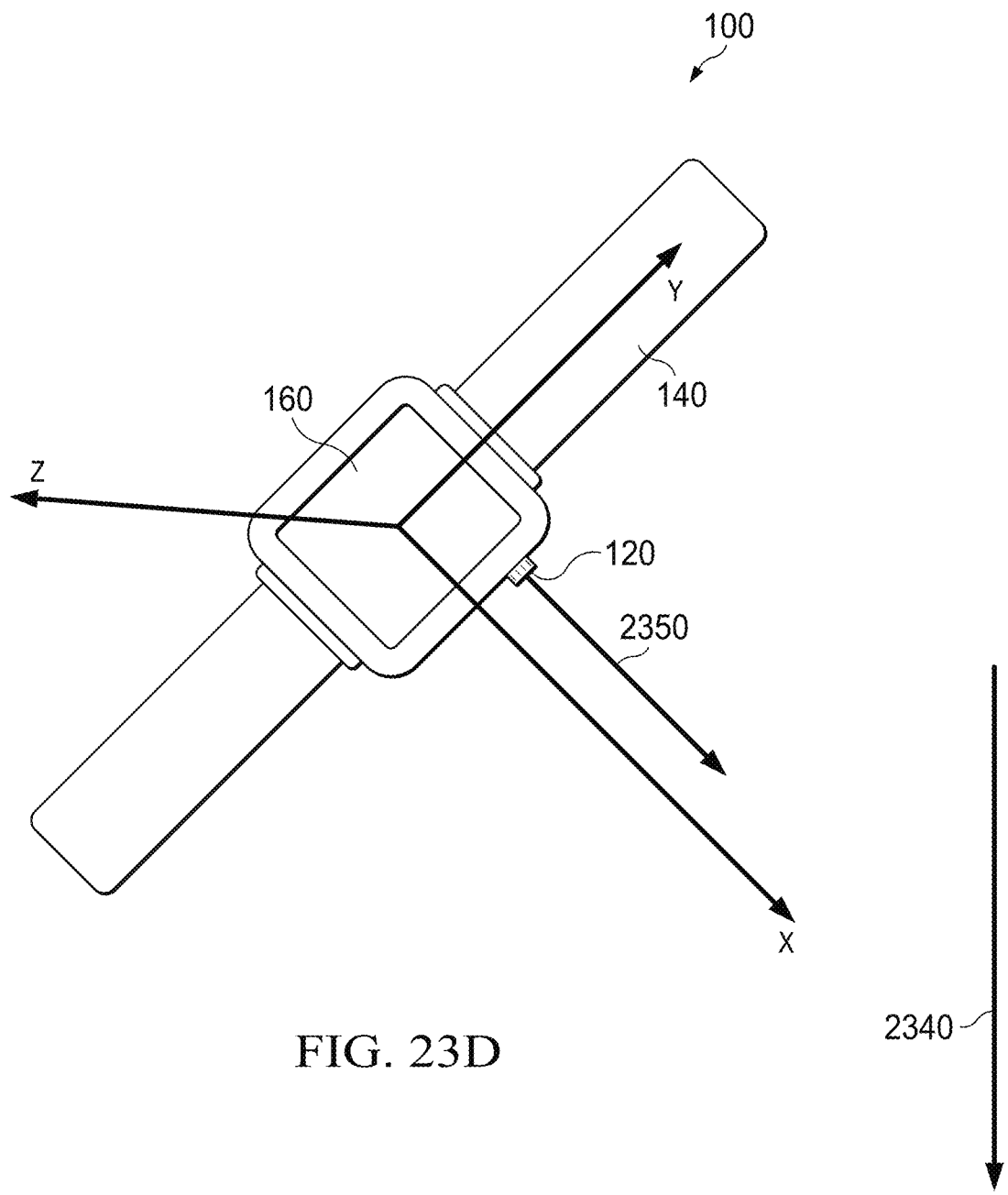

FIG. 23B-23D illustrate exemplary rotational data relative to the fixed body frame of reference 2300. The rotational data may be generated based on motion data and or magnetic field data. In FIG. 23B, the rotational data for a first device orientation 2310 includes an angle ($\phi$)) 2302 with respect to the positive x-axis, an angle ($\theta$) 2304 with respect to the positive y-axis, and an angle ($\Psi$) 2306 with respect to the positive z-axis. The first device orientation 2310 can be expressed in body-fixed frame of reference 2300 as [cos($\phi$)), cos($\theta$), cos($\Psi$)], which is a non-limiting exemplary format for the first set of rotational data. The second device orientation 2320 shown in FIG. 23B is parallel with and pointing toward the positive x-axis. Therefore, the rotational data includes the angle ($\phi$) between the second device orientation 2320 and the positive x-axis measuring 0-degrees; the angle ($\theta$) between the second device orientation 2320 and the positive y-axis measuring 90-degrees; and the angle ($\Psi$) between second device orientation 2320 and the positive z-axis measuring 90-degrees. Therefore, the second device orientation 2320 can be expressed as [cos(0), cos(90), cos (90)], which is [1, 0, 0]. A third device orientation 2330 shown FIG. 23B is parallel with and pointing toward the positive z-axis, so the rotational data for the third device orientation 2330 includes the angle ($\phi$) between the third device orientation 2330 and the positive x-axis measuring 90-degrees; the angle ($\theta$) between the third device orientation 2330 and the positive y-axis measuring 90-degrees; and the angle ($\Psi$) between the third device orientation 2330 and the positive z-axis measuring 0-degrees. Therefore, the third device orientation 2330 can be expressed as [cos(90), cos (90), cos(0)], which is [0, 0, 1]. As yet another example, the fourth device orientation 2340 represents direction of gravity in FIG. 23B and is parallel with and pointing toward the negative y-axis. The rotational data for the fourth device orientation 2340 includes the angle ($\phi$) between the fourth device orientation 2340 and the positive x-axis measuring 90-degrees; the angle ($\theta$) between the fourth device orientation 2340 and the positive y-axis measuring 180-degrees; and the angle ($\Psi$) between the fourth device orientation 2340 and the positive z-axis measuring 90-degrees. Therefore, the fourth device orientation 2340 can be expressed as [cos(90), cos(180), cos(90)], which is [0, −1, 0].

In FIG. 23C, wearable device 100 is held vertically. As discussed earlier, the x-axis is parallel with direction pointed by the crown 120, the y-axis is parallel with the band 140, and the z-axis is perpendicular to the display surface 160. A fifth device orientation 2350 in FIG. 23C is parallel with the direction pointed by the crown 120. In the rotational data for the fifth device orientation 2350, the angle ($\phi$) between the fifth device orientation 2350 and the positive x-axis measures 0-degrees; the angle ($\theta$) between the fifth device orientation 2350 and the positive y-axis measures 90-degrees; and the angle ($\Psi$) between the fifth device orientation 2350 and the positive z-axis measures 90-degrees. Therefore, the fifth device orientation 2350 can be expressed as [cos(0), cos(90), cos(90)], which is [1, 0, 0]. The fourth device orientation 2340 represents direction of gravity in FIG. 23C and is parallel with and pointing toward the negative y-axis. The rotational data for the fourth device orientation 2340 includes the angle ($\phi$) between the fourth device orientation 2340 and the positive x-axis measuring 90-degrees; the angle ($\theta$) between the fourth device orientation 2340 and the positive y-axis measuring 180-degrees; and the angle ($\Psi$) between the fourth device orientation 2340 and the positive z-axis measuring 90-degrees. Therefore, the fourth device orientation 2340 in FIG. 23C can be expressed as [cos(90), cos(180), cos(90)], which is [0, −1, 0].

In FIG. 23D, wearable device 100 is rotated 45-degree clockwise compared with FIG. 23C. As discussed earlier, the x-axis is parallel with direction pointed by the crown 120, the y-axis is parallel with the band 140, and the z-axis is perpendicular to the display surface 160. The fifth device orientation 2350 in FIG. 23D represents the direction pointed by the crown 120. The rotational data for the fifth device orientation includes the angle ($\phi$) between the fifth device orientation 2350 and the positive x-axis measuring 0-degrees; the angle ($\theta$) between the fifth device orientation 2350 and the positive y-axis measuring 90-degrees; and the angle ($\Psi$) between the fifth device orientation 2350 and the positive z-axis measuring 90-degrees. Therefore, the fifth device orientation 2350 can be expressed as [cos(0), cos(90), cos(90)], which is [1, 0, 0]. The fourth device orientation 2340 represents direction of gravity in FIG. 23D. The rotational data for the fourth device orientation 2340 includes the angle ($\phi$) between the fourth device orientation 2340 and the positive x-axis measuring 45-degrees; the angle ($\theta$) between the fourth device orientation 2340 and the positive y-axis measuring 135-degrees; and the angle ($\Psi$) between the fourth device orientation 2340 and the positive z-axis measuring 90-degrees. Therefore, the fourth device orientation 2340 in FIG. 23D can be expressed as [cos(45), cos(135), cos(0)], which is [0.707, −0.707, 0].

It is noted that the expression of the fifth device orientation 2350 is the same in FIG. 23C and FIG. 23D even though wearable device 100 has rotated. This is because the fixed-body frame of reference 2300 is always fixed with respect to wearable device 100. As a result, when position of wearable device 100 changes, the fifth device orientation changes along with three axes in the fixed-body frame of reference 2300. Therefore, the relative position between the fifth device orientation 2350 and the three axes remain the same. On the other hand, although the direction of the fourth device orientation 2340 parallel with gravity does not change in an "absolute" sense, it does not rotate together with wearable device 100. Therefore, the expression of the fourth device orientation 2340 changes in the body-fixed frame of reference 2300 when wearable device changes position.

Figure 24:
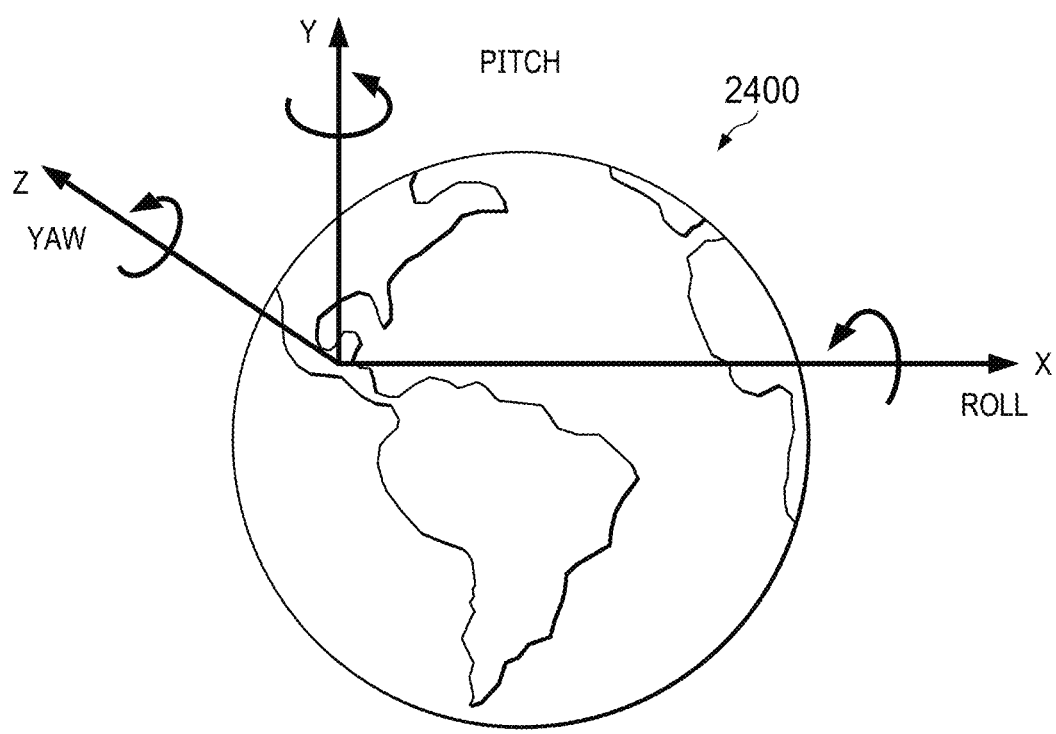
FIG. 24 illustrates an inertial frame of reference, according to embodiments of the disclosure.

FIG. 24 illustrates an inertial frame of reference 2400 according to some embodiments of the present disclosure. In FIG. 24, the z-axis (or the yaw axis) is based on the direction of gravity. The x-axis (or the roll axis) and the y-axis (or the pitch axis) can be chosen relatively arbitrarily as long as the three axes are perpendicular to each other.

Figure 25A:
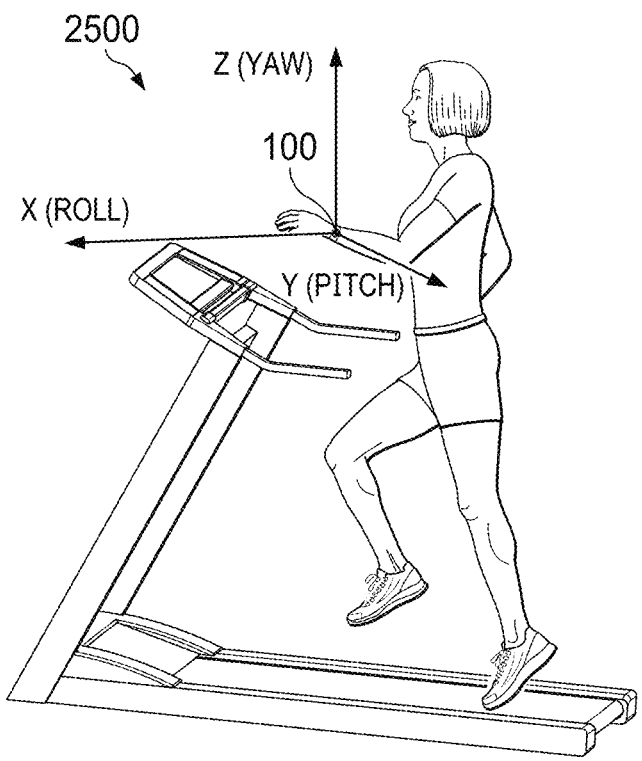
FIGS. 25A-E illustrate methods for measuring the orientation of wearable devices relative to an inertial frame of reference, according to embodiments of the disclosure.

FIGS. 25A-25E illustrate an example of an inertial frame of reference 2500 according to some embodiments of the present disclosure. FIG. 25A depicts inertial frame of reference 2500 in a context where a user is running on a treadmill without gripping the handrails. 25B depicts inertial frame of reference 2500 in a context where a user is running on a treadmill and gripping the handrails. In FIG. 25A, the z-axis (or the yaw axis) in the inertial frame of reference is based on the direction of gravity rather than the wearable device itself. In some embodiments, the x-axis (or the roll axis) and the y-axis (or the pitch axis) can be chosen relatively arbitrarily as long as the three axes are perpendicular to each other. In FIG. 25A, the z-axis is also referred to as yaw axis because any yaw movement rotates around the z-axis. Similarly, the x-axis is also referred to as roll axis because any roll movement rotates around the x-axis. The y-axis is referred to as pitch axis because any pitch movement rotates around the y-axis. By knowing the difference between the three-axis in the fixed-body frame of reference 2300 and the three-axis in the inertial frame of reference 2500, the rotational data expressed in the fixed-body frame of reference 2300 can be converted into the rotational data expressed in the inertial frame of reference 2500 using techniques appreciated by people skilled in the art.

Figure 25B:
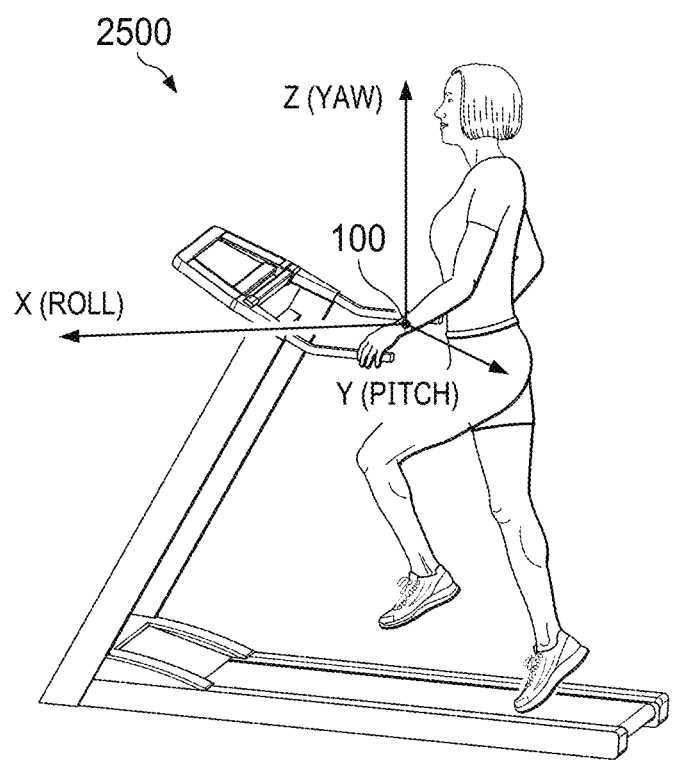

In various embodiments, when the user is running on a treadmill and gripping the handrails, as shown in FIG. 25B, the orientation or the wearable device 100 may remain constant because the user's arm/wrist pose may not change. Therefore, the rotational data and or the device orientation may not change for the period of time during the treadmill activity when the user maintains this position. During periods of zero or little change in device orientation, motion data indicating a stepping motion may not be detected. Accordingly, no change in rotational data may be detected and the device heading may remain the same. The constant direction of user travel ensures device orientations measured while the user is in this position will be included in the same cluster of rotational data in the device orientation plot. Therefore, no variable heading will be detected in when the user is in the position shown in FIG. 25B.

Figure 25C:
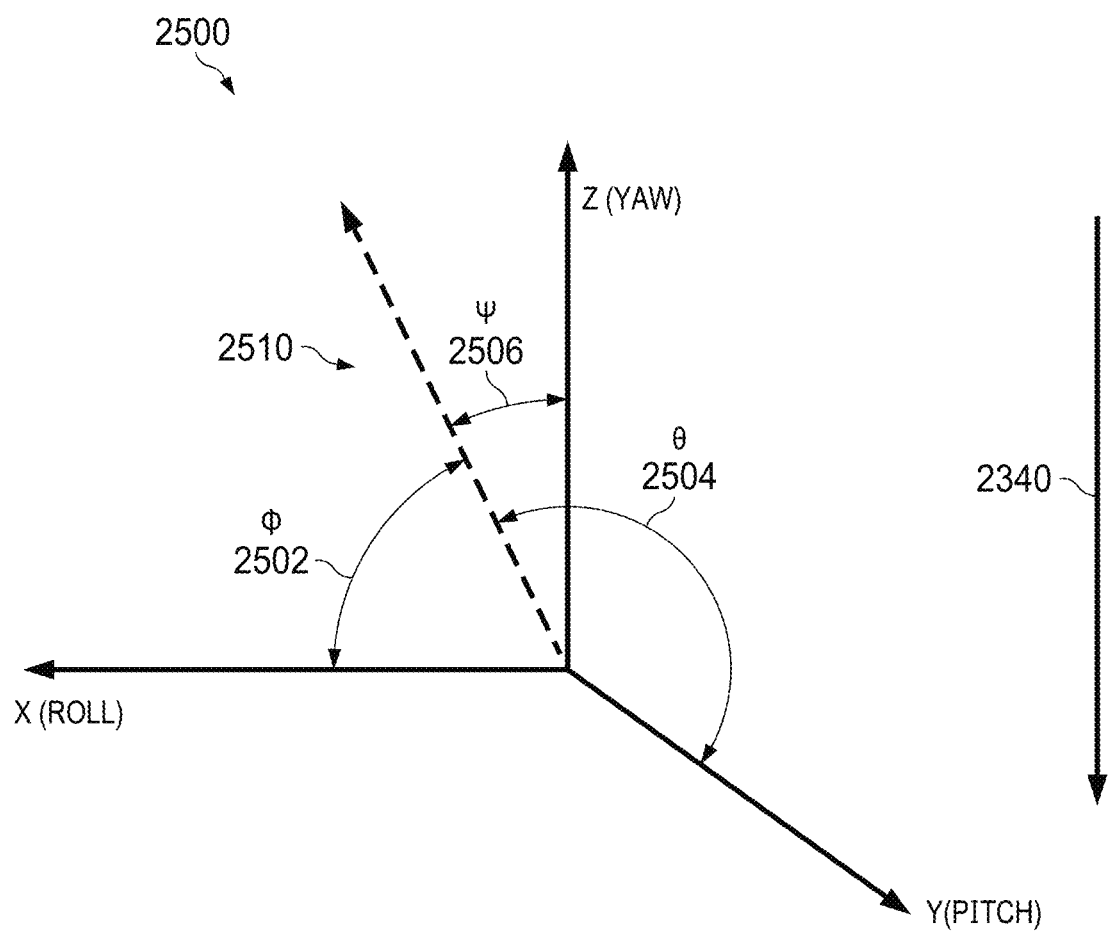

FIG. 25C illustrates rotational data of the wearable device 100 with respect to inertial frame of reference 2500. The rotational data may be used to determine a device orientation. In FIG. 25C, a sixth device orientation 2510 may be described by rotational data that includes an angle ($\phi$) 2502 with respect to the positive x-axis, an angle ($\theta$) 2504 with respect to the positive y-axis, and an angle ($\Psi$) 2506 with respect to the positive z-axis. The sixth device orientation 2510 can be expressed in body-fixed frame of reference 2500 as [cos($\phi$), cos($\theta$), cos($\Psi$)], which is an exemplary format of the rotational data used to determine the sixth device orientation.

Figure 25D:
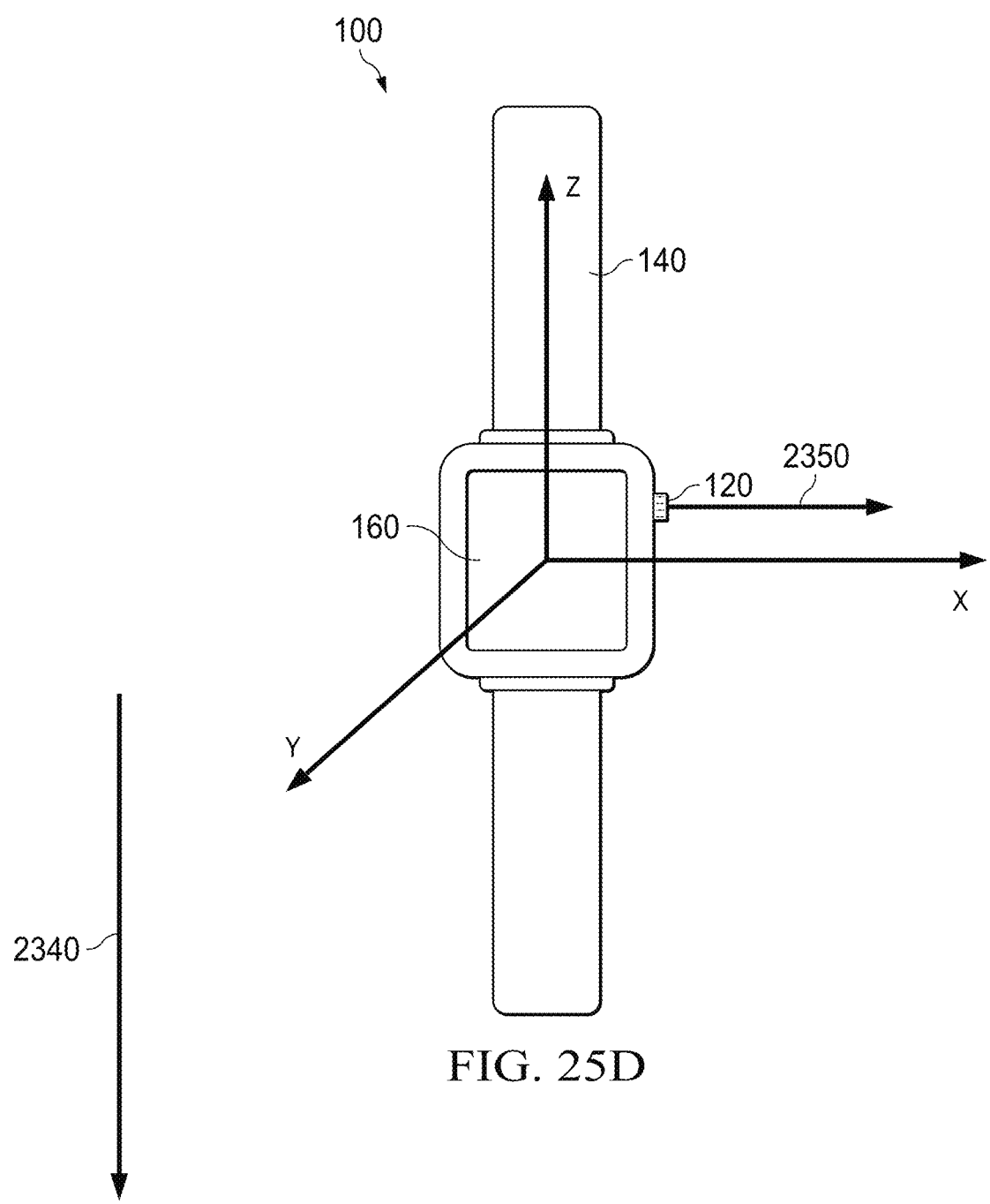
Figure 25E:
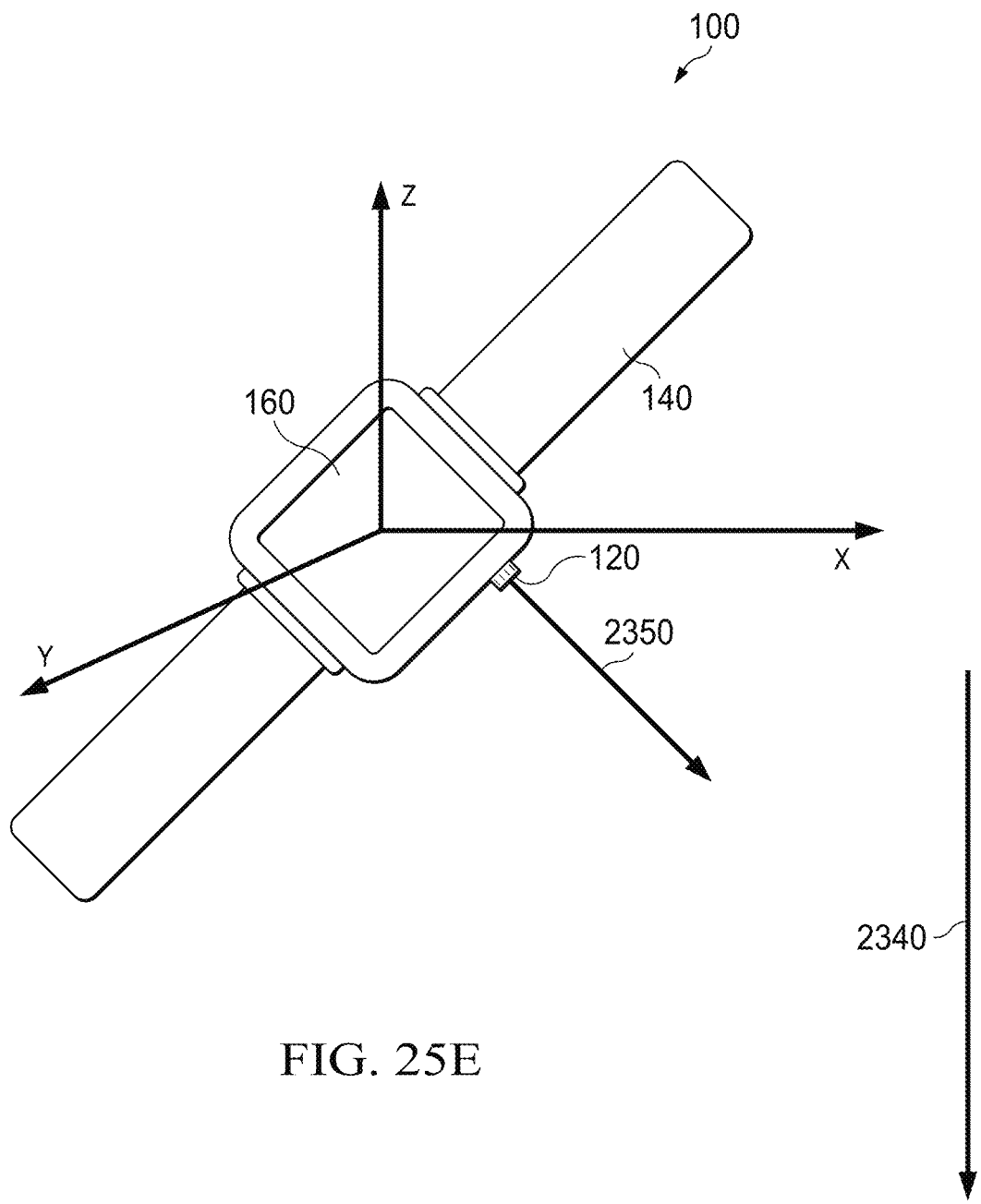

FIGS. 25D and 25E illustrate how same orientations in FIGS. 23C and 23D can be expressed differently in inertial frame of reference 2500. In FIG. 25D, wearable device 100 is held vertically, which is the same as FIG. 23C. As discussed earlier, the z-axis is based on the gravity in inertial frame of reference 2500. In FIG. 25D, the positive z-axis is chosen as the direct opposite position of gravity, the x-axis is perpendicular to the z-axis and pointing right horizontally, and the y-axis is perpendicular to both x-axis and y-axis and pointing "out" of FIG. 25D. The fifth device orientation 2350 in FIG. 25D represents the direction pointed by the crown 120, so the angle ($\phi$) between the fifth device orientation 2350 and the positive x-axis is 0-degrees; the angle ($\theta$) between the fifth device orientation 2350 and the positive y-axis is 90-degrees; and the angle ($\Psi$) between the fifth device orientation 2350 and the positive z-axis is 90-degrees. Therefore, the fifth device orientation 2350 can be expressed as [cos(0), cos(90), cos(90)], which is [1, 0, 0]. As another example, the fourth device orientation 2340 represents direction of gravity in FIG. 25D and is parallel with and pointing toward the negative z-axis, so the angle ($\phi$) between the fourth device orientation 2340 and the positive x-axis is 90-degrees; the angle ($\theta$) between the fourth device orientation 2340 and the positive y-axis is 90-degrees; and the angle ($\Psi$) between the fourth device orientation 2340 and the positive z-axis is 180-degrees. Therefore, the fourth device orientation 2340 in FIG. 25D can be expressed as [cos(90), cos(90), cos(180)], which is [0, 0, −1].

In FIG. 25E, wearable device 100 is rotated 45-degree clockwise compared with FIG. 25D. Because the three axes are based on gravity, the axes remain in the same position as FIG. 25D. The fifth device orientation 2350 in FIG. 25E represents the direction pointed by the crown 120, and the angle ($\phi$) between the fifth device orientation 2350 and the positive x-axis is 45-degrees; the angle ($\theta$) between the fifth device orientation 2350 and the positive y-axis is 90-degrees; and the angle ($\Psi$) between the fifth device orientation 2350 and the positive z-axis is 135-degrees. Therefore, the fifth device orientation 2350 can be expressed as [cos(45), cos(90), cos(135)], which is [0.707, 0, −0.707]. As another example, the fourth device orientation 2340 represents direction of gravity in FIG. 25E. The angle ($\phi$) between the fourth device orientation 2340 and the positive x-axis is 90-degrees; the angle ($\theta$) between the fourth device orientation 2340 and the positive y-axis is 90-degrees; and the angle ($\Psi$) between the fourth device orientation 2340 and the positive z-axis is 180-degrees. Therefore, the fourth device orientation 2340 in FIG. 25E can be expressed as [cos(90), cos(90), cos(180)], which is [0, 0, −1].

It is noted that the expression of the fourth device orientation 2340 is the same in FIG. 25D and FIG. 25E even though wearable device 100 has rotated. This is because the inertial frame of reference 2500 is always fixed with respect to gravity. As a result, when position of wearable device 100 changes, the three axes in inertial frame of reference 2500 do not change with the wearable device but instead remain fixed just as the direction of gravity remains fixed. On the other hand, the fifth device orientation 2350 does move with respect to the three axes in the inertial frame of reference because the fifth device orientation 2350 corresponds to the position of the crown of the wearable device. Accordingly, the rotational data describing the fifth device orientation 2350 changes in the inertial frame of reference 2500.

The foregoing description is intended to convey a thorough understanding of the embodiments described by providing a number of specific exemplary embodiments and details involving activity detection, workout performance tracking, efficient use of battery and compute resources, power management in wearable devices, cardio machine activity monitoring, device heading tracking, user direction of travel tacking, and cardio machine motion classification. It should be appreciated, however, that the present disclosure is not limited to these specific embodiments and details, which are examples only. It is further understood that one possessing ordinary skill in the art, in light of known systems and methods, would appreciate the use of the invention for its intended purposes and benefits in any number of alternative embodiments, depending on specific design and other needs.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. Therefore, the claims should be regarded as including such equivalent constructions insofar as they do not depart from the spirit and scope of the disclosed subject matter.

As used herein, the singular forms "a", "an", and "the" are intended to include the plural forms as well, unless the context clearly indicates otherwise. it will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

As used herein, the terms "and/or" and "at least one of" include any and all combinations of one or more of the associated listed items.

Certain details are set forth in the foregoing description and in FIGS. 1-25E to provide a thorough understanding of various embodiments of the present invention. Other details describing well-known structures and systems often associated with wearable devices, cardio machine activities, activity detection, workout performance tracking, efficient use of battery and compute resources, power management in wearable devices, device heading tracking, user direction of travel tracking, cardio machine motion classification, and the like, however, are not set forth below to avoid unnecessarily obscuring the description of the various embodiments of the present invention.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method for improving performance of a wearable device while recording a cardio-machine activity, the method comprising:

starting a recording of the cardio machine activity on the wearable device;

measuring, by a motion sensing module of the wearable device, motion data of a user of the wearable device;

measuring, by a heart rate sensing module of the wearable device, heart rate data of the user, the heart rate sensing module comprising a photoplethysmogram (PPG) sensor configured to be worn adjacent to the user's skin;

detecting, by a processor circuit, an end of the cardio-machine activity by:

determining rotational data from the motion data, the rotational data describing a position of the wearable device in a three-dimensional space relative to a frame of reference;

estimating a device heading based on the rotational data;

tracking the heading of the wearable device at multiple time points during the cardio machine activity to estimate a relative heading;

detecting a variable heading by determining that the relative heading exceeds a heading threshold;

detecting the end of the cardio machine activity in response to detecting the variable heading; and confirming the end of the cardio-machine activity based on at least one of the heart rate data and the motion data; and in response to the confirming the end of the cardio-machine activity, ending, by the processor circuit, the recording of cardio machine activity.

2. The method of claim 1, comprising:

determining, by the processor circuit, a current heart rate of the user at a point in time during the cardio machine activity based on the heart rate data;

determining, by the processor circuit, an average user heart rate for the heart rate data measured during the cardio machine activity;

determining, by the processor circuit, a relative heart rate by calculating a difference between the current heart rate and the average user heart rate;

comparing, by the processor circuit, the relative heart rate to a relative heart rate threshold; and confirming, by the processor circuit, the end of the cardio machine activity based on determining the relative heart rate falls below the relative heart rate threshold.

3. The method of claim 1, comprising:

calculating, by the processor circuit, a level of exertion for the user based on the heart rate of the user;

comparing, by the processor circuit, the level of exertion to a level of exertion threshold for the cardio-machine activity;

confirming, by the processor circuit, the end of the cardio machine activity based on determining the user level of exertion falls below the level of exertion threshold.

4. The method of claim 3, wherein the cardio-machine activity is at least one of a rowing activity, a stair stepper activity, a treadmill/elliptical activity, or an indoor cycling activity.

5. The method of claim 1, comprising:

receiving, by the processor circuit, magnetic field data from a magnetic field sensor of the wearable device; and improving, by the processor circuit, an accuracy of the device heading using the magnetic field data.

6. The method of claim 5, comprising:

determining, by the processor circuit, the device heading based on a first plurality of pieces of rotational data determined based on the motion data and a second plurality of pieces of rotational data determined based on the magnetic field data.

7. The method of claim 1, comprising:

characterizing, by the processor circuit, a motion of the user during the cardio-machine activity by comparing the motion data to one or more motion features included in a motion model for the cardio-machine activity.

8. The method of claim 7, comprising detecting, by the processor circuit, a non-performance of the one or more motion features in included in the motion model for the cardio-machine activity; and in response to detecting the non-performance of the one or more motion features, confirming, by the processor circuit, the end of the cardio-machine activity.

9. The method of claim 8, wherein the motion model for the cardio-machine activity is at least one of a motion model for a rowing activity, a motion model for a stair stepper activity, a motion model for a treadmill/elliptical activity, or a motion model for an indoor cycling activity.

10. The method of claim 9, wherein one or more motion features included in the motion model for the rowing activity include rowing stokes observable at intervals during the rowing activity.

11. The method of claim 7, wherein the one or more motion features included in the motion model for the stair stepper activity and the motion model for the treadmill/elliptical activity include motion data indicating no change in the wrist pose of the user.

12. The method of claim 7, wherein the one or more motion features included in the motion model for an indoor cycling activity include no observable steps, a low pose of the user, and a subtle arm swing observable at intervals during the indoor cycling activity.

13. The method of claim 7, comprising detecting, by the processor circuit, a performance of the one or more motion features in included in the motion model for the cardio-machine activity; and in response to detecting the performance of the one or more motion features, confirming, by the processor circuit, the end of the cardio-machine activity.

14. The method of claim 13, wherein the motion model for the cardio-machine activity is at least one of a motion model for a rowing activity, a motion model for a stair stepper activity, a motion model for a treadmill/elliptical activity, or a motion model for an indoor cycling activity.

15. The method of claim 14, wherein the one or more motion features for the motion model for the rowing activity include a stepping motion during the rowing activity.

16. The method of claim 14, wherein the one or more motion features for the motion model for the stair stepper activity include a rowing motion during the stair stepper activity.

17. The method of claim 14, wherein the one or more motion features for the motion model for the treadmill/elliptical activity and the motion model for the indoor cycling activity include a side stepping motion during the treadmill/elliptical activity or the indoor cycling activity.

18. A system for improving performance of a wearable device while recording a cardio machine activity, the system comprising:

a motion sensing module configured to collect motion data of a user of the wearable device;

a heart rate sensing module configured to measure heart rate data of the user, wherein the heart rate sensing module comprises a photoplethysmogram (PPG) sensor and the PPG sensor is configured to be worn adjacent to the user's skin; and a processor circuit in communication with the motion sensing module and the heart rate sensing module, the processor circuit configured to execute instructions causing the processor circuit to:

begin recording of the cardio machine activity;

determine rotational data from the motion data, the rotational data describing a position of the wearable device in a three dimensional space relative to a frame of reference;

estimate a device heading based on the rotational data;

track the device heading at multiple time points during the cardio machine activity to estimate a relative heading;

detect a variable heading by determining that the relative heading exceeds a heading threshold for the cardio machine activity, detect an end of the cardio machine activity based on the variable heading;

confirm the end of the cardio machine activity based on at least one of the heart rate data or the motion data; and end recording of the cardio machine activity in response to the confirming.

19. The system of claim 18, wherein the processor circuit is further configured to:

determine a current heart rate of the user at a point in time during the cardio machine activity;

determine an average user heart rate for the heart rate data measured during the cardio machine activity;

determine a relative heart rate by calculating a difference between the current heart rate and the average user heart rate;

compare the relative heart rate to a relative heart rate threshold; and confirm the end of the cardio machine activity when the relative heart rate falls below the relative heart rate threshold.

* * * * *

UNITED STATES PATENT AND TRADEMARK OFFICE
CERTIFICATE OF CORRECTION

| | |
|---|---|
| PATENT NO. | : 11,937,904 B2 |
| APPLICATION NO. | : 17/016020 |
| DATED | : March 26, 2024 |
| INVENTOR(S) | : James Ochs et al. |

Page 1 of 1

It is certified that error appears in the above-identified patent and that said Letters Patent is hereby corrected as shown below:

In the Claims

Column 40, Line 57, in Claim 8, after "features" delete "in";

Column 41, Line 5, in Claim 11, delete "claim 7," and insert -- claim 9, --;

Column 41, Line 17, in Claim 13, after "features" delete "in".

Signed and Sealed this
Fourteenth Day of May, 2024

Katherine Kelly Vidal
*Director of the United States Patent and Trademark Office*